(12) United States Patent
Blanco-Pillado et al.

(10) Patent No.: US 7,803,813 B2
(45) Date of Patent: *Sep. 28, 2010

(54) SUBSTITUTED 2-CARBONYLAMINO-6-PIPERIDINAMINOPYRIDINES AND SUBSTITUTED 1-CARBONYLAMINO-3-PIPERIDINAMINOBENZENES AS 5-HT1F AGONISTS

(75) Inventors: Maria-Jesus Blanco-Pillado, Indianapolis, IN (US); Dana Rae Benesh, Westfield, IN (US)

(73) Assignee: Eli Lilly and Company, Indianapolis, IN (US)

( * ) Notice: Subject to any disclaimer, the term of this patent is extended or adjusted under 35 U.S.C. 154(b) by 455 days.

This patent is subject to a terminal disclaimer.

(21) Appl. No.: 11/810,388

(22) Filed: Jun. 4, 2007

(65) Prior Publication Data

US 2007/0270466 A1    Nov. 22, 2007

Related U.S. Application Data

(63) Continuation of application No. 10/569,109, filed as application No. PCT/US2004/025607 on Sep. 3, 2004, now Pat. No. 7,291,632.

(60) Provisional application No. 60/502,780, filed on Sep. 12, 2003.

(51) Int. Cl.
  *A61K 31/445* (2006.01)
  *C07D 211/56* (2006.01)
(52) U.S. Cl. ................................ 514/318; 546/224
(58) Field of Classification Search ............... 546/237, 546/224; 514/331, 318
See application file for complete search history.

(56) References Cited

U.S. PATENT DOCUMENTS

| 5,521,196 | A | 5/1996 | Audia et al. |
| 5,521,197 | A | 5/1996 | Audia |
| 5,708,187 | A | 1/1998 | Flaugh et al. |
| 5,721,252 | A | 2/1998 | Audia et al. |
| 5,814,653 | A | 9/1998 | Flaugh et al. |
| 7,291,632 | B2 * | 11/2007 | Blanco-Pillado et al. ..... 514/318 |

FOREIGN PATENT DOCUMENTS

| WO | WO 96/29075 | 9/1996 |
| WO | WO 97/13512 | 4/1997 |
| WO | WO 98/08502 | 3/1998 |
| WO | WO 98/15545 | 4/1998 |
| WO | WO 98/20875 | 5/1998 |
| WO | WO 98/46570 | 10/1998 |
| WO | WO 98/55115 | 12/1998 |
| WO | WO 99/25348 | 5/1999 |
| WO | WO 00/00487 | 1/2000 |
| WO | WO 00/00490 | 1/2000 |
| WO | WO 00/34266 | 6/2000 |
| WO | WO 00/47559 | 8/2000 |
| WO | WO 00/50426 | 8/2000 |
| WO | WO 03/084949 A1 | 10/2003 |
| WO | WO 2004/094380 A1 | 11/2004 |

\* cited by examiner

*Primary Examiner*—Janet L Andres
*Assistant Examiner*—Binta M Robinson
(74) *Attorney, Agent, or Firm*—Ivor R. Elrifi; Heidi A. Erlacher; Mintz, Levin, Cohn, Ferris, Glovsky and Popeo, P.C.

(57) ABSTRACT

The present invention relates to compounds of formula I:

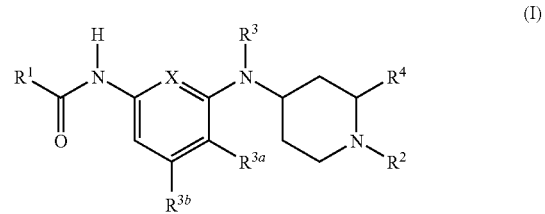

(I)

or a pharmaceutically acceptable acid addition salt thereof, wherein X is $C(R3^c)=$ or $N=$; $R^1$ is $C_2$-$C_6$ alkyl, substituted $C_2$-$C_6$ alkyl, $C_3$-$C_7$ cycloalkyl, substituted $C_3$-$C_7$ cycloalkyl, phenyl, substituted phenyl, heterocycle, or substituted heterocycle; $R^2$ is hydrogen, $C_1$-$C_3$ n-alkyl, $C_3$-$C_6$ cycloalkyl-$C_1$-$C_3$ alkyl, or a group of formula II

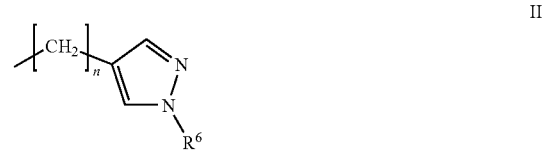

II provided that when $R^1$ is $C_2$-$C_6$ alkyl or substituted $C_2$-$C_6$ alkyl, $R^2$ is hydrogen or methyl; $R^{3a}$, $R^{3b}$ and, when X is —$C(R^{3c})$=, $R^{3c}$, are each independently hydrogen, fluoro, or methyl, provided that no more than one of $R^{3a}$, $R^{3b}$, and $R^{3c}$ may be other than hydrogen; $R^4$ is hydrogen or $C_1$-$C_3$ alkyl; $R^5$ is hydrogen, $C_1$-$C_3$ alkyl, or $C_3$-$C_6$ cycloalkylcarbonyl, provided that when $R^{3a}$ is other than hydrogen, $R^5$ is hydrogen; $R^6$ is hydrogen or $C_1$-$C_6$ alkyl; and n is an integer from 1 to 6 inclusively. The compounds of the present invention are useful for activating $5HT_{1F}$ receptors, inhibiting neuronal protein extravasation, and for the treatment or prevention of migraine in a mammal.

6 Claims, No Drawings

SUBSTITUTED 2-CARBONYLAMINO-6-PIPERIDINAMINOPYRIDINES AND SUBSTITUTED 1-CARBONYLAMINO-3-PIPERIDINAMINOBENZENES AS 5-HT1F AGONISTS

RELATED APPLICATIONS

This application is a continuation of, and claims priority to, prior application U.S. Ser. No. 10/569,109, filed Feb. 21, 2006, now U.S. Pat. No. 7,291,632 which claims the benefit of PCT/US04/025607, filed Sep. 3, 2004, which claims the benefit of U.S. Ser. No. 60/502,780, filed Sep. 12, 2003, now abandoned. The contents of these applications are incorporated by reference herein in their entireties.

BACKGROUND OF THE INVENTION

Until recently, theories regarding the pathophysiology of migraine have been dominated since 1938 by the work of Graham and Wolff. *Arch. Neurol. Psychiatry*, 39: 737-63, 1938. They proposed that the cause of migraine headache was vasodilatation of extracranial vessels. This view was supported by knowledge that ergot alkaloids and sumatriptan, a hydrophilic $5\text{-HT}_1$ agonist which does not cross the blood-brain barrier, induce contraction of cephalic vascular smooth muscle and are effective in the treatment of migraine. Humphrey, et al., *Ann. NY Acad. Sci.*, 600: 587-600, 1990. Recent work by Moskowitz has shown, however, that the occurrence of migraine headaches is independent of changes in vessel diameter. *Cephalalgia*, 12: 5-7, 1992.

Moskowitz has proposed that currently unknown triggers for pain stimulate trigeminal ganglia that innervate vasculature within the cephalic tissue, giving rise to release of vasoactive neuropeptides from axons on the vasculature. These released neuropeptides then activate a series of events, a consequence of which is pain. This neurogenic inflammation is blocked by sumatriptan and ergot alkaloids by mechanisms involving 5-HT receptors, believed to be closely related to the $5\text{-HT}_{1D}$ subtype, located on the trigeminovascular fibers. *Neurology*, 43 (suppl. 3): S16-S20 1993. Sumatriptan, in fact, has high affinity for the $5\text{-HT}_{1B}$ and $5\text{-HT}_{1D}$ receptors, $K_i$=10.3 nM and 5.1 nM, respectively, which activity may be indicative of vasoconstrictive activity. Sumatriptan and similar compounds previously advanced for the treatment of migraine had tended to be selected on the basis of this vasoconstrictive activity under the premises of the prior art models for migraine.

Serotonin (5-HT) exhibits diverse physiological activity mediated by at least seven receptor classes, the most heterogeneous of which appears to be $5\text{-HT}_1$. A human gene which expresses one of these $5\text{-HT}_1$ receptor subtypes, named $5\text{-HT}_{1F}$, was isolated by Kao and coworkers. *Proc. Natl. Acad. Sci. USA*, 90: 408-412, 1993. This $5\text{-HT}_{1F}$ receptor exhibits a pharmacological profile distinct from any serotonergic receptor yet described. It was found that sumatriptan, in addition to the above mentioned strong affinities for the $5\text{-HT}_{1B}$ and $5\text{-HT}_{1D}$ receptors, also has affinity for the $5\text{-HT}_{1F}$ receptor subtype, with a $K_i$ of about 23 nM. This suggests a possible role for the $5\text{-HT}_{1F}$ receptor in migraine.

Various $5\text{-HT}_{1F}$ receptor agonists have subsequently been developed which have shown relative selectivity for the $5\text{-HT}_{1F}$ receptor subclass and it has been shown that such selectivity generally reduces the vasoconstrictive activity characteristic of other compounds advanced as potential agents for the treatment of migraine and associated disorders. Included among these $5\text{-HT}_{1F}$ receptor agonists are compounds disclosed in the following:

U.S. Pat. Nos. 5,708,187 and 5,814,653, describing a family of 6-substituted-3-amino (alkyl)-tetrahydrocarbazoles and 7-substituted-4-amino(alkyl)cyclohepta[7,6b]indoles;

U.S. Pat. No. 5,521,196, U.S. Pat. No. 5,721,252, U.S. Pat. No. 5,521,197, and WO 96/29075, describing various families of 5-substituted piperidin-3-yl-indoles and 5-substituted 1,2,3,6 tetrahydropyridin-3-yl-indoles;

WO 97/13512 describing a family of 5-substituted 3-aminoethylindoles;

WO 98/46570 describing a family of 5-substituted indoles, pyrrolo[3,2-b]pyridines, benzofurans, and benzothiophenes, having the 3-position substituted with octahydroindolizinyl, octahydro-2H-quinolizinyl, decahydropyrido[1,2-a]azepinyl, 1,2,3,5,8,8a-hexahydroindolizinyl, 1,3,4,6,9,9a-hexahydro-2H-quinolizinyl, or 1,4,6,7,8,9,10,10a-octahydropyrido[1,2-a] azepinyl;

WO 98/20875 and WO 99/25348 describing two families of 5-substituted piperidin-3-yl-azaindoles and 5-substituted 1,2,3,6-tetrahydropyridin-3-yl-azaindoles;

WO 00/00487 describing a family of 5-substituted (piperidin-3-yl or 1,2,3,6-tetrahydropyridin-3-yl)indoles, azaindoles, benzofurans, and benzothiophenes;

WO 98/08502 describing a family of 8-substituted-1,2,3,4-tetrahydro-2-dibenzofuranamines and 9-substituted-2-aminocyclohepta[b]benzofurans;

WO 98/55115 describing a family of 3-amino-1,2,3,4-tetrahydro-9H-carbazole-6-carboxamides and 4-amino-10H-cyclohepta[7,6-b]indole-7-carboxamides;

WO 98/15545 describing a select family of 3,5-disubstituted indoles and benzofurans;

WO 00/00490 describing a family of 5-allyl-substituted (piperidin-3-yl or 1,2,3,6-tetrahydropyridin-3-yl)indoles, azaindoles, benzofurans, and benzothiophenes;

WO 00/47559 describing a family of 4-(3-substituted-benzoyl)piperidines;

WO 00/50426 describing a family of 3,5-disubstituted azabenzofurans; and

WO 00/34266 describing a family of 3-heteroaryl-5-(2-(aryl or heteroaryl)-2-oxoethyl) indoles.

Continued research has now surprisingly yielded a new and unexpected class of novel selective $5\text{-HT}_{1F}$ agonists having distinct chemical and receptor binding properties, which inhibit peptide extravasation, while avoiding significant vasoconstrictive activity, and are therefore useful for the treatment of migraine and other $5\text{-HT}_{1F}$ receptor associated disorders.

SUMMARY OF THE INVENTION

The present invention relates to substituted 2-carbonylamino-6-piperidinaminopyridines and substituted 1-carbonylamino-3-piperidinaminobenzenes compounds of the general formula I:

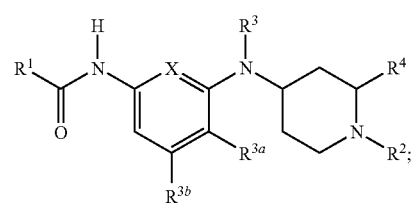

or a pharmaceutically acceptable acid addition salt thereof, where:

X is —C($R^{3c}$)= or —N=;

$R^1$ is $C_2$-$C_6$ alkyl, substituted $C_2$-$C_6$ alkyl, $C_3$-$C_7$ cycloalkyl, substituted $C_3$-$C_7$ cycloalkyl, phenyl, substituted phenyl, heterocycle, or substituted heterocycle;

$R^2$ is hydrogen, $C_1$-$C_3$ n-alkyl, $C_3$-$C_6$ cycloalkyl-$C_1$-$C_3$ alkyl, or a group of formula II

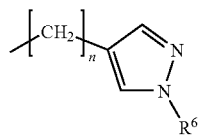

II provided that when $R^1$ is $C_2$-$C_6$ alkyl or substituted $C_2$-$C_6$ alkyl, $R^2$ is hydrogen or methyl;

$R^{3a}$, $R^{3b}$ and, when X is —C($R^{3c}$)=, $R^{3C}$, are each independently hydrogen, fluoro, or methyl, provided that no more than one of $R^{3a}$, $R^{3b}$, and $R^{3c}$ may be other than hydrogen;

$R^4$ is hydrogen or $C_1$-$C_3$ alkyl;

$R^5$ is hydrogen, $C_1$-$C_3$ alkyl, or $C_3$-$C_6$ cycloalkylcarbonyl, provided that when $R^{3a}$ is other than hydrogen, $R^5$ is hydrogen;

$R^6$ is hydrogen or $C_1$-$C_6$ alkyl; and n is an integer from 1 to 6 inclusively.

The present invention also relates to pharmaceutical compositions comprising a compound of formula I, or a pharmaceutically acceptable acid addition salt thereof, and a pharmaceutically acceptable carrier, diluent, or excipient. In another embodiment, the present invention relates to pharmaceutical compositions adapted for the activation of 5-$HT_{1F}$ receptors, for the inhibition of neuronal protein extravasation, and/or for the treatment or prevention of migraine in mammals, particularly humans, containing a compound of formula I, or a pharmaceutically acceptable acid addition salt thereof, and a pharmaceutically acceptable carrier, diluent, or excipient.

In addition, the present invention relates to a method for activating 5-$HT_{1F}$ receptors in mammals, particularly humans, comprising administering to a mammal in need of such activation an effective amount of a compound of formula I, or a pharmaceutically acceptable acid addition salt thereof.

Moreover, the present invention relates to a method for inhibiting neuronal protein extravasation in mammals, particularly humans, comprising administering to a mammal in need of such inhibition an effective amount of a compound of formula I, or a pharmaceutically acceptable acid addition salt thereof.

Additionally, the present invention relates to a method for treating or preventing migraine in mammals, particularly humans, comprising administering to a mammal in need of such treatment or prevention, an effective amount of a compound of formula I, or a pharmaceutically acceptable acid addition salt thereof.

Another aspect of the present invention relates to the use of a compound of formula I as a medicament, and in particular a medicament adapted for the activation of 5-$HT_{1F}$ receptors, for the inhibition of neuronal protein extravasation, and/or for the treatment or prevention of migraine in mammals, particularly humans. That is to say, the present invention relates to the use of a compound of formula I for the activation of 5-$HT_{1F}$ receptors, for the inhibition of neuronal protein extravasation, and/or for the treatment or prevention of migraine in mammals, particularly in humans.

Additionally, the present invention relates to the use of one or more compounds of formula I in the manufacture of a medicament for the activation of 5-$HT_{1F}$ receptors, for the inhibition of neuronal protein extravasation, and/or for the treatment or prevention of migraine in mammals, particularly in humans.

Furthermore, the present invention provides for methods for the treatment and/or prevention of 5-$HT_{1F}$-mediated disorders comprising administering to a mammal in need of such treatment or prevention, particularly a human, an effective amount of a compound of formula I, or a pharmaceutically acceptable acid addition salt thereof. In preferred embodiments, the 5-$HT_{1F}$-mediated disorder is neuronal protein extravasation and/or migraine.

DETAILED DESCRIPTION OF THE INVENTION

The following detailed description is provided to aid those skilled in the art in practicing the present invention. Even so, the following description should not be construed to unduly limit the present invention in that modifications and variations in the embodiments discussed herein can be made by those of ordinary skill in the art without departing from the spirit or scope of the present inventive discovery. Such modifications and variations are contemplated as being within the scope of the invention.

One embodiment of the present invention is a method for increasing activation of 5-$HT_{1F}$ receptors, while avoiding vasoconstrictive activity, for treating a variety of disorders that have been linked to decreased neurotransmission of serotonin in mammals. Included among these disorders are migraine, general pain, trigeminal neuralgia, dental pain or temperomandibular joint dysfunction pain, anxiety, general anxiety disorder, panic disorder, depression, disorders of sleep, chronic fatigue syndrome, premenstrual syndrome or late luteal phase syndrome, post-traumatic syndrome, memory loss, dementia including dementia of aging, social phobia, autism, attention deficit hyperactivity disorder, disruptive behavior disorders, impulse control disorders, borderline personality disorder, obsessive compulsive disorder, premature ejaculation, erectile dysfunction, bulimia, anorexia nervosa, alcoholism, tobacco abuse, mutism, and trichotillomania. The compounds of this invention are also useful as a prophylactic treatment for migraine. Any of these methods employ a compound of formula I. In preferred embodiments, the mammal to be treated by the administration of the compounds of formula I is human.

In those instances where the disorders which can be treated by serotonin agonists are known by established and accepted classifications, their classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision (ICD-10), provides classifications for many of the disorders described herein. The skilled artisan will recognize that there are alternative nomenclatures, nosologies, and classification systems for disorders described herein, including those as described in the DSM-IV and ICD-10, and that terminology and classification systems evolve with medical scientific progress.

The use of a compound of formula I for the activation of the 5-$HT_{1F}$ receptor, for the inhibition of neuronal peptide extravasation, in general or due to stimulation of the trigeminal ganglia specifically, and/or for the treatment of any of the disorders described above, are all embodiments of the present invention. In one preferred embodiment, the invention provides a method for the treatment of migraine in a mammal, as for example a human, comprising administering to a mammal in need of such treatment, a pharmaceutically effective amount of a compound of formula I. In another preferred embodiment, the invention provides a method for the prevention of migraine in a mammal, as for example a human, comprising administering to a mammal in need of such treatment, a pharmaceutically effective amount of a compound of formula I.

Likewise, the use of a compound of formula I, or a combination of more than one compound of formula I, in the manufacture of a medicament for the activation of the 5-HT$_{1F}$ receptor, for the inhibition of neuronal peptide extravasation, in general or due to stimulation of the trigeminal ganglia specifically, and/or for the treatment of any of the disorders described above, are also all embodiments of the present invention.

The general chemical terms used throughout have their usual meanings. For example, the term alkyl refers to a branched or unbranched saturated hydrocarbon group. The term "n-alkyl" refers to an unbranched alkyl group. By way of illustration, but without limitation, the term "$C_1$-$C_2$ alkyl" refers to methyl and ethyl. The term "$C_1$-$C_3$ n-alkyl" refers to methyl, ethyl, and n-propyl. The term "$C_1$-$C_3$ alkyl" refers to methyl, ethyl, n-propyl, and isopropyl. The term "$C_1$-$C_4$ alkyl" refers to methyl, ethyl, n-propyl, isopropyl, n-butyl, isobutyl, sec-butyl, and t-butyl. The term "$C_1$-$C_6$ alkyl" refers to all branched and unbranched alkyl groups having from one to six carbon atoms. The term "$C_2$-$C_6$ alkyl" refers to all branched and unbranched alkyl groups having from two to six carbon atoms. The term "$C_3$-$C_6$ cycloalkyl" refers to cyclopropyl, cyclobutyl, cyclopentyl, and cyclohexyl. The term "$C_3$-$C_7$ cycloalkyl" also includes cycloheptyl. Cycloalkylalkyl refers to a cycloalkyl moiety linked through an n-alkyl chain, as for example, but not limited to, "$C_3$-$C_6$ cycloalkyl-$C_1$-$C_3$ alkyl," which refers to a $C_3$-$C_6$ cycloalkyl moiety linked through a 1 to 3 carbon n-alkyl chain. Each alkyl, cycloalkyl, and cycloalkylalkyl group may be optionally substituted as provided for herein. Among compounds wherein $R^1$ is cycloalkyl, compounds wherein X is —N= are preferred over compounds wherein X is —C($R^{3C}$)=.

The terms "alkoxy", "phenyloxy", "benzyloxy" and "pyrimidinyloxy" refer to an alkyl group, phenyl group, benzyl group, or pyrimidinyl group, respectively, each optionally substituted as provided for herein, that is bonded through an oxygen atom.

The terms "alkylthio", "phenylthio", and "benzylthio" refer to an alkyl group, phenyl group, or benzyl group, respectively, each optionally substituted as provided for herein, that is bonded through a sulfur atom.

The term "$C_1$-$C_4$ acyl" refers to a formyl group or a $C_1$-$C_3$ alkyl group bonded through a carbonyl moiety. The term "$C_1$-$C_4$ alkoxycarbonyl" refers to a $C_1$-$C_4$ alkoxy group bonded through a carbonyl moiety. The term $C_3$-$C_6$ cycloalkylcarbonyl refers to a $C_3$-$C_6$ cycloalkyl group bonded through a carbonyl moiety.

The term "halo" refers to fluoro, chloro, bromo, or iodo. Preferred halo groups are fluoro, chloro, and bromo. More preferred halo groups are fluoro and chloro.

The term "heterocycle" is taken to mean a saturated or unsaturated 5- or 6-membered ring containing from 1 to 3 heteroatoms selected from nitrogen, oxygen and sulfur, said ring optionally being benzofused. Exemplary heterocycles, for the purposes of the present invention, include furanyl, thiophenyl, pyrrolyl, pyrrolidinyl, pyridinyl, N-methylpyrrolyl, oxazolyl, isoxazolyl, pyrazolyl, imidazolyl, triazolyl, oxadiazolyl, thiadiazolyl, thiazolyl, thiazolidinyl, N-acetylthiazolidinyl, pyrimidinyl, pyrazinyl, pyridazinyl, and the like. Exemplary benzofused heterocycles, for the purposes of the present invention, include isoquinolinyl, benzoxazolyl, benzodioxolyl, benzothiazolyl, quinolinyl, benzofuranyl, benzothiophenyl, indolyl, and the like, all of which may be optionally substituted, which also includes optionally substituted on the benzo ring when the heterocycle is benzofused.

In one embodiment, preferred heterocycles include furanyl, thiophenyl, pyrrolyl, pyridinyl, N-methylpyrrolyl, pyrimidinyl, pyrazinyl, indolyl, benzofuranyl, benzothiophenyl, benzodioxolyl, and thiazolidinyl, all of which may be optionally substituted.

In yet another embodiment, preferred heterocycles include pyridinyl, thiophenyl, and furanyl, all of which may be optionally substituted.

Substituted alkyl, cycloalkyl, cycloalkylalkyl, alkoxy, or alkylthio, means an alkyl, cycloalkyl, cycloalkylalkyl, alkoxy, or alkylthio group, respectively, substituted one or more times independently with a substituent selected from the group consisting of halo, hydroxy, and $C_1$-$C_3$ alkoxy. Substitutions on cycloalkylalkyl moieties may be on the ring portion or the alkyl linker portion or both. Preferred substitutions include substitution 1-5 times with halo, each independently selected, or substituted 1-3 times with halo and 1-2 times independently with a group selected from hydroxy and $C_1$-$C_3$ alkoxy, or substituted 1-3 times independently with a group selected from hydroxy and $C_1$-$C_3$ alkoxy, provided that no more than one hydroxy and/or alkoxy substituent may be attached through the same carbon.

The terms "substituted phenyl" and "substituted heterocycle" are taken to mean that the cyclic moiety in either case is substituted with one or more halo substituents, preferably one to five, more preferably one to three, each independently selected; or substituted with one or more substituents, preferably one to two substituents, independently selected from the group consisting of halo, $C_1$-$C_4$ alkyl, $C_1$-$C_4$ alkoxy, $C_1$-$C_4$ alkylthio, cyano, and nitro, wherein each alkyl, alkoxy and alkylthio substituent can be further substituted independently with $C_1$-$C_2$ alkoxy or with one to five halo groups selected from fluoro and chloro; or substituted with one substituent selected from the group consisting of phenyloxy, benzyloxy, phenylthio, benzylthio, and pyrimidinyloxy, wherein the phenyloxy, benzyloxy, phenylthio, benzylthio, and pyrimidinyloxy moiety can be further substituted with one to two substituents selected from the group consisting of halo, $C_1$-$C_2$ alkyl, and $C_1$-$C_2$ alkoxy, wherein each alkyl and alkoxy group can be further substituted with 1 to 3 fluoro groups; or substituted with one substituent selected from the group consisting of $C_1$-$C_4$ acyl and $C_1$-$C_4$ alkoxycarbonyl, and further substituted with zero to one substituent selected from the group consisting of halo, $C_1$-$C_4$ alkyl, $C_1$-$C_4$ alkoxy, and $C_1$-$C_4$ alkylthio. When a substituent is halo, preferred halo groups are fluoro, chloro, and bromo.

In another embodiment, preferred substitutions for "substituted phenyl" and "substituted heterocycle" include substitution with one or more halo substituents, preferably one to five, more preferably one to three, each independently selected; or substituted with one or more substituents, preferably one to two substituents, independently selected from the group consisting of halo, $C_1$-$C_4$ alkyl, $C_1$-$C_4$ alkoxy, cyano, and nitro, wherein each alkyl and alkoxy substituent can be further substituted independently with one to five halo groups selected from fluoro and chloro.

In another embodiment, preferred substitutions for "substituted phenyl" include substitution with one or three independently selected halo substituents; or substituted with one to two substituents, independently selected from the group consisting of halo, methyl, methoxy, trifluoromethyl, trifluoromethoxy, and cyano.

Abbreviations used herein are defined as follows:

BINAP means 2,2'-bis(diphenylphosphino)-1,1'binaphthyl.

DMF means N,N-dimethylformamide.

DMSO means dimethylsulfoxide.

$Pd_2(dba)_3$ means tris(dibenzylideneacetone)dipalladium (0)

$Pd(OAc)_2$ means palladium diacetate.

THF means tetrahydrofuran.

The term "amino protecting group" as used in this specification refers to a substituent commonly employed to block or protect the amino functionality while reacting other functional groups on the compound. Examples of such amino-protecting groups include the formyl group, the trityl group, the phthalimido group, the acetyl group, the trichloroacetyl group, the chloroacetyl, bromoacetyl, and iodoacetyl groups, urethane-type blocking groups such as benzyloxycarbonyl, 9-fluorenylmethoxycarbonyl ("FMOC"), t-butoxycarbonyl (t-BOC), and the like; and like amino protecting groups. The species of amino protecting group employed is not critical so long as the derivatized amino group is stable to the conditions of subsequent reactions on other positions of the molecule and can be removed at the appropriate point without disrupting the remainder of the molecule. The selection and use (addition and subsequent removal) of amino protecting groups is well known within the ordinary skill of the art. Further examples of groups referred to by the above terms are described by T. W. Greene and P. G. M. Wuts, "Protective Groups in Organic Synthesis", $3^{rd}$ edition, John Wiley and Sons, New York, N.Y., 1999, chapter 7, hereafter referred to as "Greene".

The term "pharmaceutical" or "pharmaceutically acceptable" when used herein as an adjective, means substantially non-toxic and substantially non-deleterious to the recipient.

By "pharmaceutical composition" it is further meant that the carrier, solvent, excipients and salt must be compatible with the active ingredient of the composition (e.g. a compound of formula I). It is understood by those of ordinary skill in this art that the terms "pharmaceutical formulation" and "pharmaceutical composition" are generally interchangeable, and they are so used for the purposes of this application.

The term "acid addition salt" refers to a salt of a compound prepared by reaction of the compound with a mineral or organic acid. The compounds of the present invention form pharmaceutically acceptable acid addition salts with a wide variety of organic and inorganic acids and include the physiologically acceptable salts which are often used in pharmaceutical chemistry. Such salts are also embodiments of this invention. A "pharmaceutically-acceptable (acid) addition salt" is formed from a pharmaceutically-acceptable acid as is well known in the art. Such salts include the pharmaceutically acceptable salts exemplified in Berge, S. M, Bighley, L. D., and Monkhouse, D. C., *J. Pharm. Sci.*, 66:1, (1977), which are well known to those skilled in the art.

Inorganic acids commonly employed to form such salts include hydrochloric acid, hydrobromic acid, hydroiodic acid, sulfuric acid, phosphoric acid, and the like. Organic acids commonly employed to form such salts include p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. It is well known that such compounds can form salts in various molar ratios to provide for example the hemi-acid, mono-acid, di-acid salts, etc.

The term "effective amount" means an amount of a compound of formula I which is capable of activating $5\text{-HT}_{1F}$ receptors and/or inhibiting neuronal protein extravasation.

The term "suitable solvent" refers to any solvent, or mixture of solvents, inert to the ongoing reaction that sufficiently solubilizes the reactants to afford a medium within which to effect the desired reaction.

It is understood that compounds of the present invention may exist as stereoisomers. As such, all enantiomers, diastereomers, and mixtures thereof, are included within the scope of the present invention. Where specific stereochemistries are identified in this application, the Cahn-Prelog-Ingold designations of (R)- and (S)- and the cis and trans designation of relative stereochemistry are used to refer to specific isomers and relative stereochemistry. While all enantiomers, diastereomers, and mixtures thereof, are contemplated within the present invention, preferred embodiments are single enantiomers and single diastereomers.

While all of the compounds of the present invention are useful as $5\text{-HT}_{1F}$ agonists, certain classes are preferred, as for example, compounds having any of the following enumerated selections of substituents: Compounds wherein 1) $R^1$ is phenyl, substituted phenyl, heterocycle, or substituted heterocycle;
2) $R^1$ is substituted phenyl;
3) $R^1$ is mono- or di-substituted phenyl wherein the substituents are independently selected from halo, $C_1$-$C_4$ alkyl, $C_1$-$C_4$ alkoxy, trifluoromethyl, trifluoromethoxy, trifluoroethoxy, phenyloxy, benzyloxy, cyano, and nitro;
4) $R^1$ is mono- or di-substituted phenyl wherein the substituents are independently selected from halo, $C_1$-$C_2$ alkoxy, trifluoromethyl, trifluoromethoxy, and trifluoroethoxy;
5) $R^1$ is mono- or di-substituted phenyl wherein the substituents are independently selected from halo, trifluoromethyl, and trifluoromethoxy;
6) $R^1$ is mono-, di- or tri-halo substituted phenyl;
7) $R^1$ is heterocycle or substituted heterocycle;
8) $R^1$ is heterocycle or substituted heterocycle wherein the heterocycle is selected from the group consisting of furanyl, thiophenyl, pyrrolyl, pyrrolidinyl, pyridinyl, N-methylpyrrolyl, oxazolyl, isoxazolyl, pyrazolyl, imidazolyl, triazolyl, oxadiazolyl, thiadiazolyl, thiazolyl, thiazolidinyl, N-acetylthiazolidinyl, pyrimidinyl, pyrazinyl, pyridazinyl, isoquinolinyl, benzoxazolyl, benzodioxolyl, benzothiazolyl, quinolinyl, benzofuranyl, benzothiophenyl, and indolyl;
9) $R^1$ is a substituted or unsubstituted heterocycle wherein the heterocycle is selected from the group consisting of pyridinyl, indolyl, furanyl, benzofuranyl, thiophenyl, benzodioxolyl, and thiazolidinyl;
10) $R^1$ is a substituted or unsubstituted heterocycle wherein the heterocycle is selected from the group consisting of pyridinyl, thiophenyl, and furanyl;
11) $R^1$ is mono-, di-, or tri-halo-substituted heterocycle, each halo group being independently selected;

12) $R^1$ is mono- or di-substituted heterocycle, wherein one of the substituents is selected from the group consisting of $C_1$-$C_2$ alkoxy, phenoxy, and phenylthio;
13) $R^1$ is mono-substituted heterocycle, wherein the substituents is halo or nitro;
14) $R^1$ is mono-halo substituted heterocycle;
15) $R^1$ is unsubstituted heterocycle;
16) $R^1$ is $C_2$-$C_6$ alkyl;
17) $R^1$ is $C_2$-$C_6$ alkyl substituted one to five times with halo;
18) $R^1$ is $C_3$-$C_7$ cycloalkyl;
19) $R^1$ is $C_3$-$C_7$ cycloalkyl and X is —N=;
20) $R^1$ is cyclopropyl;
21) $R^2$ is hydrogen or $C_1$-$C_3$ n-alkyl;
22) $R^2$ is hydrogen or methyl;
23) $R^2$ is pyrazolylalkyl or N-substituted pyrazolylalkyl;
24) $R^2$ is pyrazol-4-yl-ethyl;
25) $R^2$ is 1-($C_1$-$C_3$ alkyl)pyrazol-4-yl-ethyl;
26) $R^2$ is cyclopropylmethyl;
27) $R^{3a}$, $R^{3b}$, and $R^{3c}$ if present, are each hydrogen;
28) One of $R^{3b}$ or $R^{3c}$ if present, is fluoro;
29) $R^4$ is hydrogen;
30) When X is —C($R^{3c}$)=, $R^4$ is methyl;
31) $R^5$ is hydrogen;
32) $R^5$ is methyl;
33) $R^{3a}$, $R^{3b}$, and $R^{3c}$ if present, are hydrogen or fluoro, provided no more than one of $R^{3a}$, $R^{3b}$, and $R^{3c}$ may be other than hydrogen;
34) $R^{3a}$, $R^{3b}$, and $R^{3c}$ if present, are hydrogen or fluoro, provided no more than one of $R^{3a}$, $R^{3b}$, and $R^{3c}$ may be other than hydrogen, and $R^4$ is hydrogen;
35) $R^{3a}$, $R^{3b}$ and $R^{3c}$ if present, are hydrogen or fluoro, provided no more than one of $R^{3a}$, $R^{3b}$, and $R^{3c}$ may be other than hydrogen, $R^4$ is hydrogen, and $R^5$ is hydrogen or methyl;
36) $R^{3b}$, and $R^{3c}$ if present, are hydrogen or fluoro, provided no more than one of $R^{3b}$ and $R^{3c}$ may be other than hydrogen, $R^4$ is hydrogen, and $R^5$ is hydrogen or methyl;
37) $R^2$ is hydrogen or methyl, $R^{3a}$, $R^{3b}$, and $R^{3c}$ if present, are each hydrogen or fluoro, provided no more than one of $R^{3a}$, $R^{3b}$, and $R^{3c}$ may be other than hydrogen, $R^4$ is hydrogen, and $R^5$ is hydrogen or methyl;
38) $R^1$ is mono-, di-, or tri-substituted phenyl wherein the substituents are independently selected from halo, $C_1$-$C_2$ alkoxy, trifluoromethyl, trifluoromethoxy, and trifluoroethoxy, $R^2$ is hydrogen or methyl, $R^{3a}$, $R^{3b}$, and $R^{3c}$ if present, are each hydrogen or fluoro, provided no more than one of $R^{3a}$, $R^{3b}$, and $R^{3c}$ may be other than hydrogen, $R^4$ is hydrogen, and $R^5$ is hydrogen or methyl;
39) $R^1$ is mono-, di-, or tri-substituted phenyl wherein the substituents are independently selected from halo, $R^2$ is hydrogen or methyl, $R^{3a}$, $R^{3b}$, and $R^{3c}$ if present, are each hydrogen or fluoro, provided no more than one of $R^{3a}$, $R^{3b}$, and $R^{3c}$ may be other than hydrogen, $R^4$ is hydrogen, and $R^5$ is hydrogen or methyl;
40) $R^1$ is a substituted or unsubstituted heterocycle selected from the group consisting of pyridinyl, indolyl, benzofuranyl, furanyl, thiophenyl, benzodioxolyl, and thiazolidinyl, $R^2$ is hydrogen or methyl, $R^{3a}$, $R^{3b}$, and $R^{3c}$ if present, are each hydrogen or fluoro, provided no more than one of $R^{3a}$, $R^{3b}$, and $R^{3c}$ may be other than hydrogen, $R^4$ is hydrogen, and $R^5$ is hydrogen or methyl;
41) $R^1$ is a substituted or unsubstituted heterocycle selected from the group consisting of pyridinyl, thiophenyl, and furanyl, $R^2$ is hydrogen or methyl, $R^{3a}$, $R^{3b}$, and $R^{3c}$ if present, are each hydrogen or fluoro, provided no more than one of $R^{3a}$, $R^{3b}$, and $R^{3c}$ may be other than hydrogen, $R^4$ is hydrogen, and $R^5$ is hydrogen or methyl;

It will be understood that the above classes may be combined to form additional preferred classes, as for example the combination of preferred selections for two or more substituents. Illustrative examples of combinations of preferred classes forming additional preferred classes are:

42) the combination of any one of preferred classes 1) through 20) with any one of preferred classes 21) through 26);
43) the combination of any one of preferred class 42) with preferred class 27) or 28);
44) the combination of any one of preferred classes 42) or 43) with preferred class 29) or 30);
45) the combination of any one of preferred classes 42), 43), or 44) with preferred class 31) or 32);

The compounds of the present invention may be synthesized through a number of alternative routes. Schemes 1-7 relate to the synthesis of compounds wherein X is —C($R^{3c}$)=. Schemes 8 and 9 relate to the synthesis of compounds wherein X is —N=. Suitable reaction conditions for the steps of these schemes are well known in the art and appropriate substitutions of solvents and co-reagents are within the skill of the art. Likewise, it will be appreciated by those skilled in the art that synthetic intermediates may by isolated and/or purified by various well known techniques as needed or desired, and that frequently, it will be possible to use various intermediates directly in subsequent synthetic steps with little or no purification. All substituents, unless otherwise indicated, are as previously defined, and all reagents are well known and appreciated in the art.

Scheme 1:

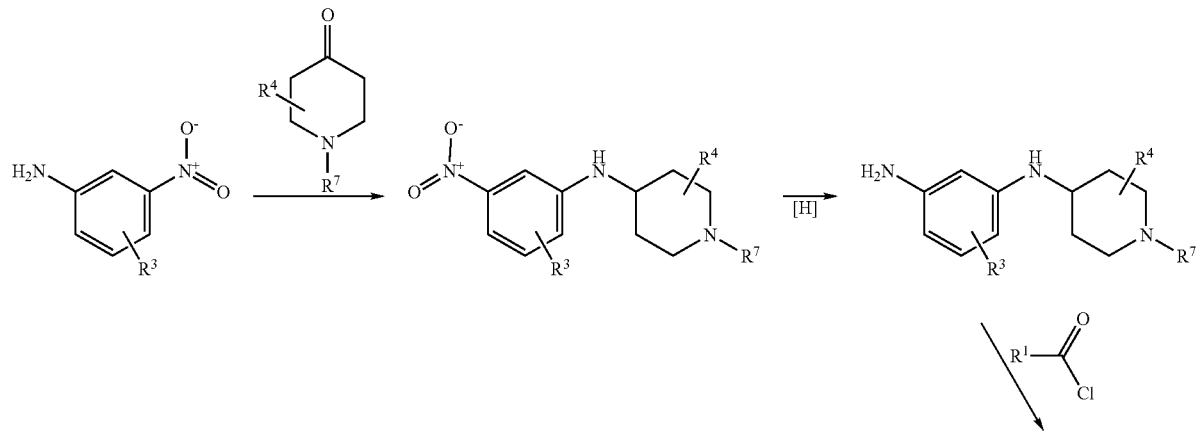

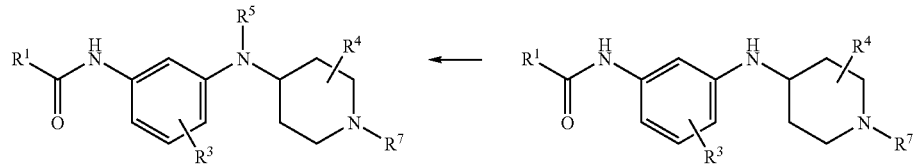

Compounds of the present invention wherein X is —CH= can be synthesized by methods according to Scheme 1, above, wherein $R^7$ is $C_1$-$C_3$ n-alkyl, $C_3$-$C_6$ cycloalkyl-$C_1$-$C_3$ alkyl, or a group of formula II, above, or a suitable nitrogen protecting group. The scheme comprises a reductive amination of an optionally $R^3$-substituted 3-aminonitrobenzene with the appropriate piperidin-4-one reagent, followed by reduction of the nitro group, and finally acylation of the primary amine with the appropriate $R^1$-acylchloride. Optionally, another reductive amination can then be done to obtain compounds wherein $R^5$ is other than hydrogen. Where $R^7$ is a protecting group, removal of the protecting group provides compounds of the present invention wherein $R^2$ is hydrogen. Further compounds wherein $R^2$ is other than hydrogen can then be made in a straight forward manner by alkylation of the piperidinyl nitrogen.

Reductive amination of 3-aminonitrobenzene with the appropriate piperidin-4-one reagent can be done in an inert solvent like dichloromethane, THF, toluene, or the like, at temperatures typically between about 0-40° C. in the presence of a borohydride such as sodium borohydride, sodium triacetoxyborohydride, sodium cyanoborohydride, or the like. Preferably, the reaction is performed in dichloromethane at ambient temperature in the presence of sodium triacetoxyborohydride. Reduction of the nitro function by catalytic hydrogenation in the presence of Pd/C is performed in an appropriate solvent, such as methanol, ethanol, isopropanol, or the like, at temperatures typically between about 20-40° C. Preferably, the hydrogenation is performed in methanol at ambient temperature. Finally, the acylation of the primary amine is run with an excess of the acid chloride, typically between about 1.1-1.3 equivalents, in the presence of an organic base, such as triethylamine, Hunig's base, or the like, in an appropriate solvent such as THF, $CH_2Cl_2$, diethyl ether, diisopropyl ether, methyl tert-butyl ether, dioxane, DMF, toluene, ethylacetate, acetone, or the like, at temperatures typically between about 0-40° C. Preferably, the acylation is performed in THF, acetone or ethyl acetate with 1.1 equivalent of the acid chloride at ambient temperature in presence of 2.2 equivalents of triethylamine.

Compounds wherein $R^5$ is $C_1$-$C_3$ alkyl can by made by reductive amination with the appropriate aldehyde, in the presence of an organic acid and a suitable borohydride. Preferably, this second amination is performed in methanol, with acetic acid and sodium cyanoborohydride at ambient temperature. Compounds wherein $R^5$ is $C_3$-$C_6$ cycloalkylcarbonyl can by made by reaction with the appropriate cycloalkylcarbonyl chloride reagent under similar acylation conditions as described above.

Scheme 2:

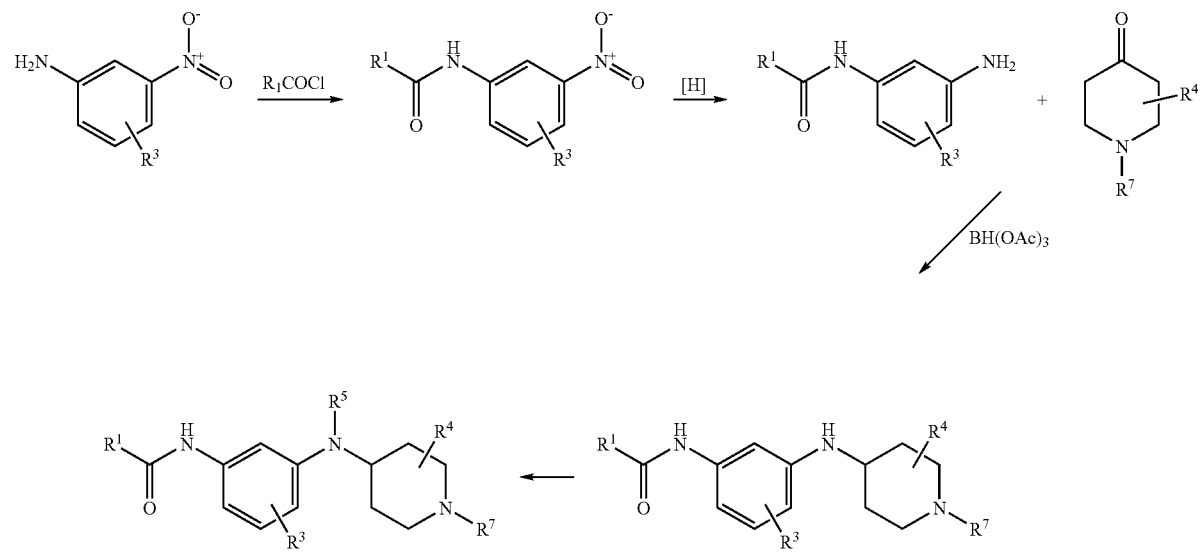

Alternatively, compounds of the present invention wherein X is —CH= can be synthesized by methods according to Scheme 2, above, wherein the condensation of the optionally R³-substituted 3-aminonitrobenzene with the appropriate R¹-acylchloride is conducted first, followed by reduction of the nitro group and reductive amination with the appropriate piperidin-4-one reagent. As with Scheme 1, compounds wherein R⁵ is other than hydrogen may be obtained through another reductive amination at the linker nitrogen. Also as with Scheme 1, where —R⁷ is a protecting group, removal of the protecting group provides compounds of the present invention wherein R² is hydrogen. Further compounds wherein R² is other than hydrogen can then be made in a straightforward manner by alkylation of the piperidinyl nitrogen.

Typically, combine the optionally R³-substituted 3-aminonitrobenzene with an appropriate solvent, such as dioxane, pyridine, THF, N,N-dimethylacetamide, or the like. Treat the mixture with the appropriate acid chloride (1.0 to 2.0 equivalents). Stir the reaction for between about 2-48 hr. at between about 0-40° C., say room temperature for about 16 hr. Transfer the reaction mixture into ethyl acetate or other suitable solvent, and wash successively with aqueous HCL (1N), aqueous NaOH (1N), saturated aqueous NaCl. Normal workup procedures on the organic layer provide the benzamide intermediate.

Add the benzamide intermediate to a warm solution (about 35-70° C., say about 55° C.) of SnCl₂.2H₂O in ethanol. Add concentrated HCl and then stir and heat the mixture at between about 50-65° C., say about 60° C., for between about 20-60 min., say about 30 min. Cool the reaction mixture and then basify the mixture to about pH 14 with aqueous NaOH. Extract the product with an appropriate solvent, such as ethyl acetate or the like. Normal workup procedures on the combined organic layers provide the aminobenzamide intermediate.

Stir a mixture of the aminobenzamide intermediate, N-protected-4-piperidone, and powdered molecular sieve (4 A), in an appropriate solvent such as THF, dichloroethane, methylene chloride, or the like, under an inert atmosphere. Add glacial acetic acid. After between about 1-8 hr., say about 1 hr., add NaBH(OC(O)CH₃)₃. Allow the mixture to react for about 8-24 hr., at about 0° C.-40° C., say about room temperature. Pour the reaction mixture into a suitable solvent such as methylene chloride, ethyl acetate, or the like, and wash with aqueous NaOH. Normal workup procedures on the organic layer provide the desired piperidinylbenzamide.

As with Scheme 1, the linker nitrogen can optionally be substituted if desired to provide compounds wherein R⁵ is other than hydrogen.

Scheme 3:

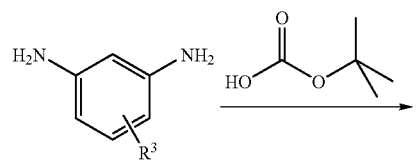

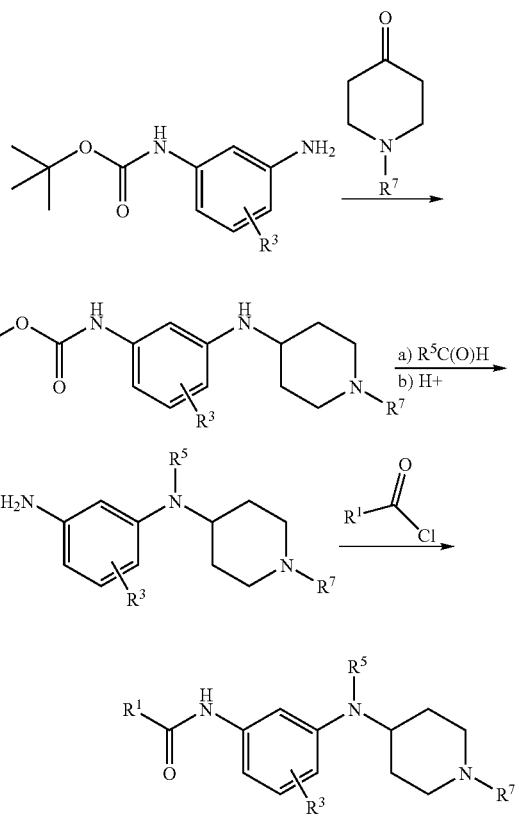

Compounds of the present invention wherein X is —CH= may also be synthesized by methods according to Scheme 3, above, comprising protection of one amino group of 1,3 diaminobenzene, reductive amination with an appropriate piperidin-4-one reagent, deprotection, and finally acylation of the primary amine with an appropriate R¹-acylchloride. Reaction conditions are similar to those in Schemes 1 and 2, above. Note also that substitution of the linker nitrogen may be performed before or after the acylation step, as desired.

Scheme 4:

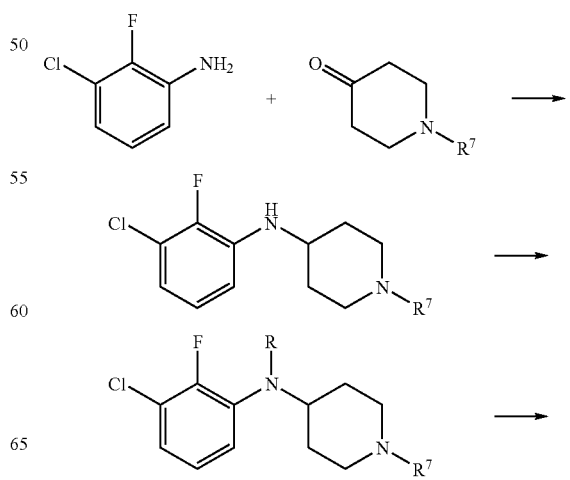

15

-continued

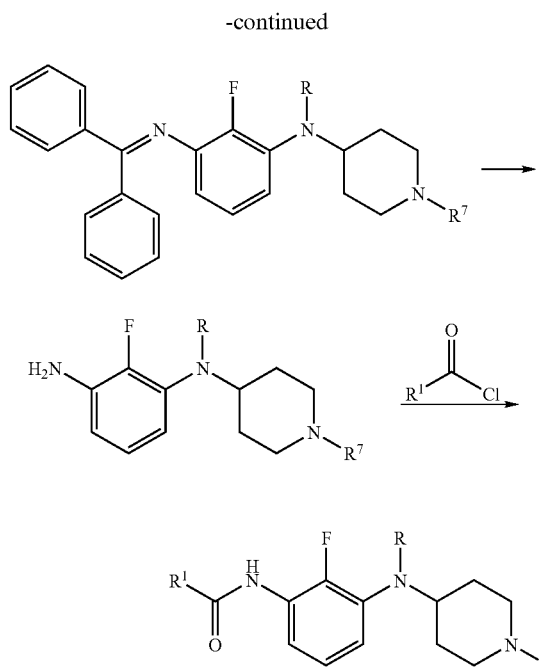

Compounds of the present invention wherein $R^{3c}$ is fluoro can be synthesized as shown in Scheme 4. An initial reductive amination of 3-amino-1-chloro-2-fluorobenzene with an appropriately substituted 4-piperidone is followed by conversion of the chloro group to an amino group, and subsequent condensation with the appropriate $R^1$-acylhalide compound. Reaction conditions are similar to those in Schemes 1-3, above. Note also that substitution of the linker nitrogen may be performed before or after the acylation step, as desired.

Scheme 5:

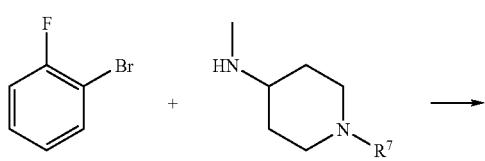

Scheme 6:

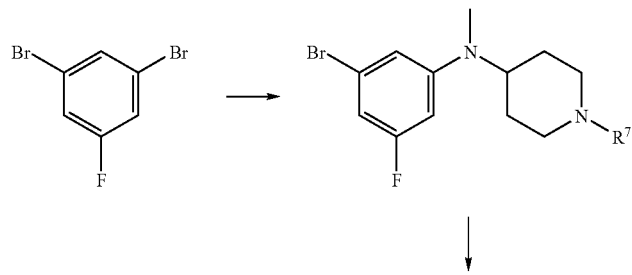

16

-continued

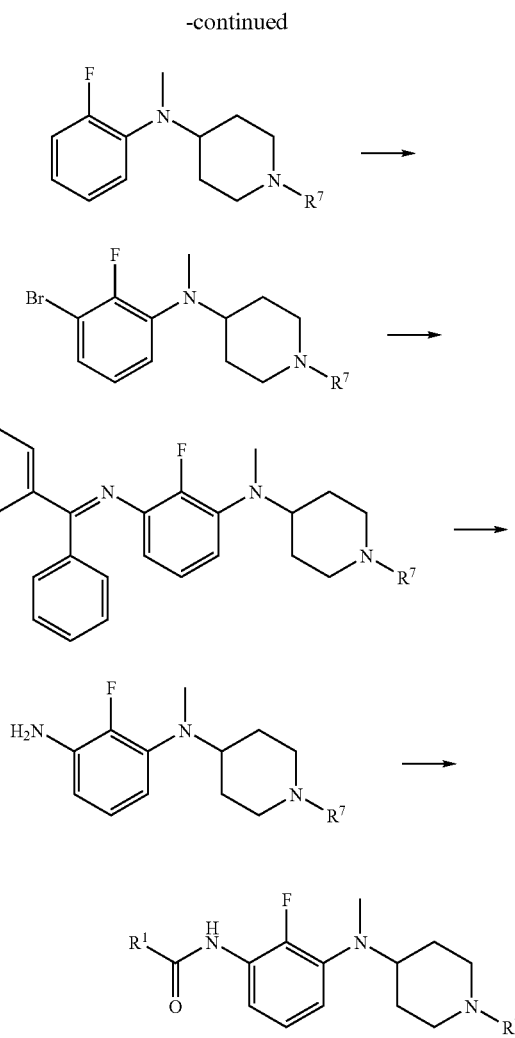

Compounds wherein $R^{3c}$ is fluoro and $R^5$ is $C_1$-$C_3$ alkyl can be synthesized as shown in Scheme 5 showing $R^5$=methyl as an example. An initial condensation of 1-bromo-2-fluorobenzene with an appropriately substituted 4-aminopiperidine is followed by halogenation of the benzyl ring, conversion of the halo group to an amino group, and subsequent condensation with the appropriate $R^1$-acylhalide compound.

-continued

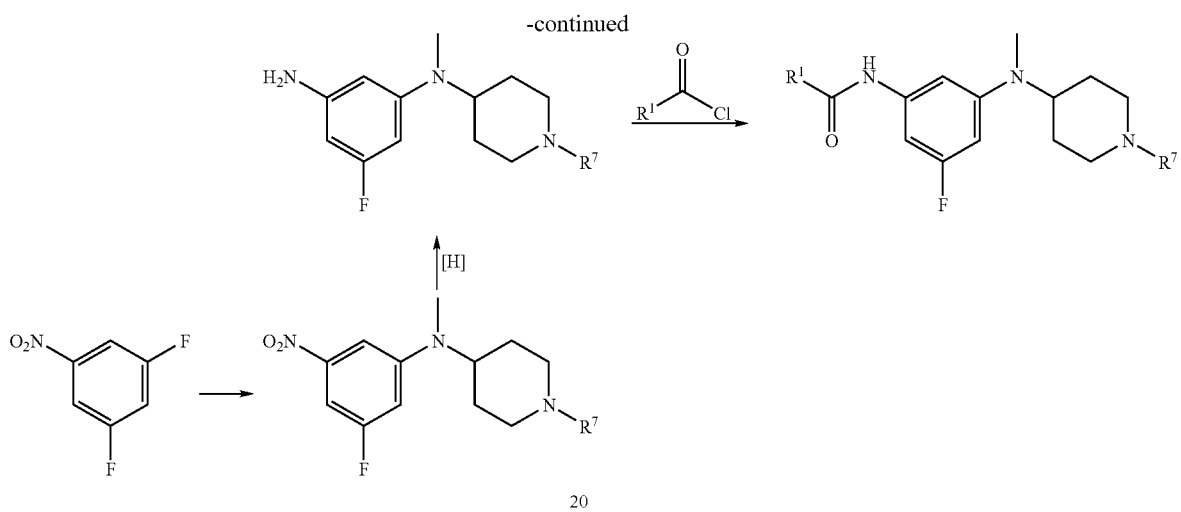

Compounds of the present invention wherein $R^{3b}$ is fluoro and $R^5$ is $C_1$-$C_3$ alkyl can be synthesized as shown in Scheme 6 showing $R^5$=methyl as an example. An initial condensation of 1,3-dibromo-5-fluorobenzene with an appropriately substituted 4-aminopiperidine is followed by conversion of the remaining bromo group to an amino group, and subsequent condensation with the appropriate $R^1$-acylhalide compound. Alternatively, 1,3-difluoro-5-nitrobenzene can be used in the initial condensation with an appropriately substituted 4-aminopiperidine, followed by reduction of the nitro group to an amino group, and subsequent condensation with the appropriate $R^1$-acylhalide compound.

Typically the 1,3-dibromo-5-fluorobenzene dissolved in an appropriate solvent, such as toluene, benzene, or the like, is combined with methyl-(1-methylpiperidin-4-yl)amine, sodium t-butoxide, $Pd_2dba_3$, and BINAP, and heated, as for example, between 50° C. and 100° C., say about 80° C., for between about 1-3 hr., say about 2 hr. The reaction is quenched, as for example by addition of water or other suitable means. The (3-bromo-5-fluorophenyl)-methyl-(1-methylpiperidin-4-yl)-amine intermediate may be worked up by common procedures, as for example, solvent removal, extraction procedures, and/or further purification by chromatography, etc.

The (3-bromo-5-fluorophenyl)-methyl-(1-methylpiperidin-4-yl)-amine intermediate is then aminated at the benzo 3-position, as for example, by reacting the intermediate with BINAP, $Pd_2dba_3$, benzhydrylideneamine, and sodium t-butoxide, in a suitable solvent, such as toluene or the like, under an inert atmosphere for about 1-3 hr., say about 2 hr., at about 50° C. to 100° C., say about 80° C. The resulting intermediate is treated with 1M HCl or the like in a suitable solvent, such as THF at 0° C. to ambient temperature, preferably ambient temperature for 1-2 hours, say about 1 hr. The resulting intermediate, 5-fluoro-N-methyl-N-(1-methylpiperidin-4-yl)benzene-1,3-diamine may then be isolated and purified by common procedures such as, but not limited to, solvent removal, extraction and/or chromatography, etc.

Final compounds can then be synthesized by condensation with the $R^1$-acylchloride. Typically, the 5-fluoroaminobenzene intermediate is reacted with the appropriate $R^1$-acylchloride, in an appropriate solvent, such as dioxane, pyridine, DMF, or the like, at between ambient temperature and about 100° C., preferably between about 50-100° C., until the reaction is complete, as for example between about 1-4 hr., say about 2 hr. The reaction is then quenched by addition of water and the final product purified by normal work-up procedures.

Alternatively, the 5-fluoro-N-methyl-N-(1-methylpiperidin-4-yl)benzene-1,3-diamine intermediate may be prepared by reacting the 1,3-difluoro-5-nitro benzene with methyl-(1-methylpiperidin-4-yl)amine in the presence of sodium acetate in a suitable solvent, such as ethanol or the like, for between about 8-16 hr., say about 12 hr., at 80-120° C., say about 100° C. in a sealed tube. The reaction is then quenched by the addition of water or the like and the (3-fluoro-5-nitrophenyl)-methyl-(1-methylpiperidin-4-yl)amine intermediate is purified by normal work-up procedures. The nitro group is then reduced to an amino group, as for example, by treatment with iron and 1M HCl in a suitable solvent, such as methanol or the like, for between about 8 hr. to overnight, say about 16 hours, at between about 80-100° C., say about 100° C. The 5-fluoro-N-methyl-N-(1-methylpiperidin-4-yl)benzene-1,3-diamine intermediate may then be isolated and purified by common procedures.

Scheme 7:

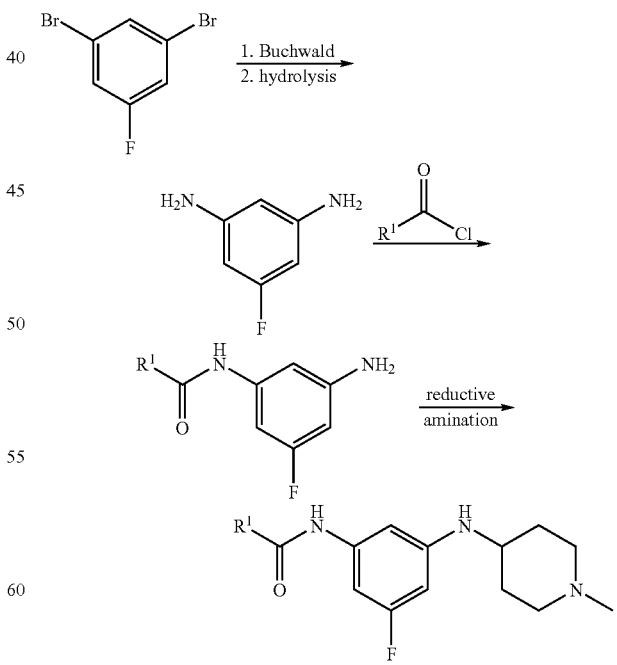

Compounds of the present invention wherein $R^{3b}$ is fluoro and $R^5$ is hydrogen can be synthesized as shown in Scheme 7, where 1,3-dibromo-5-fluorobenzene is converted to a 1,3- diamino compound, condensed with the appropriate $R^1$-acyl-halide compound, followed by reductive amination with an appropriately substituted 4-aminopiperidine.

Typically, 1,3-dibromo-5-fluorobenzene, benzophenone imine, $Pd_2(dba)_3$, BINAP and sodium t-butoxide are mixed in a suitable solvent, such as toluene, xylene, 1,4-dioxane, or the like, and heated, as for example between 60-130° C. for about 8-20 hr., say about 15 hr. The reaction is quenched with saturated $NaHCO_3$ solution extracted several times with an organic solvent, such as ethylacetate, methylene dichloride, or the like. The organic layers are combined and the solvent removed. The residue is dissolved in a suitable solvent, such as THF, ether, methanol, or the like, and aqueous HCl is added, as for example, between 1-6 N HCl, say about 5 N HCl. The reaction mixture is stirred for about 1-3 hr. at between about 0-60° C., say about ambient temperature. The reaction mixture is then diluted with dilute aqueous HCl and extracted with an ethyl acetate/hexanes solvent system, or equivalent. The organic layer is washed with dilute aqueous HCl and the aqueous layer is then basified with NaOH and extracted with an organic solvent such as methylene dichloride or the like. The extract is dried, filtered, concentrated, and further purified by chromatography to give the diamino intermediate.

A mixture of the diamino intermediate and the desired $R^1$-acylchloride in an appropriate solvent, such as dioxane, pyridine, THF, or DMF, with an appropriate tertiary amine, such as triethylamine, N-methylmorpholine, or diisopropyl-ethylamine is stirred at between about 0-40° C. until the reaction is complete, as for example, between about 2-20 hr., say about 12 hr. The reaction is then quenched by addition of dilute aqueous NaOH. Normal work up and purification procedures provides the amide intermediate. Sodium triacetoxyborohydride is then added to a mixture of the amide intermediate, the appropriate 1-substituted or N-protected 4-piperidone, acetic acid, and a molecular sieve (typically about 4 Å), in an appropriate solvent, such as THF, dichloroethane, methylene dichloride, or the like. The reaction mixture is stirred for about 8-20 hr., say about 12 hr., at about 0-40° C., say about ambient temperature. The reaction is then quenched with dilute aqueous NaOH, extracted with a suitable organic solvent, such as methylene dichloride, ethylacetate, or the like. The organic layer is dried, filtered, concentrated, and further purified, as for example, by chromatography, to provide the desired product. When $R^7$ is a protecting group, an appropriate unprotecting method is used to provide compounds wherein $R^2$ is hydrogen. If desired, the unsubstituted piperidinyl moiety can then be alkylated by common reductive alkylation methods to provide compounds having $R^2$ other than hydrogen.

Scheme 8:

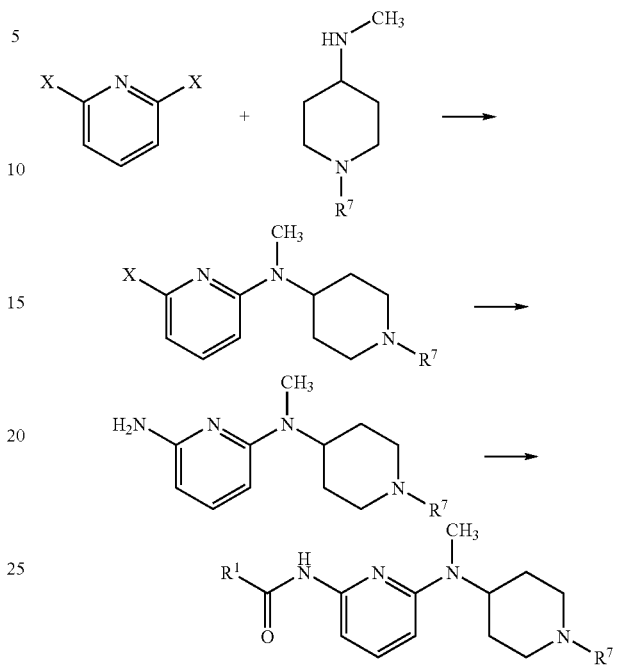

2,6-Dihalopyridine (X=Cl or Br) is alkylated with an appropriately substituted 4-(methylamino)piperidine in the presence of a base such as potassium carbonate, n-butyllithium, sodium hydride, etc. in DMF, acetonitrile, THF, or like solvent. Alternatively, the 2,6-dihalopyridine can be treated with BINAP (or other acceptable ligand), $Pd(OAc)_2$, the piperidine, and sodium tert-butoxide (or other suitable base) in toluene (or like solvent) to yield the intermediate 1-methyl-4-(N-(6-halopyridinyl)methylaminopiperidine.

The halopyridine is then treated with BINAP (or other acceptable ligand), $Pd(OAc)_2$, benzophenone imine (or other amine equivalent), and sodium tert-butoxide (or other suitable base) in toluene (or like solvent) to yield the intermediate substituted 4-(N-(6-aminopyridinyl)methylaminopiperidine. This amine is then acylated with a variety of acid chlorides in pyridine, THF, 1,4-dioxane, or like solvent to yield the final product. Similarly, compounds wherein $R^5$ is ethyl or propyl can be made using the appropriate 4-(ethylamino)piperidine or 4-(propylamino)piperidine.

Scheme 9:

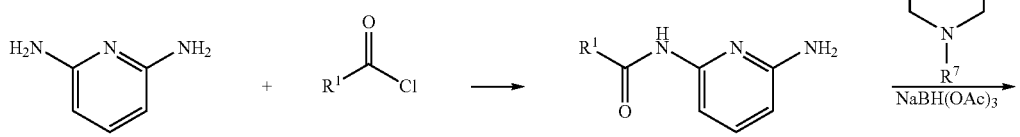

-continued

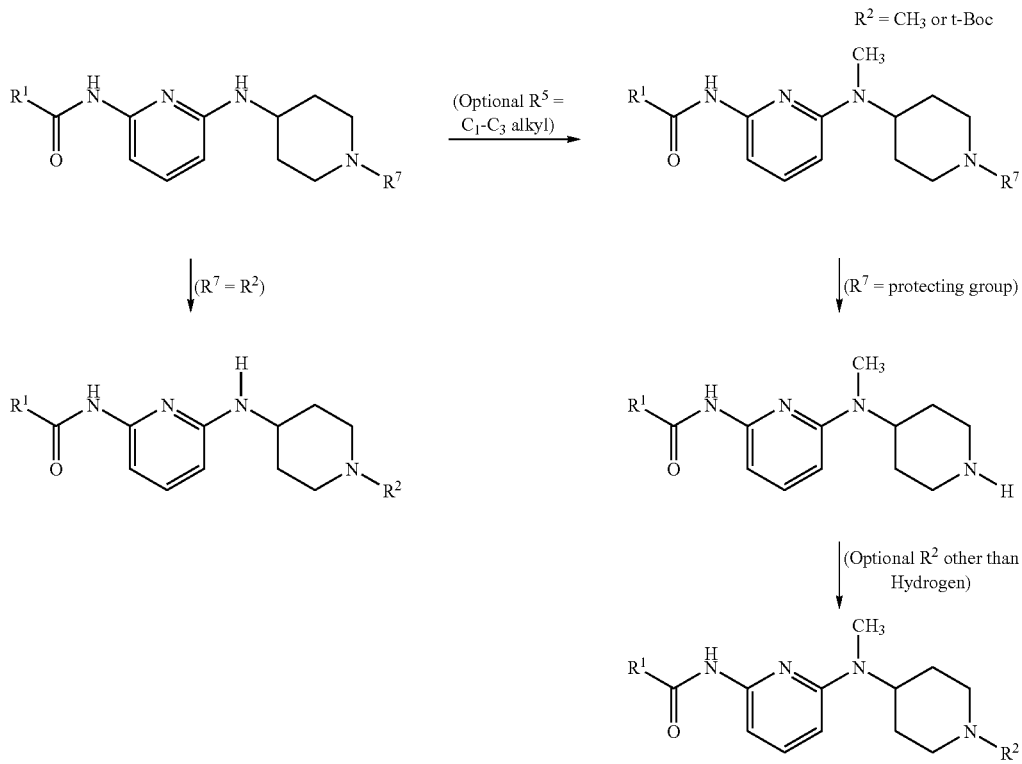

Typically, a mixture of $R^1$-acyl chloride and 2,6-diaminopyridine in a suitable solvent, such as dioxane, THF, DMF, or the like, is stirred at about ambient temperature to about 100° C. for between about 2-20 hr., say about 12 hr. Normal work procedures, such as extraction, filtration, and/or chromatography, provide the N-(6-aminopyridin-2-yl)amide intermediate.

Sodium triacetoxyborohydride is then added to a mixture of the above intermediate with the appropriate 1-substituted 4-piperidone, acetic acid, and a molecular sieve, in an appropriate solvent, such as THF, dichloroethane, methylene dichloride, or the like. The reaction mixture is stirred at between about 0-40° C., say about ambient temperature, for about 8-20 hr., about 12 hr. Typically another aliquot of the piperidone reagent and sodium triacetoxyborohydride is added and allowed to react with any remaining N-(6-aminopyridin-2-yl)amide intermediate. The reaction is then quenched with dilute aqueous NaOH. Routine work-up and purification procedures provide the N-(5-piperidin-4-ylamino)amide compound. When $R^7$ is the desired $R^2$ moiety, then normal final purification procedures are used to provide the end product. When $R^7$ is a protecting group, the protecting group is removed by appropriate procedures to provide compounds wherein $R^2$ is hydrogen. These compounds may, if desired, then be further alkylated by well know procedures to provide end products wherein $R^2$ is other than hydrogen.

The following Preparations and Examples are provided to better elucidate the practice of the present invention and should not be interpreted in any way so as to limit the scope thereof.

PREPARATIONS

Preparation 1

N-(3-Aminophenyl)-2-chloro-4-fluorobenzamide

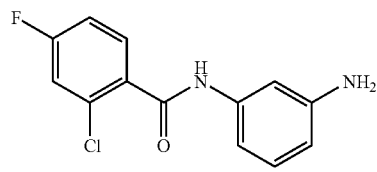

Combine 3-nitroaniline (3.0 g, 21.7 mmol), dichloromethane (100 mL), pyridine (2.11 mL, 26.0 mmol) and 2-chloro-4-fluorobenzoyl chloride (3.07 mL, 23.9 mmol). Stir at room temperature overnight. Filter the white precipitate, rinse with ether (2×10 mL), and dry under vacuum to provide 2-chloro-4-fluoro-N-(3-nitrophenyl)benzamide (4.92 g, 77%). Combine the 2-chloro-4-fluoro-N-(3-nitrophenyl)benzamide (4.92 g, 16.7 mmol) with ethanol (150 mL), $SnCl_2$-2H2O (18.9 g, 83.6 mmol) and concentrated hydrochloric acid (8.24 mL, 83.6 mmol). Stir at reflux under a nitrogen atmosphere for 2 hr. Neutralize with ammonium hydroxide (15 mL). Filter through Celite®, wash with dichloromethane (2×15 mL), separate the filtrate, extract with dichloromethane (2×80 mL), and dry the combined organic layers over magnesium sulfate. Filter and concentrate to dryness to provide the title intermediate as an off-white solid (3.04 g, 69%): mass spectrum (ion spray): m/z=265.0 (M+1);

¹H NMR (DMSO-d₆): 10.16 (bs, N—H), 7.60 (dd, J=6.2 Hz, 8.6 Hz, 1H), 7.54 (dd, J=2.5 Hz, 9.0 Hz, 1H), 7.30 (td, J=2.5 Hz, 8.5 Hz, 1H), 7.04 (t, J=2.0 Hz, 1H), 6.93 (t, J=8.0 Hz, 1H), 6.74 (bd, J=7.9 Hz, 1H), 6.29 (dd, J=2.2 Hz, 7.9 Hz, 1H), 5.10 (bs, 2H).

Preparation 2

N-(3-Aminophenyl)-2-chloro-6-fluorobenzamide

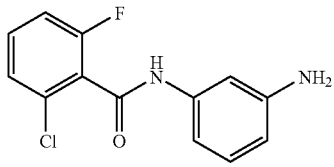

Using a method similar to Preparation 1, using 2-chloro-6-fluorobenzoyl chloride (1.0 g, 3.39 mmol) gives the title intermediate (820 mg, 91%): mass spectrum (ion spray): m/z=265.1 (M+1); ¹H NMR (DMSO-d₆): 10.42 (bs, N—H), 7.50 (td, J=6.2 Hz, 8.2 Hz, 1H), 7.40 (d, J=8.0 Hz, 1H), 7.34 (t, J=8.7 Hz, 1H), 7.03 (t, J=2.1 Hz, 1H), 6.94 (t, J=8.0 Hz, 1H), 6.71 (dd, J=2.1 Hz, 8.0 Hz, 1H), 6.31 (dd, J=2.1 Hz, 8.0 Hz, 1H), 5.13 (bs, 2H).

Preparation 3

N-(3-Aminophenyl)-2,6-difluorobenzamide

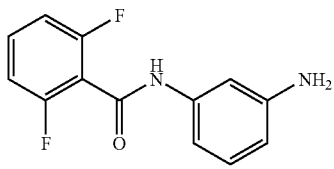

Using a method similar to Preparation 1, using 2,6-difluorobenzoyl chloride (1.0 g, 3.59 mmol) gives the title intermediate (723 mg, 81%): mass spectrum (ion spray): m/z=248.9 (M+1); ¹H NMR (DMSO-d₆): 10.44 (bs, N—H), 7.58-7.50 (m, 1H), 7.24-7.17 (m, 2H), 7.02 (t, J=2.0 Hz, 1H), 6.94 (t, J=8.0 Hz, 1H), 6.72 (bd, J=8.0 Hz, 1H), 6.31 (dd, J=2.1 Hz, 8.0 Hz, 1H), 5.14 (bs, 2H).

Preparation 4

N-(3-Aminophenyl)-2,4-difluorobenzamide

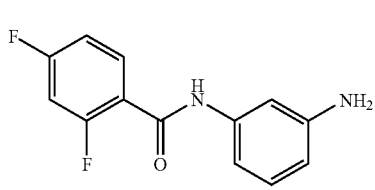

Using a method similar to Preparation 1, using 2,4-difluorobenzoyl chloride (1.0 g, 3.59 mmol) gives the title intermediate (664 mg, 74%): mass spectrum (ion spray): m/z=248.9 (M+1); ¹H NMR (DMSO-d₆): 10.08 (bs, N—H), 7.68 (dd, J=8.1 Hz, 15.1 Hz, 1H), 7.38 (td, J=2.5 Hz, 10.2 Hz, 1H), 7.18 (td, J=2.5 Hz, 8.5 Hz, 1H), 7.01 (bs, 1H), 6.93 (t, J=7.8 Hz, 1H), 6.76 (bd, J=7.8 Hz, 1H), 6.29 (dd, J=1.9 Hz, 8.0 Hz, 1H), 5.10 (bs, 2H).

Preparation 5

N-(3-Aminophenyl)-2,4,6-trifluorobenzamide

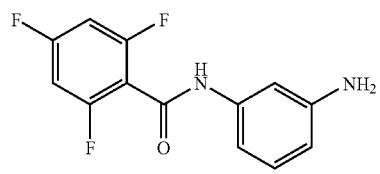

Using a method similar to Preparation 1, using 2,4,6-trifluorobenzoyl chloride (1.0 g, 3.37 mmol) gives the title compound (485 mg, 54%): mass spectrum (ion spray): m/z=266.9 (M+1); ¹H NMR (DMSO-d₆): 10.43 (bs, N—H), 7.34 (t, J=8.5 Hz, 2H), 6.99 (d, J=1.5 Hz, 1H), 6.94 (t, J=7.9 Hz, 1H), 6.10 (d, J=8.2 Hz, 1H), 6.31 (d, J=8.2 Hz, 1H), 5.15 (bs, 2H).

Preparation 6

N-(3-Aminophenyl)-2-bromobenzamide

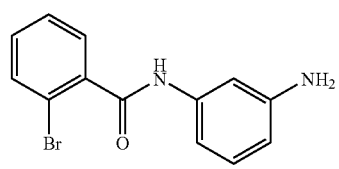

Using a method similar to Preparation 1, using 2-bromobenzoyl chloride (1.0 g, 3.11 mmol) gives the title intermediate (744 mg, 82%): mass spectrum (ion spray): m/z=293.0 (M+1); ¹H NMR (DMSO-d₆): 10.14 (bs, N—H), 7.68 (d, J=8.0 Hz, 1H), 7.50-7.43 (m, 2H), 7.37 (td, J=2.5 Hz, 7.3 Hz, 1H), 7.07 (bs, 1H), 6.92 (t, J=7.8 Hz, 1H), 6.74 (bd, J=8.0 Hz, 1H), 6.29 (bd, J=8.0 Hz, 1H), 5.10 (bs, 2H).

Preparation 7

N-(3-Aminophenyl)-2-chlorobenzamide

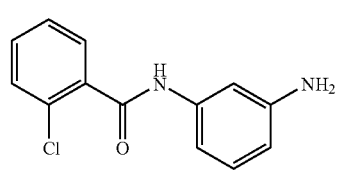

Using a method similar to Preparation 1, using 2-chlorobenzoyl chloride (4.0 g, 14.5 mmol) gives the title intermediate (2.8 g, 78%): mass spectrum (ion spray): m/z=247.0 (M+1); ¹H NMR (DMSO-d₆): 10.16 (bs, N—H), 7.54-7.39

(m, 4H), 7.06 (bs, 1H), 6.92 (t, J=8.0 Hz, 1H), 6.74 (bd, J=8.0 Hz, 1H), 6.28 (bd, J=8.3 Hz, 1H), 5.10 (bs, 2H).

Preparation 8

N-(3-Aminophenyl)-2-trifluoromethoxybenzamide

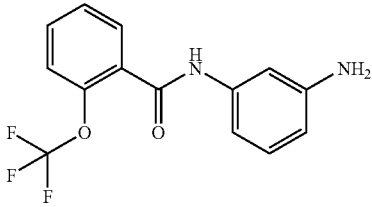

Using a method similar to Preparation 1, using 2-trifluoromethoxybenzoyl chloride (300 mg, 1.01 mmol) gives the title intermediate (274 mg, 69%) as a white foam: mass spectrum (ion spray): m/z=394.2 (M+1); $^1$H NMR (CDCl$_3$): 8.18 (bs, N—H), 8.07 (d, J=7.5 Hz, 1H), 7.55 (t, J=7.7 Hz, 1H), 7.45 (t, J=7.5 Hz, 1H), 7.34 (d, J=8.0 Hz, 1H), 7.21 (s, 1H), 7.13 (t, J=8.0 Hz, 1H), 6.68 (d, J=7.7 Hz, 1H), 6.41 (d, J=8.0 Hz, 1H), 3.70-3.63 (bm, 1H), 3.38-3.28 (bm, 1H), 3.85-3.77 (bm, 2H), 2.30 (s, 3H), 2.21-2.04 (bm, 4H), 1.57-1.46 (bm, 2H).

Preparation 9

(3-(1-Methylpiperidin-4-ylamino)phenyl)carbamic acid tert-butyl ester

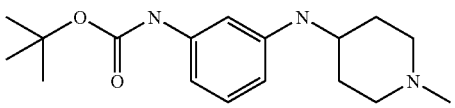

Add a solution of di-tert-butyl dicarbonate (5.04 g, 23.11 mmol) in chloroform (100 mL+100 mL rinse) to a solution of 1,3-phenylenediamine (5.0 g, 46.23 mmol) in chloroform (100 mL). Stir at room temperature overnight. Wash with sodium hydroxide (1N aq., 200 mL) and separate the organic layer. Purify through flash chromatography (ethylacetate/hexanes 1/4 to 1/1) to provide (3-amino-phenyl)-carbamic acid tert-butyl ester (4.17 g, 87%).

Combine (3-aminophenyl)carbamic acid tert-butyl ester (0.156 g, 0.756 mmol), 1-methylpiperidin-4-one (0.093 mL, 0.756 mmol), sodium triacetoxyborohydride (208 mg, 0.982 mmol), acetic acid (0.043 mL, 0.756 mmol) and dichloromethane (8 mL). Stir at room temperature overnight. Dilute with dichloromethane (5 mL) and wash twice with sodium hydroxide (10 mL 1N aq.). Combine the organic layers and wash with saturated aqueous NaCl (10 mL). Dry over magnesium sulfate, filter under reduced pressure and concentrate to dryness. Purify by flash chromatography on a Biotage® silica cartridge eluting with a 20/1 mixture of dichloromethane and 2N ammonia in methanol to give the free base of the title compound. Dissolve the residue in diethyl ether and treat with ethereal hydrogen chloride. Triturate the resulting gum with ether to give the title compound as a white solid: mp 124-5° C.; mass spectrum (ion spray): m/z=306.2 (M+1), $^1$H NMR (CDCl$_3$): 7.06 (t, J=8.0 Hz, 1H), 6.86 (bs, 1H), 6.51-6.48 (m, 1H), 6.42 (bs, 1H), 6.30-6.27 (m, 1H), 3.60 (bs, 1H), 3.30 (bs, 1H), 2.80 (bd, J=11.8 Hz, 2H), 2.31 (s, 3H), 2.19-2.02 (m, 4H), 1.89 (bs, 2H), 1.52 (s, 9H).

Preparation 10

(3-(Methyl-(1-methylpiperidin-4-yl)amino)phenyl) carbamic acid tert-butyl ester

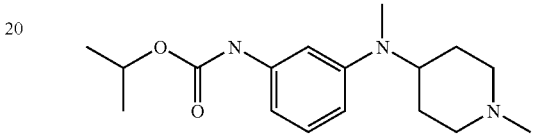

Combine (3-(1-methylpiperidin-4-ylamino)phenyl)carbamic acid tert-butyl ester (Preparation 9, 1.15 g, 3.77 mmol), methanol (15 mL) and formaldehyde (37% aq., 0.92 mL, 11.3 mmol). Stir at room temperature for 45 min. Cool to 0° C. Add acetic acid (0.22 mL, 3.77 mmol) and sodium cyanoborohydride (414 mg, 6.59 mmol). Stir at room temperature overnight. Concentrate to dryness. Dissolve the residue in a 2/1 mixture of ethyl acetate and hexanes (20 mL) and wash with sodium hydroxide (1N aq., 2×20 mL). Separate the organic layer and dry over magnesium sulfate. Filter and concentrate under reduced pressure. Purify through flash chromatography eluting with a 20/1 mixture of dichloromethane and 2M ammonia in methanol to provide the title compound (990 mg, 82%): mass spectrum (ion spray): m/z=320.3 (M+1).

Preparation 11

1-methyl-4-(N-(3-aminophenyl)-N-methylamino) piperidine trihydrochloride

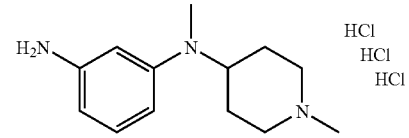

Combine acetyl chloride (5 mL) with dried methanol (10 mL) at 0° C. under nitrogen atmosphere. Stir for 1 hr. at 0° C. Add a solution of (3-(methyl-(1-methylpiperidin-4-yl) amino)phenyl)carbamic acid tert-butyl ester (Preparation 10, 990 mg, 3.1 mmol) in methanol (2 mL). Stir overnight. Concentrate under reduced pressure. Triture with diethyl ether (1 mL) to provide the title intermediate (671 mg, 66%): mass spectrum (free base, ion spray): m/z=220.3 (M+1). Analysis calculated for $C_{13}H_{24}Cl_3N_3Cl_3$: C, 47.50; H, 7.36; N, 12.78. Found: C, 47.28; H, 7.28; N, 12.46.

Preparation 12

4-(2-Hydroxyethyl)-1-isopropyl-1H-pyrazole

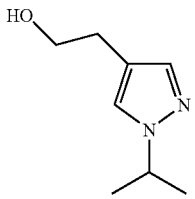

Combine 2,3-dihydrofuran (25 mL, 0.33 mol) and triethylorthoformate (93.3 mL, 0.56 mol) and then slowly add boron trifluoride diethyl etherate (2.0 mL, 0.017 mol) while stirring rapidly. Allow the reaction to continue for 18 hr. Distill the reaction at 60° C. under 8 mm Hg vacuum to remove excess 2,3-dihydrofuran and triethylorthoformate. Heat a portion of the remaining residue (10 g, 45 mmol) at reflux in 1 N HCl with isopropyl hydrazine (3.4 g, 45 mmol). After 2 hr, the temperature is reduced to 80° C. and the reaction is stirred for 18 hr. After cooling to room temperature, the mixture is basified with 1 N NaOH to a pH>12 and diluted with CH2Cl2. Separate and extract the aqueous layer with $CH_2Cl_2$ (two times), combine organic layers, dry over $MgSO_4$, and concentrate. Chromatography on silica gel, eluting with a gradient of 0-10% (2M $NH_3$ in methanol) in $CH_2Cl_2$ provides the title intermediate as a brown solid (3.6 g, 52%). Mass spectrum (ion spray): m/z=155.2 (M+1); $^1$H NMR (DMSO, ppm) 7.52 (s, 1H), 7.24 (s, 1H), 4.59 (t, J=5.5, 10.6 Hz, 1H), 4.39 (m, 1H), 3.51 (m, 2H), 2.51 (m, 2H), 1.38 (s, 3H), 1.35 (s, 3H)

Preparation 13

2-Chloro-4-fluoro-N-(4-fluoro-3-nitrophenyl)benzamide

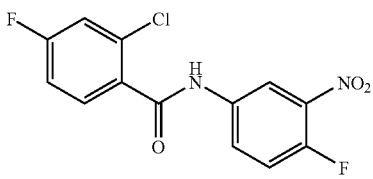

Combine 4-fluoro-3-nitroaniline (1.0 g, 6.4 mmol) with dioxane (20 mL). Treat mixture with 2-chloro-4-fluorobenzoyl chloride (1.6 g, 8.3 mmol). Stir the reaction overnight at room temperature. Transfer the reaction mixture into ethyl acetate (220 mL), then wash successively with aqueous HCl (1N, 50 mL), aqueous NaOH (1N, 50 mL), saturated aqueous NaCl (50 mL). Dry the organic layer over anhydrous sodium sulfate, then evaporate the solvent under reduced pressure. Further purify the residue by chromatography on silica gel, using a gradient of 10-30% ethyl acetate in hexanes to obtain the title intermediate (1.7 g, 85% yield): mass spectrum (ion spray): m/z=313.0 (M+1).

Preparation 14

N-(3-Amino-4-fluorophenyl)-2-chloro-4-fluorobenzamide

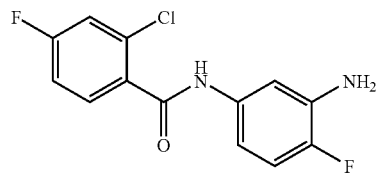

Add 2-chloro-4-fluoro-N-(4-fluoro-3-nitrophenyl)benzamide (Preparation 11, 1 g, 3.2 mmol) to a warm solution (55° C.) of $SnCl_2.2H_2O$ (3.6 g, 16 mmol) in ethanol (25 mL). Add concentrated HCl (25 mL). Stir and heat the mixture at 60° C. for 30 min. Cool and then basicify the mixture to pH 14 with aqueous NaOH. Extract the product three times with ethyl acetate (3×150 mL). Combine the organic layers and dry over anhydrous sodium sulfate. Evaporate the solvent under reduced pressure. Further purify the residue by chromatography on silica gel, using a gradient of 10-50% ethyl acetate in hexanes to obtain the title intermediate (800 mg, 89% yield): mass spectrum (ion spray): m/z=283.0 (M+1).

Preparation 15

2,4-Difluoro-N-(4-fluoro-3-nitrophenyl)benzamide

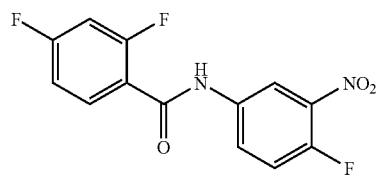

Using a method similar to Preparation 13, using 4-fluoro-3-nitroaniline (1.0 g, 6.4 mmol), dioxane (20 mL), and 2,4-difluorobenzoyl chloride (1.46 g, 8.3 mmol) gives the title intermediate (1.6 g, 84% yield): mass spectrum (ion spray): m/z=297.0 (M+1).

Preparation 16

2,4-Difluoro-N-(3-amino-4-fluorophenyl)benzamide

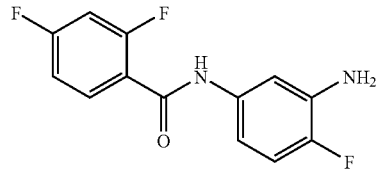

Using a method similar to Preparation 14 using 2,4-Difluoro-N-(4-fluoro-3-nitrophenyl)benzamide (Preparation 13) (1.0 g, 3.38 mmol), $SnCl_2.2H_2O$ (3.8 g, 16.9 mmol), ethanol (25 mL), and concentrated HCl (25 mL), gives the title intermediate (803 mg, 89% yield): mass spectrum (ion spray): m/z=267.0 (M+1).

Preparation 17

1-Methyl-4-(3-nitrophenylamino)piperidine

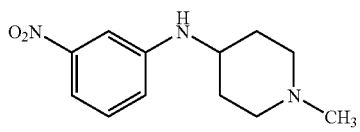

Combine 3-nitroaniline (25.0 g, 180.0 mmol), 1-methyl-4-piperidone (40.9 mL, 360.0 mmol), and acetic acid (21.7 mL, 360.0 mmol) in 350 mL of dichloroethane. Stir at room temperature for 0.5 hr. Add sodium triacetoxyborohydride (76.4 g, 360.0 mmol) in several portions, and stir the reaction mixture at room temperature for 2 days. Quench the reaction mixture by the addition of saturated aqueous $NaHCO_3$, and partition between $CH_2Cl_2$ and water. Adjust aqueous phase to about pH 8, and extract 3 times with $CH_2Cl_2$. Combine the organic fractions and wash with saturated aqueous NaCl, dry over $MgSO_4$, and concentrate. Further purify by chromatography over silica gel, eluting with a gradient of 1-10% methanol in ethylacetate, to obtain the title intermediate (23.8 g, 56% yield): mass spectrum (ion spray): m/z=236.2 (M+1); Anal calc'd for $C_{12}H_{17}N_3O_2.0.3H_2O$: Theory: C, 59.88; H, 7.37; N, 17.45. Found: C, 60.07; H, 7.18; N, 17.09.

Alternatively, to a solution of 3-nitroaniline (360 g, 2.6 mol) in dichloromethane (7.2 L) under nitrogen, add sodium triacetoxyborohydride (1.38 kg, 6.5 mol) by portion over 1 hr. Then add acetic acid (370 mL, 6.5 mol) at a rate such that $T_{mass}$ does not exceed 25° C., followed by 1-methyl 4-piperidone (450 g, 3.98 mol), which is introduced over 150 min., keeping the temperature below 25° C. Stir the mixture at room temperature for 3 hr. Add additional sodium triacetoxyborohydride (280 g, 1.32 mol), acetic acid (74 mL, 1.29 mol), and 1-methyl 4-piperidone (90 g, 0.8 mol) and stir the mixture overnight at room temperature. Quench the reaction mixture with water (4 L) and adjust the pH to between 8-9 with 30% sodium hydroxide. Extract the organic layer and wash the aqueous layer with dichloromethane (2 L). Wash the combined organic layers with water (1 L), dry over $MgSO_4$ (100 g) and concentrate (2×). Filter the resulting suspension, wash with dichloromethane (500 mL), and concentrate the filtrates under reduced pressure (40° C.) to provide the crude 1-methyl-4-(3-nitrophenylamino)piperidine as an orange solid (620 g). Suspend the crude 1-methyl-4-(3-nitrophenylamino) piperidine (590 g) in a mixture of water (5.9 L) and isopropanol (590 mL). Stir the mixture at room temperature for 5 hr. Filter the resulting yellow crystals, rinse with a mixture of water (600 mL) and isopropanol (60 mL) and the dry under reduce pressure at room temperature overnight to provide 1-methyl-4-(3-nitrophenylamino)piperidine (524 g, 94% yield).

Preparation 18

1-Methyl-4-(3-aminophenylamino)piperidine triacetate

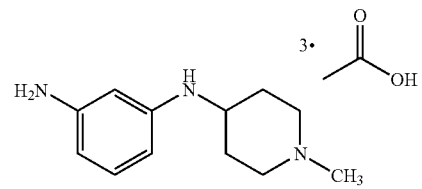

Combine 1-methyl-4-(3-nitrophenylamino)piperidine (Preparation 17) (8.2 g, 34.8 mmol), acetic acid (6.3 g, 110 mmol), and palladium on carbon (10%, 2.1 g) in 300 mL of ethanol. Evacuate the reaction flask, charge with $H_2$ gas (atmospheric pressure) and stir at room temperature for 18 hr. Filter through Celite®, rinse with ethylacetate, and concentrate to provide 13.1 g of the title intermediate, which is typically used in subsequent reactions without further purification. A small sample of the free base amine further purified by dissolving the triacetate salt was dissolved in methanol, placing on a 1 g SCX column (mega bond Elut®, Varian), and washing with methanol, eluting with 2 M $NH_3$ in methanol, and concentrated in vacuo: mass spectrum (ion spray): m/z=206.2 (M+1); $^1$H NMR δ ($CDCl_3$, ppm) 6.93 (t, J=7.9, 15.8 Hz, 1H), 6.03 (d, J=7.9 Hz, 2H), 5.94 (s, 1H), 3.46 (bs, 3H), 3.24 (bs, 1H), 2.79 (m, 2H), 2.28 (s, 3H), 2.10 (m, 4H), 1.40 (m, 2H).

Alternatively, charge a 2 L Parr bottle with 1-methyl-4-(3-nitrophenylamino)piperidine (100 g; 0.425 mol), 10% Pd/C (5 g) and methanol (1 L). Shake the mixture overnight under an initial hydrogen pressure of 4 atm, keeping the temperature below 35° C. Filter off the catalyst and wash with methanol (100 mL). Concentrate the filtrates under reduced pressure to provide 1-methyl-4-(3-aminophenylamino)piperidine as a red oil (95.7 g, 100% yield) which crystallizes upon standing at room temperature.

Preparation 19

1-Methyl-4-(3-chloro-2-fluorophenylamino)piperidine

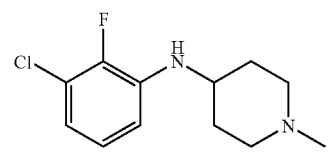

Combine 3-chloro-2-fluoroaniline (4.37 g, 30 mmol), 1-methylpiperidin-4-one (3.39 g, 30 mmol), sodium triacetoxyborohydride (5.26 g, 33 mmol), and acetic acid (5.4 g, 90 mmol) and stir at room temperature overnight. Partition the reaction mixture between dichloromethane and saturated aqueous NaCl containing $NH_4OH$, dry over anhydrous sodium sulfate, evaporate and purify on a silica gel column (110 g), using a gradient of dichloromethane-2M $NH_3$ in methanol to give 2.34 g of the title compound (32% yield): mass spectrum (ion spray): m/z=243 (M+1); $^1$H NMR ($CDCl_3$): 6.88 (ddd, 1H), 6.63 (ddd, 1H), 6.56 (dd, 1H), 3.85

(br d, 1H), 3.28 (m, 1H), 2.80 (m, 2H), 2.30 (s, 3H), 2.13 (m, 2H), 2.04 (m, 1H), 1.53 (m, 2H). (file: mn4-b6k-284-2)

Preparation 20

2-Fluoro-N-(1-methylpiperidin-4-yl)benzene-1,3-diamine

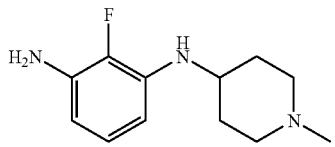

Combine 1-methyl-4-(3-Chloro-2-fluorophenylamino)piperidine (Preparation 19) (0.439 g, 1.8 mmol), benzophenone imine (0.393 g), Pd$_2$(dba)$_3$ (4.1 mg), 2-(dicyclohexylphosphino) biphenyl (4.7 mg), and sodium t-butoxide (0.242 g) with toluene (5 mL) and heat at reflux overnight. Dissolve the reaction mixture in methanol and filter through a SCX column (10 g), wash with methanol, elute the product with 2M NH$_3$ in methanol, evaporate the solvent, and further purify on a silica gel column (35 g, using a dichloromethane-2M NH$_3$ in methanol gradient) to give crude 1-methyl-4-(3-benzhydrylideneamino-2-fluorophenylamino)piperidine (0.372 g). Add 1N HCl (2 mL) into a solution of the benzhydrylidenyl intermediate in THF (10 mL) and stir at room temperature for 30 minutes. Basicify with NH$_4$OH, extract with ethyl acetate, dry over anhydrous sodium sulfate, evaporate and purify on a silica gel column (10 g), using a gradient of dichloromethane-2M NH$_3$ in methanol to give the title intermediate (0.08 g): mass spectrum (ion spray): m/z=224 (M+1); $^1$H NMR (CDCl$_3$): 6.75 (ddd, 1H), 6.12 (m, 2H), 3.70 (bd, 1H), 3.62 (br s, 2H), 3.25 (m, 1H), 2.80 (m, 2H), 2.29 (s, 3H), 2.10 (m, 4H), 1.53 (m, 2H).

Preparation 21

1-Methyl-4-(N-(3-chloro-2-fluorophenyl)methylamino)piperidine

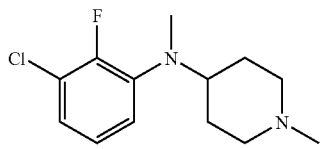

Mix 1-methyl-4-(3-chloro-2-fluorophenylamino)piperidine (Preparation 19) (0.961 g), formaldehyde (37%) (0.973 g), sodium cyanoborohydride (0.917 g) and acetic acid (1.66 g) in methanol (50 mL) and stir at room temperature overnight. Add formaldehyde (37%) (0.973 g), sodium cyanoborohydride (0.917 g) and acetic acid (2 mL) and stir at room temperature overnight. Partition the reaction mixture between dichloromethane and saturated aqueous NaCl, dry over anhydrous sodium sulfate, evaporate and purify on a silica gel column, using a gradient of dichloromethane-2M NH$_3$ in methanol to give 1.06 g of the title intermediate.

Preparation 22

1-Methyl-4-(N-(3-amino-2-fluorophenyl)methylamino)piperidine

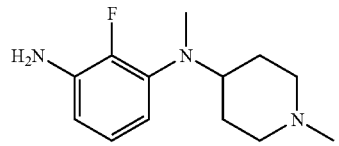

Heat a mixture of 1-methyl-4-(N-(3-chloro-2-fluorophenyl)methylamino)piperidine (Preparation 21) (0.77 g), benzophenone imine (0.652 g), Pd$_2$(dba)$_3$ (6.9 mg), racemic BINAP (7.9 mg) and sodium t-butoxide (0.404 g) in toluene (10 mL) for 44 hours. Dilute the reaction mixture with methanol, load on a SCX column (10 g), wash with methanol, elute the product with 2M NH$_3$ in methanol, evaporate and purify on a silica gel column (110 g), using a gradient of dichloromethane-2M NH$_3$ in methanol to give 0.21 g of 1-methyl-4-(N-(3-benzhydrylidenylamino-2-fluorophenyl)methylamino)piperidine.

Add 2 mL of 1N HCl into a solution of the diamine (0.21 g) and stir for 30 min, basicify with NH$_4$OH, extract with ethyl acetate, dry over anhydrous sodium sulfate, evaporate and purify on a silica gel column (10 g), using a gradient of dichloromethane-2M NH$_3$ in methanol to give 44 mg of the title intermediate.

Preparation 23

1-Methyl-4-(N-(2-fluorophenyl)methylamino)piperidine

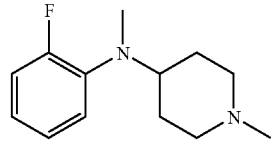

Mix 1-bromo-2-fluorobenzene (3.50 g), 1-methyl-4-(methylamino)piperidine (2.56 g), Pd$_2$(dba)$_3$ (0.366 g), racemic BINAP (0.498 g) and sodium t-butoxide (2.70 g) in toluene (40 mL) and heat at reflux for two days. Filter through a Celite® bed, partition between dichloromethane and saturated aqueous NaCl, dry over anhydrous sodium sulfate, evaporate and purify on a silica gel column (35 g), using a gradient of dichloromethane-2M NH$_3$ in methanol to give 1.1 g of the title intermediate.

Preparation 24

1-Methyl-4-(N-(2-fluoro-3-bromophenyl)methylamino)piperidine

Add n-butyl lithium (1.6 M in hexanes, 4.3 mL) into a solution of 2,2,6,6-tetramethyl-piperidine (0.97 g) in THF (10 mL) at −78° C. and stir for 30 minutes. Add a solution of 1-methyl-4-(N-(2-fluorophenyl)methylamino)piperidine (Preparation 23, 1.02 g) in THF (10 mL) portion wise and stir for 10 minutes. Add 1,2-dibromo-1,1,2,2-tetrachloroethane (1.50 g) in THF (10 mL) dropwise and stir for 1 hr. Remove the cooling bath and stir for 30 minutes. Partition between ethyl acetate and saturated aqueous NaCl, dry over anhydrous sodium sulfate, evaporate and purify on a silica gel column (110 g), using a gradient of dichloromethane-2M $NH_3$ in methanol to give 0.49 g of the title intermediate.

Preparation 25

1-Methyl-4-(N-(2-fluoro-3-aminophenyl)methylamino)piperidine

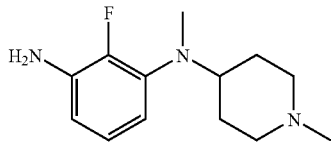

Mix 1-methyl-4-(N-(2-fluoro-3-bromophenyl)methylamino)piperidine (Preparation 24, 0.42 g), benzophenone imine (0.303 g), $Pd_2(dba)_3$ (25 mg), racemic BINAP (35 mg) and sodium t-butoxide (0.187 g) in toluene (10 mL) and heat at reflux for 3 hours. Dilute the reaction mixture with methanol (5 mL), load on a SCX column (10 g), wash with methanol, elute the with 2M $NH_3$ in methanol, evaporate and further purify on a silica gel column (10 g), using a gradient of dichloromethane-2M $NH_3$ in methanol to give 0.44 g of the title intermediate.

Preparation 26

1-Methyl-4-(N-(2-fluoro-3-chlorophenyl)ethylamino)piperidine

Add acetaldehyde (0.817 g) to a solution of 1-methyl-4-(3-chloro-2-fluorophenylamino)piperidine (Preparation 19) (0.45 g), sodium cyanoborohydride (0.123 g) and trifluoroacetic acid (0.633 g) in methanol (20 mL) and heat in a sealed tube at 80° C. for three days. Load on a SCX column (10 g), wash with methanol, elute with 2M $NH_3$ in methanol, evaporate, and further purify on a silica gel column (35 g), using a gradient of dichloromethane-2M $NH_3$ in methanol to give 0.50 g of the title intermediate as a colorless oil: mass spectrum (electric spray) m/z=271 (M+1); $^1$H NMR ($CDCl_3$): 6.94 (m, 3H), 3.14 (q, J=7.0 Hz, 2H), 3.06 (m, 1H), 2.84 (br d, 2H), 2.22 (s, 3H), 1.93 (m, 2H), 1.74 (m, 4H), 0.95 (t, J=7.0 Hz, 3H).

Preparation 27

1-Methyl-4-(N-(2-fluoro-3-aminophenyl)ethylamino)piperidine

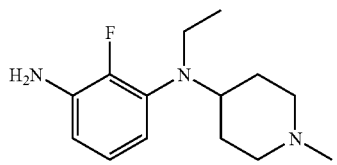

Mix 1-methyl-4-(N-(2-fluoro-3-chlorophenyl)ethylamino)piperidine (Preparation 26) (0.367 g), benzophenone imine (0.295 g), $Pd_2$ (dba)$_3$ (50 mg), 2-(di-t-butylphosphino) biphenyl (32 mg), and sodium t-butoxide (0.182 g) in toluene (10 mL) and heat at reflux for three days. Dilute with methanol (5 mL), 30 minutes after adding 2 mL of 5N HCl, load on a SCX column (10 g), wash with methanol, elute the product with 2M $NH_3$ in methanol, evaporate and purify on a silica gel column (35 g), using a gradient of dichloromethane-2M $NH_3$ in methanol to give 39 mg of the title compound: mass spectrum (electric spray) m/z=252 (M+1).

Preparation 28

1-Methyl-4-(N-(3-nitro-5-fluorophenyl)methylamino)piperidine

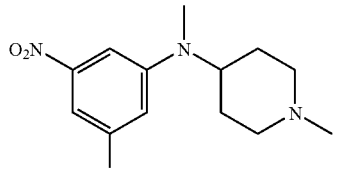

Combine 1,3-difluoro-5-nitro-benzene (1.78 mL, 15.7 mmol), 1-methyl-4-(methylamino)piperidine (2.74 mL, 18.85 mmol), sodium acetate (2.45 g, 29.8 mmol) and absolute ethanol (10 mL) in a sealed tube. Heat and stir at 100° C. for 16 hr. Cool the reaction mixture to ambient temperature and pour into water (100 mL). Extract with ethyl acetate (2×100 mL). Wash combined organic layers with saturated aqueous NaCl solution (100 mL), dry over sodium sulfate, filter, and concentrate. Purify residue by silica gel flash chromatography eluting with 10% (2M $NH_3$ in methanol) in $CH_2Cl_2$ to obtain 0.06 g (1.4%) of the title intermediate: $^1$H NMR ($CDCl_3$): 7.3 (m, 1H), 7.2 (m, 1H), 6.7 (m, 1H), 3.6 (m, 1H), 3.0 (m, 2H), 2.8 (s, 3H), 2.3 (s, 3H), 2.2 (m, 2H), 1.9 (m, 2H), 1.7 (m, 2H).

Preparation 29

1-Methyl-4-(N-(3-amino-5-fluorophenyl)methylamino)piperidine

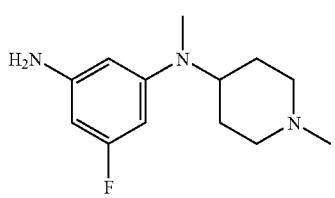

Combine 1-methyl-4-(N-(3-nitro-5-fluorophenyl)methylamino)piperidine (Preparation 28) (0.06 g, 0.22 mmol), iron dust (0.06 g, 1.12 mmol), methanol (5 mL) and 1M HCl (0.22 mL, 0.22 mmol), stir, and heat at reflux for 18 hr. Cool the reaction mixture to ambient temperature, dilute with ethyl acetate (50 mL), and add 1N sodium hydroxide solution until basic (pH=9). Separate organic layer, wash with saturated aqueous NaCl solution, dry over sodium sulfate, filter, and concentrate to obtain 0.036 g (69%) of the title intermediate: $^1$H NMR (CDCl$_3$): 5.9 (m, 1H), 5.7 (m, 2H), 3.6 (bs, 2H), 3.4 (m, 1H), 2.9 (m, 2H), 2.7 (s, 3H), 2.3 (s, 3H), 2.0 (m, 2H), 1.8 (m, 2H), 1.7 (m, 2H).

Preparation 30

1-Methyl-4-(N-(3-bromo-5-fluorophenyl)methylamino)piperidine

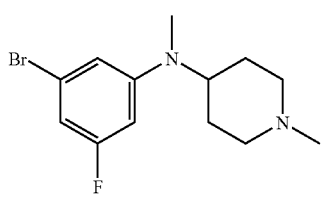

Combine 1,3-dibromo-5-fluorobenzene (5.0 g, 19.7 mmol), 1-methyl-4-(methylamino)piperidine (2.58 mL, 17.7 mmol), 2,2'-bis(diphenylphosphino)-1,1'-binaphthyl (0.49 g, 0.79 mmol), sodium t-butoxide (2.57 g, 27.58 mmol) and toluene (100 mL), stir and heat at 80° C. After 10 minutes, add Pd$_2$(dba)$_3$ (0.49 g, 0.79 mmol). After 3 hr. at 80° C., cool to ambient temperature. Dilute with ethyl acetate (100 mL) and wash with water (50 mL). Dry the organic layer over sodium sulfate, filter, and concentrate to an oil. Purify the residue by silica gel flash chromatography eluting with 10% (2M NH$_3$-methanol) in CH$_2$Cl$_2$ to obtain 2.95 g (55%) of the title intermediate: $^1$H NMR (CDCl$_3$): 6.6 (s, 1H), 6.5 (m, 1H), 6.3 (m, 1H), 3.5 (m, 1H), 2.9 (m, 2H), 2.7 (s, 3H), 2.3 (s, 3H), 2.0 (m, 2H), 1.8 (m, 2H), 1.7 (m, 2H).

Preparation 31

1-Methyl-4-(N-(3-amino-5-fluorophenyl)methylamino)piperidine

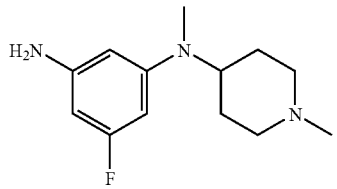

Combine 1-methyl-4-(N-(3-bromo-5-fluorophenyl)methylamino)piperidine (Preparation 30, 2.90 g, 9.63 mmol), benzophenone imine (1.94 mL, 11.55 mmol), 2,2'-bis(diphenylphosphino)-1,1'-binaphthyl (0.24 g, 0.39 mmol), sodium t-butoxide (1.26 g, 13.48 mmol), and toluene (60 mL), stir and heat to 80° C. After 10 minutes, add Pd$_2$(dba)$_3$ (0.17 g, 0.19 mmol). After 3 hr at 80° C., cool to ambient temperature. Dilute with ethyl acetate (100 mL) and wash with water (50 mL). Separate organic layer, dry over sodium sulfate, filter and concentrate. Dissolve this material in tetrahydrofuran (120 mL) and treat with 1M aqueous hydrochloric acid solution (40 mL). After stirring at ambient temperature for 1 hr, add 2M sodium hydroxide solution until basic (21 mL). Extract with ethyl acetate (2×100 mL). Wash organic layer with saturated aqueous NaCl solution (75 mL), dry over sodium sulfate, filter and concentrate to an oil. Purify residue by silica gel flash chromatography eluting with 10% (2M NH$_3$ in methanol) in CH$_2$Cl$_2$ to obtain 1.96 g (86%) of the title compound.

Preparation 32

1,3-Diamino-5-fluorobenzene

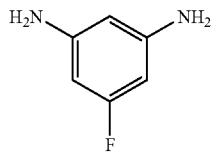

Add 1,3-dibromo-5-fluorobenzene (5.078 g, 20 mmol), benzophenone imine (8.700 g, 48 mmol), Pd$_2$(dba)$_3$ (366 mg, 0.4 mmol), BINAP (747 mg, 1.2 mmol) and sodium t-butoxide (4.998 g, 52 mmol) to toluene (100 mL). Heat the reaction mixture at 80° C. for 15 hr. Quench the reaction with saturated NaHCO$_3$ solution. Extract the mixture with ethylacetate three times. Wash the combined organic layers with saturated NaCl solution, dry over Na$_2$SO$_4$, filter and concentrate to give a residue. Dissolve the residue in THF (80 mL), add 5N HCl (14 mL), and stir for 2 hr. Dilute the reaction mixture with 0.1N HCl and extract with ethylacetate/hexanes (1:2) twice. Wash the combined organic layer once with 0.1N HCl, combine the aqueous layers, adjust to pH>11 with 5N NaOH. Extract the turbid mixture with CH$_2$Cl$_2$ three times. Combine the organic layers, dry over Na$_2$SO$_4$, filter, and concentrate to give an orange-color oil. Purify by chromatography on silica gel, eluting with 30-60% ethylacetate in hexanes to obtain the title intermediate as a yellow oil (1.955 g, 77%): mass spectrum (ion spray): m/z=127.1 (M+1), $^1$H NMR (CDCl$_3$, ppm): 5.82 (m, 3H), 3.67 (s, br, 2H).

Preparation 33

1-Methyl-4-(N-(6-bromopyridinyl)methylaminopiperidine

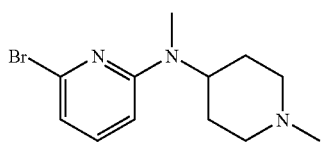

Dissolve 2,6-dibromopyridine (5.0 g, 21.1 mmol), (±)-BINAP (1.09 g, 1.76 mmol), and Pd$_2$(dba)$_3$ (805 mg, 0.88 mmol) in toluene (50 mL). Stir and add 1-methyl-4-(methylamino)piperidine (2.56 mL, 17.6 mmol) followed by sodium t-butoxide (2.37 g, 24.6 mmol). Heat the reaction mixture to 80° C. for 40 hr. Cool the reaction mixture to room temperature and partition between ethyl acetate and water. Separate the organic layer, and extract the aqueous layer with dichloromethane (2×50 mL). Combine the organic extracts, dry over MgSO$_4$, filter, and concentrate in vacuo. Load residue onto an SCX column and wash with methanol. Elute with 2M ammonia in methanol and concentrate in vacuo. Further purify the product by column chromatography on silica gel using a gradient of 2%-10% (2M NH$_3$ in methanol) in CH$_2$Cl$_2$) to give of the title intermediate (632 mg, 13%): mass spectrum (ion spray): m/z 286.0 (M+1); $^1$H NMR: δ (CDCl$_3$, ppm) 7.25 (m, 1H), 6.65 (d, J=8.0 Hz, 1H), 6.35 (d, J=8.4 Hz, 1H), 4.37 (m, 1H), 2.94 (m, 2H), 2.85 (s, 3H), 2.30 (s, 3H), 2.13 (m, 2H), 1.85 (m, 2H), 1.68 (m, 2H).

Preparation 34

1-Methyl-4-(N-(6-aminopyridinyl)methylaminopiperidine

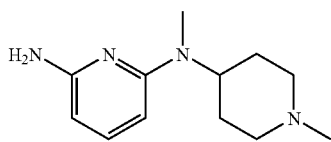

Mix 1-methyl-4-(N-(6-bromopyridinyl)methylaminopiperidine (1.02 g, 3.59 mmol) (Preparation 33), (±)-BINAP (224 mg, 0.36 mmol), and Pd$_2$(dba)$_3$ (164 mg, 0.18 mmol) in toluene (20 mL). Add benzophenone imine (723 μL, 4.31 mmol) and sodium tert-butoxide (483 mg, 5.03 mmol) to the reaction and heat to 80° C. for 19 hr. Cool the reaction mixture to room temperature and partition between ethyl acetate and water. Separate the organic layer, and extract the aqueous layer with dichloromethane (2×50 mL). Combine the organic extracts, dry (MgSO$_4$), filter, and concentrate in vacuo. Dissolve the residue in 50 mL of 1:1 THF/H$_2$O and treat with 50 mL of aqueous 1N HCl for 2 hr. Load the solution onto an SCX column, and wash successively with 1:1 THF/H$_2$O, methanol, and finally with 2M ammonia in methanol. Concentrate the basic wash in vacuo, and purify the residue by column chromatography on silica gel using a gradient of 2%-10% (2M NH$_3$ in methanol) in CH$_2$Cl$_2$ to give of the title intermediate (459 mg, 58%): mass spectrum (ion spray): m/z=221.2 (M+1), Analysis Calcd for C$_{12}$H$_{20}$N$_4$·0.1 CH$_2$Cl$_2$: C, 63.51; H, 8.90; N, 24.49. Found: C, 63.42; H, 8.56; N, 24.25.

Preparation 35

1-Methyl-4-(N-(6-chloropyridin-2-yl)methylamino) piperidine

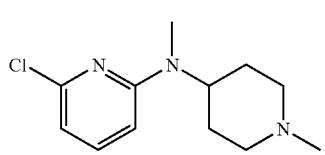

Dissolve 1-methyl-4-(methylamino)piperidine (10 mL, 68.8 mmol) in tetrahydrofuran (50 mL) and cool to −78° C. Slowly add n-butyllithium (1.6 N in hexane, 43 mL, 68.8 mmol) to the reaction mixture and stir at −78° C. for 30 min. Warm the reaction mixture to room temperature and stir for 30 min. Then cool the reaction mixture to −78° C. and add 2,6-dichloropyridine (11.2 g, 75.7 mmol) in tetrahydrofuran (50 mL). Stir the reaction mixture at −78° C. for 15 min, warm to room temperature, and then heat to 60° C. for 19 hr. Cool the reaction mixture to room temperature and partition between ethyl acetate and water. Separate the organic layer and extract the aqueous layer with dichloromethane (2×50 mL). Combine organic extracts, dry (MgSO$_4$), filter, and concentrate in vacuo. Purify the residue by column chromatography on silica gel using a gradient of 2%-10% (2M NH$_3$ in methanol) in CH$_2$Cl$_2$ to give of the title intermediate (11.91 g, 72%): mass spectrum (ion spray): m/z=240.1 (M+1); $^1$H NMR: δ (CDCl$_3$, ppm) 7.34 (t, J=7.6, 16.0 Hz, 1H), 6.50 (d, J=8.0 Hz, 1H), 6.33 (d, J=8.8 Hz, 1H), 4.41 (m, 1H), 2.94 (m, 2H), 2.86 (s, 3H), 2.32 (s, 3H), 2.15 (m, 2H), 1.84 (m, 2H), 1.68 (m, 2H).

Preparation 36

1-Methyl-4-(N-(6-aminopyridine) methylamino)piperidine

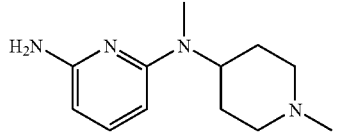

Place 1-methyl-4-(N-(6-chloropyridin-2-yl)methylamino) piperidine (Preparation 35, 1.62 g, 6.76 mmol), (±)-BINAP (420 mg, 0.68 mmol), and Pd$_2$(dba)$_3$ (310 mg, 0.34 mmol) in toluene. (15 mL). Add benzophenone imine (1.36 mL, 8.11 mmol) and sodium tert-butoxide (910 mg, 9.46 mmol) to the reaction and heat to 80° C. for 20 hr. Cool the reaction to room temperature and partition between ethyl acetate and water. Separate the organic layer, and extract the aqueous layer with dichloromethane (2×50 mL). Combine the organic extracts, dry over MgSO₄, filter, and concentrate in vacuo. Load the residue on an SCX column, wash with methanol, elute with 2M ammonia in methanol, and concentrate in vacuo. Dissolve the residue in 50 mL of 1:1 THF/H₂O and treat with 50 mL of 1N HCl for 2 hr. Load the solution onto an SCX column, and wash successively with 1:1 THF/H₂O, methanol, and finally with 2M ammonia in methanol. Concentrate the basic wash in vacuo, and purify the residue by column chromatography on silica gel using a gradient of 2%-10% (2M NH₃ in methanol) in CH₂Cl₂ to give of the title intermediate (1.38 g, 93%): mass spectrum (ion spray): m/z=221.1 (M+1); ¹H NMR: δ (CDCl₃, ppm) 7.23 (t, J=9.2, 17.2 Hz, 1H), 5.86 (d, J=8.0 Hz, 1H), 5.78 (d, J=7.2 Hz, 1H), 4.46 (m, 1H), 4.13 (bs, 2H), 2.94 (m, 2H), 2.81 (s, 3H), 2.31 (s, 3H), 2.11 (m, 2H), 1.84 (m, 2H), 1.65 (m, 2H).

Preparation 37

N-(6-Aminopyridin-2-yl)-4-fluorobenzamide

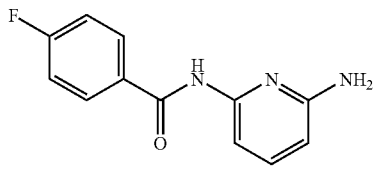

Combine triethylamine (15.8 mL, 111.0 mmol) and 2,6-diaminopyridine (6.5 g, 59.6 mmol) in dioxane (200 mL). Add 4-fluorobenzoyl chloride (5.46 mL, 44.7 mmol) in small increments. After complete addition, stir at room temperature for 18 hr. Pour into water and dilute with ethyl acetate and water. Separate and extract twice the aqueous layer with CH₂Cl₂, combine the organic fractions, dry over MgSO₄, and concentrate. Chromatograph on silica gel, eluting with a gradient of 0%-10% (2M NH₃ in methanol) in CH₂Cl₂ to give the title intermediate (8.91 g, 86.3%): mass spectrum (ion spray): m/z=232.3 (M+1); Analysis calculated for C₁₂H₁₀N₃OF 0.1H₂O: C, 61.85; H, 4.41; N, 18.03. Found: C, 61.75; H, 4.08; N, 17.66.

Preparation 38

N-(6-Aminopyridin-2-yl)-2-chloro-4-fluorobenzamide

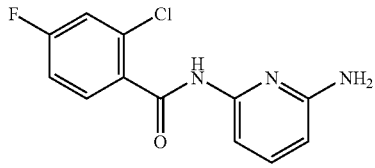

Using a method similar to Preparation 37, using 2-chloro-4-fluorobenzoyl chloride, gives the title intermediate as a tan solid: mass spectrum (ion spray): m/z=266.2 (M+1); Analysis calculated for C₁₂H₉N₃OClF: C, 54.25; H, 3.41; N, 15.82. Found: C, 53.98; H, 3.23; N, 15.54.

Preparation 39

4-(6-(4-Fluorobenzoylamino)pyridin-2-ylamino)piperidine-1-carboxylic acid t-butyl ester

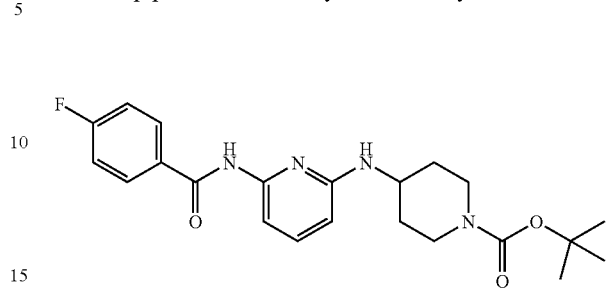

Place N-(6-aminopyridin-2-yl)-4-fluorobenzamide (Preparation 37) (2 g, 8.3 mmol) and 1-boc-4-piperidone (15.0 g, 83 mmol) in 1,2-dichloroethane (20 mL). Stir for 1 hr. then add sodium triacetoxyborohydride (4.38 g, 20.8 mmol). After stirring for 36 hr., quench with 1 N NaOH and dilute with CH₂Cl₂. Separate and extract the aqueous layer twice with CH₂Cl₂, combine organics, dry over MgSO₄, and concentrate. Take up the residue in CH₂Cl₂, and place on two 10 g SCX columns. Wash the columns successively with CH₂Cl₂ and then with methanol. Elute the product with 2M NH₃ in methanol. Concentrate and chromatograph on silica gel, eluting with a gradient of 0-10% (2M NH₃ in methanol) in CH2Cl2) to give the title intermediate 3.11 g (90%): mass spectrum (ion spray): m/z 415.4 (M+1); mp 82.7° C.

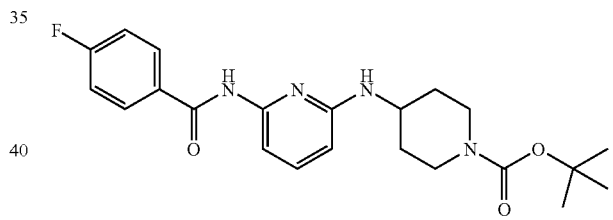

Preparation 40

4-(6-(2-Chloro-4-fluorobenzoylamino)pyridin-2-ylamino)piperidine-1-carboxylic acid tert-butyl ester

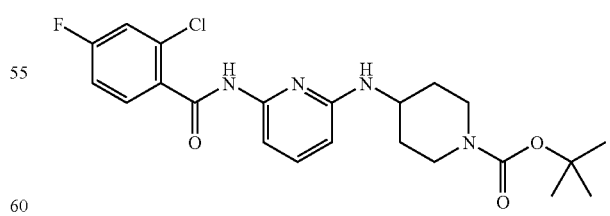

Using a method similar to Preparation 39, using N-(6-aminopyridin-2-yl)-2-chloro-4-fluorobenzamide (Preparation 38, 2.0 g, 7.5 mmol), gives the title intermediate as a white solid: mass spectrum (ion spray): m/z=449.4 (M+1); mp 82.0° C.

Preparation 41

4-((6-(4-Fluorobenzoylamino)pyridin-2-yl)methylamino)piperidine-1-carboxylic acid tert-butyl ester

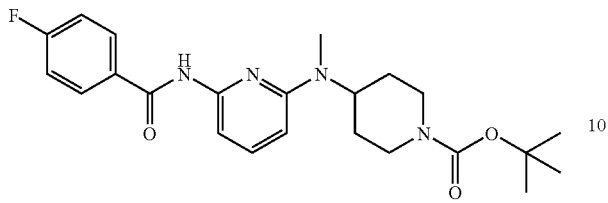

Place 4-(6-(4-fluorobenzoylamino)pyridin-2-ylamino)piperidine-1-carboxylic acid t-butyl ester (Preparation 39) (3.1 g, 7.4 mmol) and formaldehyde (37% in water) (6.1 mL, 74 mmol) in methanol (10 mL) and stir for 36 hr. Add sodium cyanoborohydride (2.3 g, 37.0 mmol) and stir for 2 hr. Quench the reaction with 1N NaOH and dilute with $CH_2Cl_2$. Separate and extract the aqueous layer twice with $CH_2Cl_2$, and once with 3:1 $CHCl_3$:isopropanol. Combine the organic fractions, dry over $MgSO_4$, and concentrate. Chromatograph on silica gel, eluting with a gradient of 0-10% (2M $NH_3$ in methanol) in $CH_2Cl_2$ to give the title intermediate (0.97 g, 30.6%): mass spectrum (ion spray): m/z=429.4 (M+1); mp 77.7° C.

Preparation 42

4-((6-(2-Chloro-4-fluorobenzoylamino)pyridin-2-yl)methylamino)piperidine-1-carboxylic acid tert-butyl ester

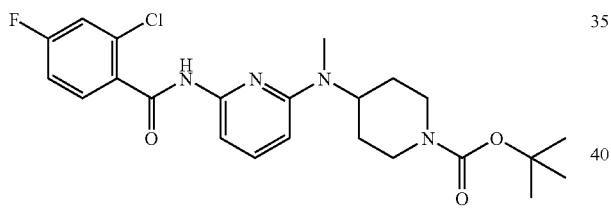

Using a method similar to Preparation 41, using 4-(6-(2-chloro-4-fluorobenzoylamino)pyridin-2-ylamino)piperidine-1-carboxylic acid t-butyl ester (Preparation 40, 2.11 g, 4.6 mmol), gives the title intermediate as a white solid: mass spectrum (ion spray): m/z=463.3 (M+1); mp 79.1° C.

Preparation 43

N-(6-Aminopyridin-2-yl)-2,4,6-trifluorobenzamide

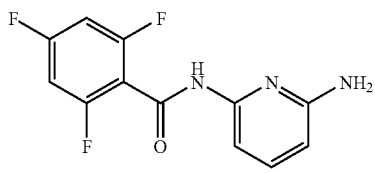

Combine 2,4,6-trifluorobenzoyl chloride (3.891 g, 20 mmol), 2,6-diaminopyridine (6.548 g, 60 mmol) and dioxane (25 mL) and stir for 1 hr. at room temperature followed by heating at 40° C. overnight. Dilute the reaction mixture with $CH_2Cl_2$ (100 mL), and wash with 0.1N NaOH solution. Extract the aqueous layer three times with $CH_2Cl_2$. Combine the organic layers, dry over $Na_2SO_4$, filter, and concentrate to a residue. Chromatography on silica gel, eluting with a gradient of 40-50% ethylacetate in hexanes gives the title intermediate (3.95 g, 74%): mass spectrum (ion spray): m/z=267.9 (M+1); $^1$H NMR ($CDCl_3$, ppm): 8.28 (s, br, 1H), 7.66 (d, 1H), 7.52 (t, 1H), 6.78 (m, 2H), 6.31 (d, 1H), 4.36 (s, br, 2H).

Preparation 44

N-(6-Amino-pyridin-2-yl)acetamide

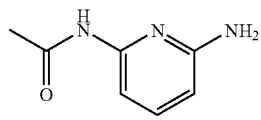

Dissolve 2,6-diaminopyridine (9.822 g, 90 mmol) in dioxane (100 mL) and cool to 0° C. Add acetyl chloride (2.355 g, 2.1 mL, 30 mmol) slowly and stir for 1 hr. at 0° C. Remove the ice bath and stir at room temperature overnight. Quench the reaction mixture with saturated $NaHCO_3$ solution, extract with ethyl acetate three times. Combine the organic layers, dry over $Na_2SO_4$, filter, and concentrate to give a solid. Chromatography on silica gel, eluting with a gradient of 60-70% ethylacetate in hexanes affords the title intermediate (3.45 g, 76%): mass spectrum (ion spray): m/z=152.1 (M+1); $^1$H NMR ($CDCl_3$, ppm): 7.49 (m, 3H), 6.28 (d, 1H), 4.31 (s, br, 2H), 2.19 (s, 3H).

Preparation 45

N-(6-Aminopyridin-2-yl)-2-chlorobenzamide

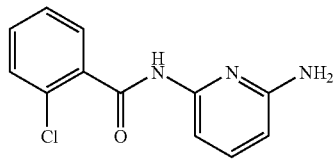

Using a method similar to Preparation 44, using 2-chlorobenzoyl chloride (875 mg, 5.0 mmol) gives the title intermediate of as a white solid (1.172 g, 95%): mass spectrum (ion spray) m/z=247.9 (M+1); $^1$H NMR ($CDCl_3$, ppm): 8.37 (s, 1H), 7.72 (m, 2H), 7.44 (m, 4H), 6.31 (d, 1H), 4.36 (s, br, 2H).

Preparation 46

N-(6-Amino-pyridin-2-yl)-2-bromobenzamide

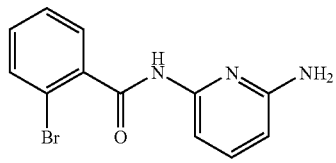

Using a method similar to Preparation 44, using 2-bromobenzoyl chloride (1.097 g, 5.0 mmol) gives the title intermediate as a white solid (1.445 g, 99%): mass spectrum (ion spray): m/z=291.9 (M+1); $^1$H NMR (CDCl$_3$, ppm): 8.27 (s, br, 1H), 7.65 (m, 4H), 7.34 (m, 2H), 6.29 (d, 1H), 4.36 (s, br, 2H).

Preparation 47

Cyclohexanecarboxylic acid (6-aminopyridin-2-yl)amide

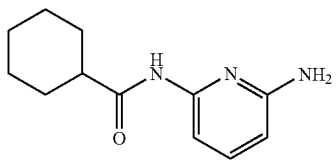

Using a method similar to Preparation 44, using cyclohexanecarbonyl chloride (733 mg, 5.0 mmol) gives the title intermediate as a white solid (1.137 g, 100%): mass spectrum (ion spray): m/z=242.0 (M+Na); $^1$H NMR (CDCl$_3$, ppm): 7.97 (s, 1H), 7.56 (d, 1H), 7.43 (dd, 1H), 6.23 (dd, 1H), 4.40 (s, br, 2H), 2.18 (m, 1H), 1.81 (m, 4H), 1.66 (1H), 1.46 (2H), 1.20 (m, 3H).

Preparation 48

N-(6-Aminopyridin-2-yl)-2-chloro-6-fluorobenzamide

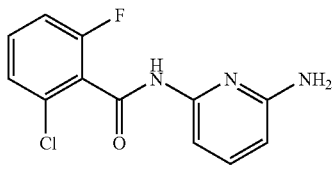

Dissolve 2,6-diaminopyridine (1.3 g, 12 mmol) in dioxane (30 mL). Add 2-chloro-6-fluorobenzoyl chloride (768 mg, 4 mmol). Stir under nitrogen (40° C., 64 hr.). Transfer the reaction mixture into ethyl acetate (150 mL). Wash with saturated sodium bicarbonate solution (80 mL). Dry over anhydrous sodium sulfate. Remove the solvent under reduced pressure and clean by chromatography (silica gel, 10% ethyl acetate/hexanes) to give the title intermediate (820 mg, 78% yield): mass spectrum (ion spray): m/z=266.0 (M+1).

Preparation 49

N-(6-Aminopyridin-2-yl)-3-chloro-2,6-difluorobenzamide

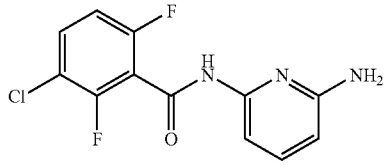

Using a method similar to Preparation 48, using 3-chloro-2,6-difluorobenzoyl chloride (840 mg, 4 mmol) gives the title intermediate (761 mg, 67% yield): mass spectrum (ion spray): m/z=284.0 (M+1).

Preparation 50

N-(6-Aminopyridin-2-yl)-2,6-difluoro-3-methylbenzamide

Using a method similar to Preparation 48, using 2,6-difluoro-3-methylbenzoyl

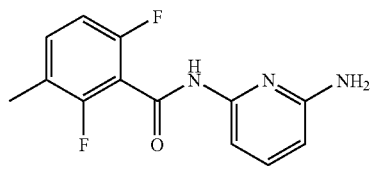

chloride (760 mg, 4 mmol) gives the title intermediate (669 mg, 64% yield): mass spectrum (ion spray): m/z=264.1 (M+1).

Preparation 51

N-(6-Aminopyridin-2-yl)-2,4-difluorobenzamide

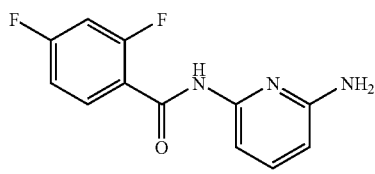

Using a method similar to Preparation 48, using 2,4-difluorobenzoyl chloride (704 mg, 4 mmol, stir at 25° C. for 16 hr.) gives the title intermediate (625 mg, 63% yield): mass spectrum (ion spray): m/z=250.0 (M+1).

Preparation 52

N-(6-Aminopyridin-2-yl)-2,6-dichlorobenzamide

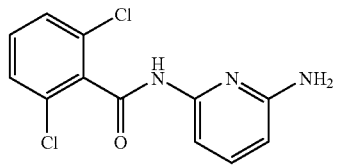

Using a method similar to Preparation 48, using 2,6-diaminopyridine (2.6 g, 24 mmol), dioxane (75 mL), and 2,6-dichlorobenzoyl chloride (1.68 g, 8 mmol) (stir at 25° C. for 16 hr.) gives the title intermediate (1.5 g, 66% yield): mass spectrum (ion spray): m/z=282.0 (M+1)

Preparation 53

N-(6-Aminopyridin-2-yl)-2,6-difluorobenzamide

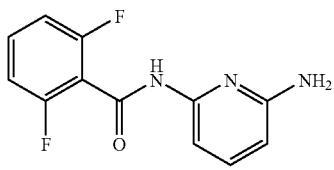

Using a method similar to Preparation 48, using 2,6-diaminopyridine (2.6 g, 24 mmol), dioxane (75 mL), and 2,6-difluorobenzoyl chloride (1.4 g, 8 mmol) (stir at 25° C. for 16 hr.), gives the title intermediate (1.5 g, 75% yield): mass spectrum (ion spray): m/z=250.1 (M+1).

Preparation 54

N-(6-Aminopyridin-2-yl)-2,4-dichlorobenzamide

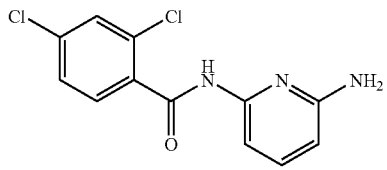

Using a method similar to Preparation 48, using 2,4-dichlorobenzoyl chloride (838 mg, 4 mmol) (stir at 0-25° C. for 16 hr.), gives the title intermediate (621 mg, 56% yield): mass spectrum (ion spray): m/z=282.0 (M+1).

Preparation 55

N-(6-Aminopyridin-2-yl)-2,4,6-trichlorobenzamide

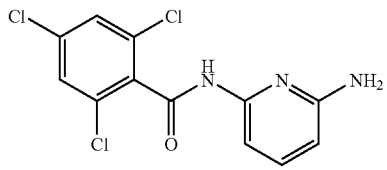

Using a method similar to Preparation 48, using 2,6-diaminopyridine (2.6 g, 12 mmol), dioxane (80 mL), and 2,4,6-trichlorobenzoyl chloride (1.95 g, 8 mmol) (stir at 0-25° C. for 16 hr.) gives the title intermediate (1.0 g, 39% yield): mass spectrum (ion spray): m/z=316.0 (M+1).

EXAMPLES

Example 1

2-Chloro-4-fluoro-N-(3-(1-methylpiperidin-4-ylamino)phenyl)benzamide dihydrochloride

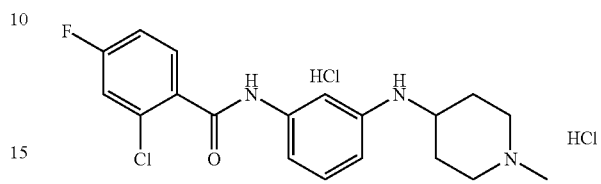

Combine 2-chloro-4-fluoro-N-(3-aminophenyl)benzamide (Preparation 1, 200 mg, 0.756 mmol), 1-methylpiperidin-4-one (0.093 mL, 0.756 mmol), sodium triacetoxyborohydride (208 mg, 0.982 mmol), acetic acid (0.043 mL, 0.756 mmol) and dichloromethane (8 mL). Stir at room temperature overnight. Dilute with dichloromethane (5 mL) and wash twice with sodium hydroxide (10 mL 1N aq.). Combine the organic layers and wash with saturated aqueous NaCl (10 mL). Dry over magnesium sulfate, filter under reduced pressure and concentrate to dryness. Purify by flash chromatography on a Biotage® silica cartridge eluting with a 20/1 mixture of dichloromethane and 2N ammonia in methanol to give the free base of the title compound (239 mg, 87%). Dissolve the residue in diethyl ether and treat with ethereal hydrogen chloride. Triturate the resulting gum with ether to give the title compound as a white solid (31 mg): mp 180° C.; mass spectrum (free base, ion spray): m/z=362.1 (M+1), $^1$H NMR (free base, CDCl$_3$): 7.80-7.75 (m, 2H), 7.23 (bs, 1H), 7.19 (dd, J=2.4 Hz, 8.3 Hz, 1H), 7.13 (t, J=8.2 Hz, 1H), 7.08 (dd, J=2.4 Hz, 8.3 Hz, 1H), 6.67 (d, J=7.8 Hz, 1H), 6.41 (dd, J=2.0 Hz, 8.3 Hz, 1H), 3.68 (bd, J=7.9 Hz, 1H), 3.36 (bs, 1H), 2.92-2.81 (bm, 2H), 2.35 (s, 3H), 2.82-2.17 (bm, 2H), 2.10 (bd, J=13.0 Hz, 2H), 1.64-1.51 (bm, 2H). Analysis calc'd for C$_{19}$H$_{23}$Cl$_3$FN$_3$O: C, 51.95; H, 5.39; N, 9.57. Found: C, 52.03; H, 5.46; N, 9.17.

Alternatively, to a solution of 1-methyl-4-(3-aminophenylamino)piperidine (92 g, 17 mmol) and triethylamine (156 mL, 39 mmol) in dry THF (1 L), add dropwise 2-chloro-4-fluorobenzoyl chloride (3.6 g, 18.6 mmol), under nitrogen, over 1 hr., keeping the T$_{mass}$ between 20° C. and 26° C. Agitate the suspension at room temperature for 1 hr. Quench the reaction mixture with water (100 mL) and 30% NaOH (40 mL) to obtain a biphasic solution (pH~8-9). Extract with methyl t-butyl ether (500 mL), wash the organic layer with water (100 mL), dry over MgSO$_4$, and concentrate under reduced pressure to obtain 2-Chloro-4-fluoro-N-(3-(1-methylpiperidin-4-ylamino)phenyl)benzamide as an amorphous solid. Suspend the solid with methyl t-butyl ether (400 mL) and warm the mixture under reflux for 2 hr. Cool the mixture to room temperature, add cyclohexane (100 mL) and methyl t-butyl ether (250 mL). Filter the resulting crystals, rinse with methyl t-butyl ether (160 mL) and dry under reduced pressure at 50° C. overnight to obtain 2-Chloro-4-fluoro-N-(3-(1-methylpiperidin-4-ylamino)phenyl)benzamide as a white powder (123 g, 76% yield).

Example 1A

2-Chloro-4-fluoro-N-(3-(1-methylpiperidin-4-ylamino)phenyl)benzamide fumarate salt Fumaric acid (170 mg; 1.46 mmol) is added to a suspension of 2-Chloro-4-fluoro-N-(3-(1-methylpiperidin-4-ylamino)phenyl)benzamide (free base of Example 1, 500 mg, 1.38 mmol) in isopropanol (5 mL) at room temperature. The suspension is heated under reflux for 1 hr., cooled down to room temperature and post-agitated for 2 hr. The crystals are filtered, washed with isopropanol (2×0.5 mL) and dried under reduced pressure at 40° C. to give a white solid (665 mg, 100% yield). These crystals (100 mg; 0.21 mmol) are resuspended in water (1 mL) and stirred at room temperature. After 5 min. of stirring, the suspension becomes an orange homogeneous solution (after about 5 min) and then fine crystals appear (after about 10 min). The mixture is post-agitated overnight. The suspension is then filtered, the solid washed with water (0.1 mL) and dried under reduced pressure to give the title compound as a pure white solid (76 mg, 76% yield).

Example 2

2-Chloro-4-fluoro-N-(3-(N-cyclopropylcarbonyl-N-(1-methylpiperidin-4-yl)amino)phenyl)benzamide hydrochloride

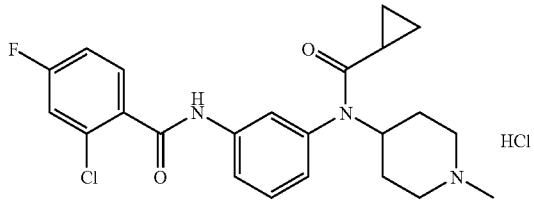

Combine 2-chloro-4-fluoro-N-(3-(1-methylpiperidin-4-ylamino)phenyl)benzamide dihydrochloride (Example 1, 48 mg, 0.134 mmol), dioxane (1 mL) and cyclopropylcarbonyl chloride (0.013 mL, 0.148 mmol). Shake and heat (106° C.) in a J-Kem® Reaction Block for 2 hr. Load onto a SCX column (Varian) and elute with 2 M ammonia methanol to give the free base of the title compound (54 mg, 93%). Following a salt formation method similar to that described in Example 1 gives the title compound as a white solid (47 mg): mp 133-6° C.; mass spectrum (freebase, ion spray): m/z=430.1 (M+1), $^1$H NMR (freebase, CDCl$_3$): 8.31 (bs, N—H), 7.76 (dd, J=6.0 Hz, 8.6 Hz, 1H), 7.61-7.56 (m, 2H), 7.38 (t, J=8.0 Hz, 1H), 7.19 (dd, J=2.4 Hz, 8.3 Hz, 1H), 7.09 (td, J=2.4 Hz, 8.2 Hz, 1H), 6.96 (d, J=8.2 Hz, 1H), 4.62-4.53 (m, 1H), 2.80 (bd, J=11.5 Hz, 2H), 2.20 (s, 3H), 2.05 (td, J=2.2 Hz, 12.1 Hz, 2H), 1.83-1.69 (bm, 2H), 1.59-1.37 (bm, 2H), 1.21-1.13 (m, 1H), 0.99-0.89 (bm, 2H), 0.56 (bd, J=7.4 Hz, 2H). Analysis calc'd for C$_{23}$H$_{26}$Cl$_2$FN$_3$O$_2$.0.8H$_2$O: C, 57.46; H, 5.79; N, 8.74. Found: C, 57.16; H, 5.73; N, 8.70.

Example 3

2-Chloro-4-fluoro-N-(3-(N-cyclobutanecarbonyl-N-(1-methylpiperidin-4-yl))amino)phenyl)benzamide hydrochloride

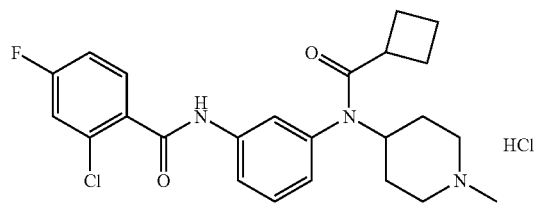

Using a method similar to Example 2, using cyclobutylcarbonyl chloride (0.017 mL, 0.148 mmol) gives the title compound as a white solid (freebase, 46 mg, 78%; hydrochloride, 30 mg): mass spectrum (freebase, ion spray): m/z=444.2 (M+1), $^1$H NMR (freebase, CDCl$_3$): 8.29 (bs, N—H), 7.77 (dd, J=6.0 Hz, 8.8 Hz, 1H), 7.54 (d, J=8.2 Hz, 1H), 7.50-7.48 (bs, 1H), 7.34. (t, J=8.0 Hz, 1H), 7.19 (dd, J=2.4 Hz, 8.5 Hz, 1H), 7.09 (td, J=2.3 Hz, 8.2 Hz, 1H), 4.56 (tt, J=4.2 Hz, 12.1 Hz, 1H), 2.89-2.76 (m, 3H), 2.32-2.18 (m, 5H), 2.06 (td, J=2.1 Hz, 12.1 Hz, 2H), 1.82-1.64 (bm, 6H), 1.54-1.32 (bm, 2H). Analysis calculated for C$_{24}$H$_{28}$Cl$_2$FN$_3$O$_2$.1.0H$_2$O: C, 57.83; H, 6.07; N, 8.43. Found: C, 57.77; H, 5.97; N, 8.36.

Example 4

2-Chloro-6-fluoro-N-(3-(1-methylpiperidin-4-ylamino)phenyl)benzamide dihydrochloride

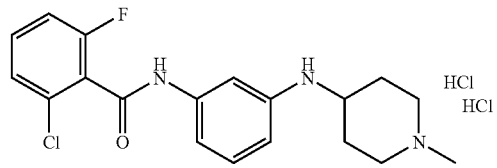

Using a method similar to Example 1, using 2-chloro-6-fluoro-N-(3-aminophenyl)benzamide (Preparation 2, 300 mg, 1.133 mmol) gives the title compound as a white solid (free base 358 mg, 87%; dihydrochloride 415 mg): mp 192-4° C.; mass spectrum (freebase, ion spray): m/z=362.0 (M+1), $^1$H NMR (freebase, CDCl$_3$): 7.41 (bs, N—H), 7.38-7.32 (m, 1H), 7.24 (bs, 1H), 7.13 (t, J=8.2 Hz, 1H), 7.08 (td, J=0.9 Hz, 8.5 Hz, 1H), 6.66 (dd, J=2.0 Hz, 8.0 Hz, 1H), 6.41 (dd, J=2.1 Hz, 8.0 Hz, 1H), 3.69 (bd, J=7.9 Hz, 1H), 3.35 (bs, N—H), 2.88-2.80 (bm, 2H), 2.33 (s, 3H), 2.19 (bt, J=11.2 Hz, 2H), 2.12-2.05 (bm, 2H), 1.61-1.50 (bm, 2H). Analysis calc'd for C$_{19}$H$_{23}$Cl$_3$FN$_3$O: C, 52.49; H, 5.33; N, 9.66. Found: C, 52.24; H, 5.43; N, 9.27.

Example 5

2,6-Difluoro-N-(3-(1-methylpiperidin-4-ylamino)phenyl)benzamide dihydrochloride

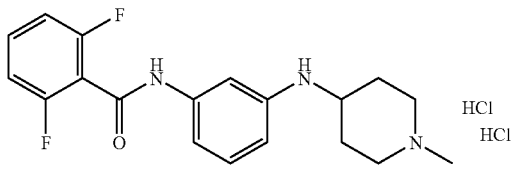

Using a method similar to Example 1, using 2,6-difluoro-N-(3-aminophenyl)benzamide (Preparation 3, 300 mg, 1.208 mmol) gives the title compound as a white solid (freebase 355 mg, 85%; dihydrochloride 411 mg): mp 198° C. (dec); mass spectrum (freebase, ion spray): m/z=346.0 (M+1), $^1$H NMR (freebase, CDCl$_3$): 7.55 (bs, N—H), 7.45-7.36 (m, 1H), 7.24 (t, J=1.9 Hz, 1H), 7.12 (t, J=8.0 Hz, 1H), 6.99 (t, J=8.1 Hz, 2H), 6.66 (dd, J=1.4 Hz, 7.8 Hz, 1H), 6.40 (dd, J=2.0 Hz, 8.0 Hz, 1H), 3.67 (bd, J=8.1 Hz, 1H), 3.34 (bs, N—H), 2.83 (bd, J=11.0 Hz, 2H), 2.32 (s, 3H), 2.18 (bt, J=11.6 Hz, 2H), 2.08 (bd, J=12.7 Hz, 2H), 1.59-1.48 (m, 2H). Analysis calc'd for C$_{19}$H$_{23}$Cl$_2$F$_2$N$_3$O: C, 54.55; H, 5.54; N, 10.04. Found: C, 54.78; H, 5.69; N, 9.78.

Example 6

2,4-Difluoro-N-(3-(1-methylpiperidin-4-ylamino)phenyl)benzamide dihydrochloride

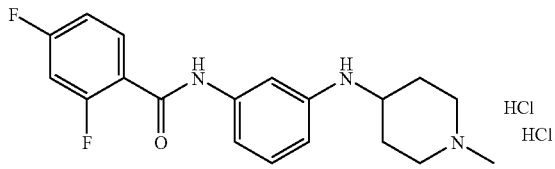

Using a method similar to Example 1, using 2,4-difluoro-N-(3-aminophenyl)benzamide (Preparation 4, 307 mg, 1.236 mmol) gives the title compound as a white solid (freebase 394 mg, 92%; dihydrochloride 394 mg): mp 262° C. (dec); mass spectrum (freebase, ion spray): m/z=346.0 (M+1), $^1$H NMR (freebase, CDCl$_3$): 8.20-8.02 (m, 2H), 7.14 (t, J=1.9 Hz, 1H), 7.05 (t, J=8.0 Hz, 1H), 7.00-6.93 (m, 1H), 6.92-6.80 (m, 1H), 6.63 (dd, J=1.3 Hz, 7.9 Hz, 1H), 6.33 (dd, J=1.9 Hz, 7.9 Hz, 1H), 3.58 (bd, J=8.1 Hz, 1H), 3.27 (bs, N—H), 2.73 (bd, J=11.8 Hz, 2H), 2.22 (s, 3H), 2.07 (bt, J=11.1 Hz, 2H), 2.01 (bd, J=12.9 Hz, 2H), 1.50-1.35 (m, 2H).

Example 7

2,4,6-Trifluoro-N-(3-(1-methylpiperidin-4-ylamino)phenyl)benzamide dihydrochloride

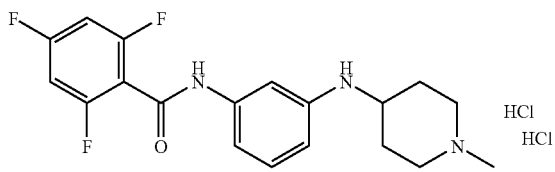

Using a method similar to Example 1, using 2,4,6-trifluoro-N-(3-aminophenyl)benzamide (Preparation 5, 290 mg, 1.089 mmol) gives the title compound as a white solid (freebase 355 mg, 90%; dihydrochloride 355 mg): mp 257° C. (dec); mass spectrum (freebase, ion spray): m/z=364.0 (M+1), $^1$H NMR (freebase, CDCl$_3$): 7.43 (bs, N—H), 7.13 (t, J=2.0 Hz, 1H), 7.05 (t, J=8.0 Hz, 1H), 6.69 (t, J=8.2 Hz, 2H), 6.57 (dd, J=1.4 Hz, 7.8 Hz, 1H), 6.33 (dd, J=1.9 Hz, 8.1 Hz, 1H), 3.59 (bd, J=8.0 Hz, 1H), 3.25 (bs, N—H), 2.72 (bd, J=11.8 Hz, 2H), 2.22 (s, 3H), 2.06 (bt, J=11.2 Hz, 2H), 2.00 (bd, J=11.7 Hz, 2H), 1.50-1.35 (m, 2H).

Example 8

2-Bromo-N-(3-(1-methylpiperidin-4-ylamino)phenyl)benzamide dihydrochloride

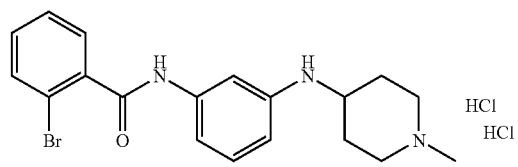

Using a method similar to Example 1, using 2-bromo-N-(3-aminophenyl)benzamide (Preparation 6, 304 mg, 1.044 mmol) gives the title compound as a white solid (free base 377 mg, 93%; dihydrochloride 395 mg): mp 192-3° C.; mass spectrum (free base, ion spray): m/z=388.1 (M+1), $^1$H NMR (free base, CDCl$_3$): 7.65-7.60 (m, 2H), 7.57 (bs, N—H), 7.40 (td, J=1.1 Hz, 7.5 Hz, 1H), 7.31 (td, J=1.7 Hz, 7.8 Hz, 1H), 7.24 (bt, J=2.1 Hz, 1H), 7.13 (t, J=8.0 Hz, 1H), 6.67 (dd, J=1.5 Hz, 7.9 Hz, 1H), 6.40 (dd, J=2.0 Hz, 8.1 Hz, 1H), 3.68 (bd, J=7.9 Hz, 1H), 3.38-3.29 (bm, 1H), 2.82 (bd, J=11.2 Hz, 2H), 2.31 (s, 3H), 2.17 (bt, J=11.2 Hz, 2H), 2.08 (bd, J=12.9 Hz, 2H), 1.58-1.47 (m, 2H). Analysis calc'd for C$_{19}$H$_{24}$BrCl$_2$N$_3$O.0.25H$_2$O: C, 49.00; H, 5.30; N, 9.02. Found: C, 49.11; H, 5.36; N, 8.69.

Example 9

2-Chloro-N-(3-(1-methylpiperidin-4-ylamino)phenyl)benzamide dihydrochloride

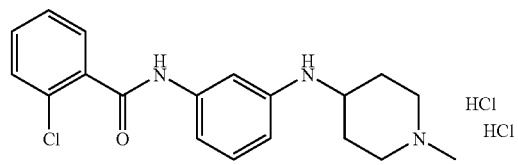

Using a method similar to Example 1, using 2-chloro-N-(3-aminophenyl)benzamide (Preparation 7, 300 mg, 1.216 mmol) gives the title compound as a white solid (free base 331 mg, 79%; dihydrochloride 333 mg): mp 206-8° C.; mass spectrum (free base, ion spray): m/z=344.0 (M+1), $^1$H NMR (free base, CDCl$_3$): 7.75 (bs, N—H), 7.73 (dd, J=2.0 Hz, 7.3 Hz, 1H), 7.46-7.34 (m, 3H), 7.25 (bt, J=2.1 Hz, 1H), 7.13 (t, J=8.1 Hz, 1H), 6.68 (dd, J=1.3 Hz, 7.9 Hz, 1H), 6.40 (dd, J=2.0 Hz, 8.2 Hz, 1H), 3.67 (bd, J=7.7 Hz, 1H), 3.39-3.29 (bm, 1H), 2.83 (bd, J=11.0 Hz, 2H), 2.32 (s, 3H), 2.18 (bt, J=11.5 Hz, 2H), 2.09 (bd, J=12.5 Hz, 2H), 1.59-1.48 (bm, 2H). Analysis calc'd for $C_{19}H_{24}Cl_3N_3O \cdot 0.5H_2O$: C, 53.60; H, 5:92; N, 9.87. Found: C, 53.94; H, 5.91; N, 9.70.

Example 10

2-Trifluoromethoxy-N-(3-(1-methylpiperidin-4-ylamino)phenyl)benzamide dihydrochloride

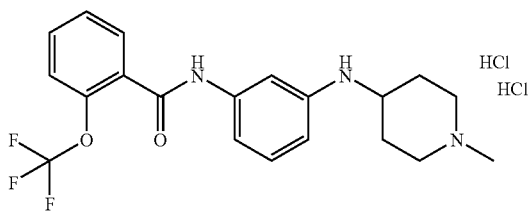

Using a method similar to Example 1, using 2-trifluoromethoxy-N-(3-aminophenyl)benzamide (Preparation 8, 300 mg, 1.013 mmol) gives the title compound as a white solid (free base 274 mg, 69%; dihydrochloride 325 mg): mp 159-62° C.; mass spectrum (free base, ion spray): m/z=394.2 (M+1), $^1$H NMR (free base, CDCl$_3$): 8.18 (bs, N—H), 8.07 (d, J=7.5 Hz, 1H), 7.55 (t, J=7.5 Hz, 1H), 7.45 (t, J=7.5 Hz, 1H), 7.34 (d, J=8.0 Hz, 1H), 7.21 (bs, 1H), 7.13 (t, J=8.0 Hz, 1H), 6.68 (d, J=7.5 Hz, 1H), 6.41 (d, J=7.5 Hz, 1H), 3.67 (bd, J=7.1 Hz, 1H), 3.38-3.28 (bm, 1H), 2.81 (bd, J=9.5 Hz, 2H), 2.30 (s, 3H), 2.22-2.04 (bm, 4H), 1.58-1.46 (bm, 2H).

Example 11

2,6-Difluoro-N-(3-(N-methyl-N-(1-methylpiperidin-4-yl)amino)phenyl)benzamide dihydrochloride

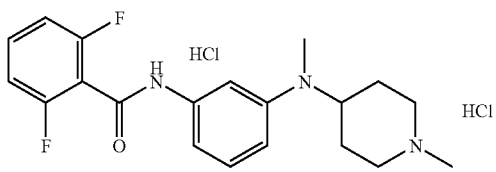

Combine 1-methyl-4-(N-(3-aminophenyl)-N-methylamino)piperidine (Preparation 11, 101 mg, 0.307 mmol), dichloromethane (6 mL) and pyridine (0.125 mL, 1.535 mmol) at 0° C. Add 2,6-difluorobenzoyl chloride (0.048 mL, 0.384 mmol) neat and continue stirring for 1 hr. Dilute with dichloromethane (5 mL) and wash with sodium hydroxide (1N aq., 2×8 mL). Combine the organic layers, dry over magnesium sulphate, filter under reduced pressure and concentrate to dryness. Purify by flash chromatography, eluting with a 20/1 mixture of dichloromethane/(2N ammonia in methanol) to give the free base of the title compound (88 mg, 80%). Following a salt formation method similar to that described in Example 1 gives the title compound as a yellow solid (89 mg): mass spectrum (free base, ion spray): m/z=360.1 (M+1), $^1$H NMR (free base, CDCl$_3$): 7.56 (bs, 1H), 7.44-7.34 (m, 2H), 7.20 (t, J=8.2 Hz, 1H), 7.00 (t, J=8.2 Hz, 2H), 6.78 (d, J=8.0 Hz, 1H), 6.59 (dd, J=2.2 Hz, 8.2 Hz, 1H), 3.71-3.63 (bm, 1H), 3.14-3.04 (bm, 2H), 2.82 (s, 3H), 2.41 (bs, 3H), 2.11-1.97 (bm, 2H), 1.79 (bd, J=13 Hz, 2H).

Example 12

2-Chloro-4-fluoro-N-(3-(N-methyl-N-(1-methylpiperidin-4-yl)amino)phenyl)benzamide dihydrochloride

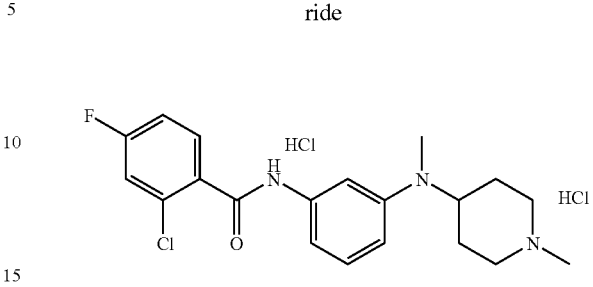

Using a method similar to Example 11, using 2-chloro-4-fluorobenzoyl chloride (0.049 mL, 0.384 mmol) gives the title compound (free base 102 mg, 89%; dihydrochloride 67 mg, white solid): mp 172° C.; mass spectrum (free base, ion spray): m/z=376.1 (M+1), $^1$H NMR (free base, CDCl$_3$): 7.80-7.76 (m, 2H), 7.30 (bs, N—H), 7.22-7.18 (m, 2H), 7.09 (td, J=2.4 Hz, 8.1 Hz, 1H), 6.80 (d, J=8.0 Hz, 1H), 6.60 (dd, J=2.1 Hz, 8.4 Hz, 1H), 3.68-3.58 (m, 1H), 3.03 (bd, J=11.0 Hz, 2H), 2.82 (s, 3H), 2.36 (s, 3H), 2.23-2.15 (bm, 2H), 2.01-1.89 (bm, 2H), 1.76 (bd, J=12.0 Hz, 2H). Analysis calc'd for $C_{20}H_{25}Cl_3FN_3O \cdot 0.25H_2O$: C, 53.53; H, 5.61; N, 9.36. Found: C, 53.19; H, 5.79; N, 9.36.

Example 13

2,4,6-Trifluoro-N-(3-(N-methyl-N-(1-methylpiperidin-4-yl)amino)phenyl)benzamide dihydrochloride

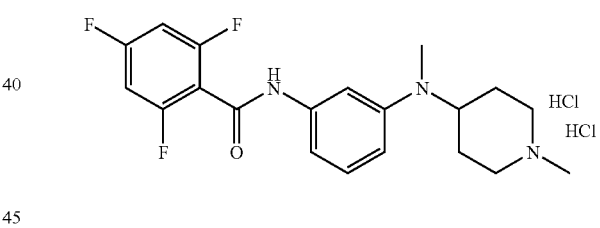

Load 1-methyl-4-(N-(3-aminophenyl)-N-methylamino)piperidine trihydrochloride (Preparation 11, 240 mg, 1.094 mmol) in methanol (2 ml) onto a SCX column (2 g cartridge, Varian). Elute with ammonia (2.0 M in methanol) to obtain the corresponding free base. Concentrate to dryness. Dissolve the resulting brown oil in dioxane (2 mL) and divide the solution into two aliquots (2×1 mL). Take one of the aliquots and add dioxane (1 mL). Add 2,4,6-trifluoro-benzoyl chloride (0.052 mL, 0.401 mmol) neat. Shake and heat at 106.5° C. for 2 hr. Cool to ambient temperature and load onto a SCX column (1 g cartridge, Varian). Elute with ammonia (2.0 M in methanol). Purify further by flash chromatography using 20/1 mixture of dichloromethane and 2.0 M ammonia in methanol to provide the free base of the title compound (86 mg, 62%). Following a salt formation method similar to Example 1 gives the title compound as a white solid (99 mg): mp 199-200° C.; mass spectrum (free base, ion spray): m/z=378.2 (M+1), $^1$H NMR (free base, CDCl$_3$): 7.44 (bs, N—H), 7.31 (bs, 1H), 7.19 (t, J=8.3 Hz, 1H), 6.80-6.73 (m, 3H), 6.60 (dd, J=2.2 Hz, 8.3 Hz, 1H), 3.64 (tt, J=4.0 Hz, 11.9 Hz, 1H), 3.05 (bd, J=10.8 Hz, 2H), 2.81 (s, 3H), 2.38 (s, 3H), 2.28-2.17 (bm, 2H), 2.06-1.92 (bm, 2H), 1.76 (bd, J=12.2 Hz, 2H).

Example 14

2-Chloro-6-fluoro-N-(3-(N-methyl-N-(1-methylpiperidin-4-yl)amino)phenyl)benzamide dihydrochloride

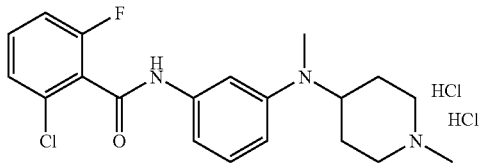

Using a method similar to Example 13, using 2-chloro-6-fluorobenzoyl chloride (0.052 mL, 0.401 mmol) gives the title compound as a white solid (free base 100 mg, 73%; dihydrochloride 114 mg): mp 214-7° C.; mass spectrum (free base, ion spray): m/z=376.2 (M+1), $^1$H NMR (free base, CDCl$_3$): 7.44 (bs, N—H), 7.39-7.32 (m, 2H), 7.27-7.24 (m, 1H), 7.21 (t, J=8.1 Hz, 1H), 7.09 (t, J=8.5 Hz, 1H), 6.80 (d, J=8.1 Hz, 1H), 6.60 (dd, J=2.3 Hz, 8.4 Hz, 1H), 3.72-3.63 (m, 1H), 3.09 (bd, J=10.1 Hz, 2H), 2.82 (s, 3H), 2.41 (s, 3H), 2.33-2.22 (bm, 2H), 2.12-1.99 (bm, 2H), 1.79 (bd, J=11.9 Hz, 2H). Analysis calculated for C$_{20}$H$_{25}$Cl$_3$FN$_3$O: C, 53.53; H, 5.61; N, 9.36. Found: C, 53.85; H, 5.72; N, 8.99.

Preparation 56

4-(3-(2-Chloro-4-fluorobenzoylamino)phenylamino)piperidine-1-carboxylic acid t-butyl ester

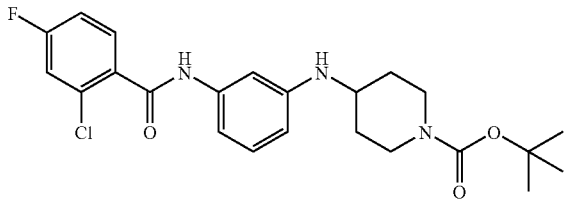

Using a method similar to Example 1, using 1-t-butoxycarbonyl-4-piperidone (158 mg, 0.793 mmol) gives the title free base compound (288 mg, 97%) as an off-white foam: mass spectrum (ion spray): m/z=446.2 (M−1); $^1$H NMR (CDCl$_3$): 7.81 (bs, N—H), 7.76 (dd, J=6.1 Hz, 8.4 Hz, 1H), 7.27 (bs, 1H), 7.19 (dd, J=2.3 Hz, 8.4 Hz, 1H), 7.15 (t, J=8.0 Hz, 1H), 7.09 (td, J=2.3 Hz, 8.2 Hz, 1H), 6.72 (bd, J=7.7 Hz, 1H), 6.45 (bd, J=8.0 Hz, 1H), 4.09-3.99 (bm, 1H), 3.50-3.41 (bm, 1H), 2.92 (bt, J=11.7 Hz, 2H), 2.09-2.01 (bm, 2H), 1.46 (s, 9H), 1.71-1.54 (bm, 2H), 1.39-1.33 (bm, 2H).

Example 15

2-Chloro-4-fluoro-N-(3-(piperidin-4-ylamino)phenyl)benzamide dihydrochloride

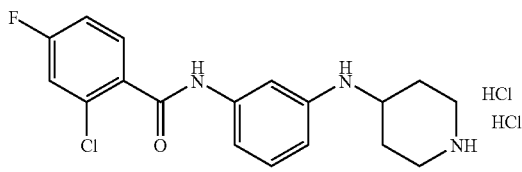

Combine acetyl chloride (5 ml) and dried methanol (10 ml) at 0° C. under a nitrogen atmosphere. Stir for 1 hr. at 0° C. Add a solution of 4-(3-(2-Chloro-4-fluorobenzoylamino) phenylamino)piperidine-1-carboxylic acid t-butyl ester (Preparation 56, 72 mg, 0.161 mmol) in methanol (2 mL). Stir overnight. Concentrate under reduced pressure. Triturate with diethyl ether (1 mL) to provide a pale yellow foam of the title compound: mp 255-7° C.; mass spectrum (ion spray): m/z=348.2 (M+1). Analysis calc'd for C$_{18}$H$_{21}$Cl$_3$FN$_3$O.1.0H$_2$O: C, 49.28; H, 5.28; N, 9.58. Found: C, 49.15; H, 4.96; N, 9.56.

Example 16

2-Chloro-N-(3-(N-methyl-N-(1-methylpiperidin-4-yl)amino)phenyl)benzamide dihydrochloride

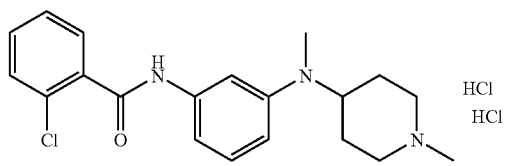

Combine 2-chloro-N-(3-(1-methylpiperidin-4-ylamino)phenyl)benzamide dihydrochloride (Example 9, 100 mg, 0.240 mmol), methanol (3 mL) and formaldehyde (37% aq., 0.195 mL, 2.39 mmol). Stir at room temperature for 45 min. Cool to 0° C. Add acetic acid (0.412 mL, 7.20 mmol) and sodium cyanoborohydride (26 mg, 0.420 mmol). Stir at room temperature overnight. Concentrate to dryness. Dissolve the residue in a 2/1 mixture of ethyl acetate and hexanes (8 mL) and wash with sodium hydroxide (1N aq., 2×6 mL). Separate the organic layer and dry over magnesium sulfate. Filter and concentrate under reduced pressure. Purify through flash chromatography eluting with a 20/1 mixture of dichloromethane and 2M ammonia in methanol to provide the free base of the title compound (69 mg, 80%). Following a salt formation method similar to Example 1 gives the title compound as a white solid (83 mg, white solid): mass spectrum (free base, ion spray): m/z=358.2 (M+1), $^1$H NMR (free base, CDCl$_3$): 7.97 (bs, N—H), 7.66 (dd, J=1.7 Hz, 7.5 Hz, 1H), 7.42-7.27 (m, 4H), 7.17 (t, J=8.2 Hz, 1H), 6.82 (dd, J=1.5 Hz, 8.2 Hz, 1H), 6.57 (dd, J=2.3 Hz, 8.4 Hz, 1H), 3.59 (tt, J=3.9 Hz, 11.7 Hz, 1H), 2.90 (bd, J=11.7 Hz, 2H), 2.78 (s, 3H), 2.26 (s, 3H), 2.05 (td, J=2.3 Hz, 12.0 Hz, 2H), 1.82 (qd, J=3.9 Hz, 12.0 Hz, 2H), 1.70 (bd, J=12.0 Hz, 2H). Analysis calc'd for C$_{20}$H$_{26}$Cl$_3$N$_3$O 0.25H$_2$O: C, 55.18; H, 6.14; N, 9.65. Found: C, 55.03; H, 6.11; N, 9.26.

Example 17

2-Bromo-N-(3-(N-methyl-N-(1-methylpiperidin-4-yl)amino)phenyl)benzamide dihydrochloride

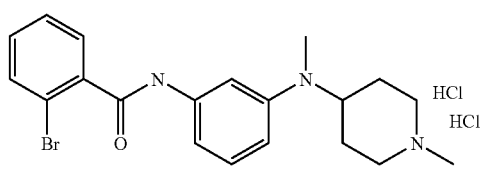

Using a method similar to Example 16, using 2-bromo-N-(3-(1-methylpiperidin-4-ylamino)phenyl)benzamide dihydrochloride (Example 8, 100 mg, 0.217 mmol) gives the title compound as a white solid (free base 62 mg, 71%; dihydrochloride 73 mg): mp 196-7° C.; mass spectrum (free base, ion spray): m/z=402.2 (M+1), $^1$H NMR (free base, CDCl$_3$): 7.76 (bd, J=11.3 Hz, N—H), 7.66-7.57 (m, 2H), 7.42-7.16 (m, 4H), 6.88-6.81 (m, 1H), 6.63-6 56 (m, 1H), 3.67-3.55 (bm, 1H), 2.98-2.89 (bm, 2H), 2.79 (bs, 3H), 2.27 (bs, 3H), 2.13-2.02 (bm, 2H), 1.92-1.78 (bm, 2H), 1.77-1.68 (bm, 2H). Analysis calc'd for C$_{20}$H$_{26}$BrCl$_2$N$_3$O.0.5H$_2$O: C, 49.61; H, 5.62; N, 8.68. Found: C, 49.84; H, 5.85; N, 8.36.

Example 18

2,4-Difluoro-N-(3-(N-methyl-N-(1-methylpiperidin-4-yl)amino)phenyl)benzamide dihydrochloride

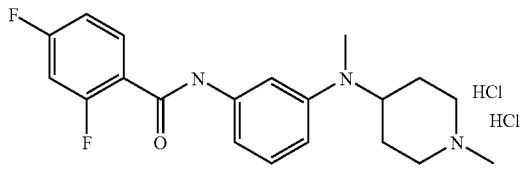

Using a method similar to Example 16, using 2,4-difluoro-N-(3-(1-methylpiperidin-4-ylamino)phenyl)benzamide dihydrochloride (Example 6, 100 mg, 0.239 mmol) gives the title compound as a white solid (free base 79 mg, 92%; dihydrochloride 94 mg): mp 165-8° C.; mass spectrum (free base, ion spray): m/z=360.3 (M+1), $^1$H NMR (free base, CDCl$_3$): 8.28 (bd, J=13.8 Hz, N—H), 8.21-8.12 (bm, 1H), 7.29-7.23 (bm, 1H), 7.19 (t, J=8.2 Hz, 1H), 7.06-6.77 (bm, 3H), 6.60 (d, J=7.9 Hz, 1H), 3.65-3.53 (bm, 1H), 2.99-2.88 (bm, 2H), 2.81 (bs, 3H), 2.30 (bs, 3H), 2.09 (bt, J=11.0 Hz, 2H), 1.92-1.78 (bm, 2H), 1.73 (bd, J=11.0 Hz, 2H). Analysis calc'd for C$_{20}$H$_{25}$Cl$_2$F$_2$N$_3$O: C, 55.56; H, 5.83; N, 9.72. Found: C, 55.62; H, 5.95; N, 9.69.

Preparation 57

4-(N-(3-(2-Chloro-4-fluorobenzoylamino)phenyl)methylamino)piperidine-1-carboxylic acid t-butyl ester

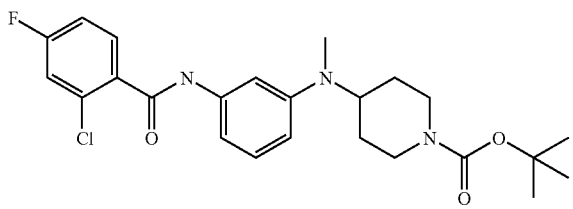

Using a method similar to Example 16, using 4-(3-(2-chloro-4-fluorobenzoylamino)phenylamino)piperidine-1-carboxylic acid t-butyl ester (Preparation 56, 165 mg, 0.368 mmol) gives the title free base compound (169 mg, 99%): mass spectrum (ion spray): m/z=462.2 (M+1). $^1$H NMR (CDCl$_3$): 8.13 (bs, N—H), 7.67 (dd, J=6.0 Hz, 8.6 Hz, 1H), 7.31 (bt, J=2.0 Hz, 1H), 7.18 (t, J=8.2 Hz, 1H), 7.13 (dd, J=2.3 Hz, 8.6 Hz, 1H), 7.01 (td, J=2.3 Hz, 8.2 Hz, 1H), 6.83 (bd, J=8.0 Hz, 1H), 6.59 (dd, J=2.3 Hz, 8.4 Hz, 1H), 4.24-4.14 (bm, 2H), 3.72 (tt, J=3.8 Hz, 11.5 Hz, 1H), 2.76-2.73 (m, 5H), 1.74-1.56 (bm, 4H), 1.45 (s, 9H).

Example 19

2-Chloro-4-fluoro-N-(3-(N-piperidin-4-yl)methylamino)phenyl)benzamide dihydrochloride

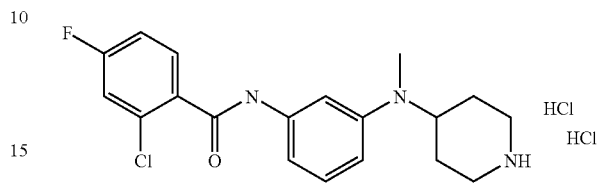

Using a method similar to Example 15, using 4-(N-(3-(2-Chloro-4-fluorobenzoylamino)phenyl)methylamino)piperidine-1-carboxylic acid t-butyl ester (Preparation 57, 169 mg, 0.366 mmol) gives the title compound as an off-white solid: mass spectrum (ion spray): m/z=362.1 (M+1); $^1$H NMR (free base, CDCl$_3$): 7.84 (bs, N—H), 7.68 (dd, J=6.1 Hz, 8.6 Hz, 1H), 7.21-7.19 (m, 1H), 7.15-7.09 (m, 2H), 7.00 (td, J=2.3 Hz, 8.2 Hz, 1H), 6.75 (bd, J=8.0 Hz, 1H), 6.54 (dd, J=2.1 Hz, 8.4 Hz, 1H), 3.68-3.59 (bm, 1H), 3.25-3.08 (bm, 2H), 2.74 (s, 3H), 2.73-2.62 (bm, 2H), 1.81-1.60 (bm, 4H). Analysis calc'd for C$_{19}$H$_{23}$Cl$_3$FN$_3$O.0.1H$_2$O: C, 52.27; H, 5.36; N, 9.63. Found: C, 52.60; H, 5.75; N, 9.29.

Example 20

2-Chloro-4-fluoro-N-(3-(1-ethylpiperidin-4-ylamino)phenyl)benzamide dihydrochloride

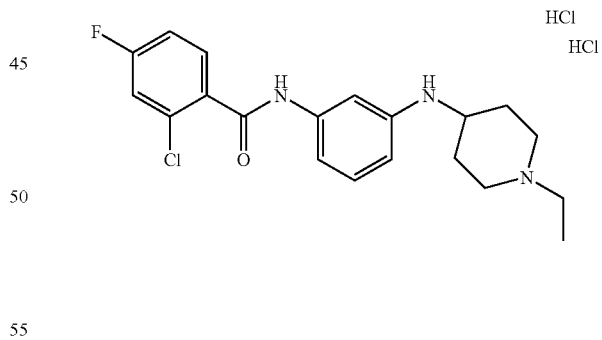

Using a method similar to Example 1, using 1-ethylpiperidin-4-one (0.102 mL, 0.756 mmol) gives the title compound as a white solid (143 mg, 50%): mass spectrum (free base, ion spray): m/z=376.1 (M+1); $^1$H NMR (free base, CDCl$_3$): 7.77 (bs, N—H), 7.76 (dd, J=6.1 Hz, 8.7 Hz, 1H), 7.21 (d, J=2.1 Hz, 1H), 7.18 (dd, J=2.5 Hz, 8.3 Hz, 1H), 7.12 (t, J=8.1 Hz, 1H), 7.08 (td, J=2.5 Hz, 8.3 Hz, 1H), 6.67 (bd, J=8.0 Hz, 1H), 6.40 (dd, J=2.0 Hz, 8.1 Hz, 1H), 3.67 (bd, J=8.0 Hz, 1H), 3.39-3.29 (bm, 1H), 2.92-2.85 (bm, 2H), 2.42 (q, J=7.2 Hz, 2H), 2.16-2.05 (bm, 4H), 1.55-1.44 (bm, 2H), 1.09 (t, J=7.2 Hz, 3H).

Example 21

2-Chloro-4-fluoro-N-(3-(1-propylpiperidin-4-ylamino)phenyl)benzamide dihydrochloride

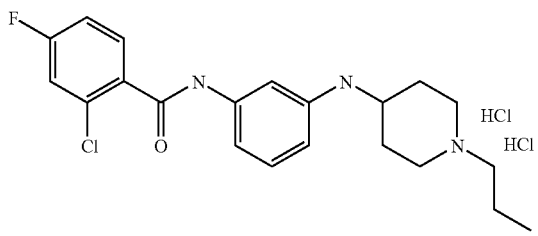

Using a method similar to Example 1, using 1-propylpiperidin-4-one (0.114 mL, 0.756 mmol) gives the title compound as a white solid (262 mg, 89%): mass spectrum (free base, ion spray): m/z=390.2 (M+1); $^1$H NMR (free base, CDCl$_3$): 7.89 (bs, N—H), 7.71 (dd, J=6.0 Hz, 8.7 Hz, 1H), 7.19 (bt, J=2.0 Hz, 1H), 7.16 (dd, J=2.5 Hz, 8.6 Hz, 1H), 7.11 (t, J=8.0 Hz, 1H), 7.05 (td, J=2.5 Hz, 8.1 Hz, 1H), 6.68 (bd, J=8.0 Hz, 1H), 6.39 (dd, J=2.0 Hz, 8.0 Hz, 1H), 3.67 (bd, J=7.8 Hz, 1H), 3.36-3.26 (bm, 1H), 2.86 (bd, J=11.6 Hz, 2H), 2.32-2.27 (m, 2H), 2.14-2.02 (bm, 4H), 1.56-1.43 (bm, 4H), 0.89 (t, J=7.4 Hz, 3H).

Example 22

2-Chloro-4-fluoro-N-(3-(N-(1-propylpiperidin-4-yl)methylamino)phenyl)benzamide dihydrochloride

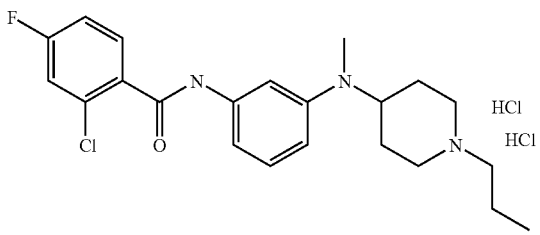

Using a method similar to Example 16, using 2-chloro-4-fluoro-N-(3-(1-propylpiperidin-4-ylamino)phenyl)benzamide dihydrochloride (Example 21, 71 mg, 0.153 mmol) gives the title compound as a white solid (43 mg, 69%): mass spectrum (free base, ion spray): m/z=404.1 (M+1); $^1$H NMR (free base, CDCl$_3$): 7.87 (bs, N—H), 7.64 (dd, J=6.1 Hz, 8.6 Hz, 1H), 7.20 (s, 1H), 7.14-7.07 (m, 2H), 6.97 (td, J=2.3 Hz, 8.2 Hz, 1H), 6.75 (d, J=8.2 Hz, 1H), 6.51 (dd, J=2.1 Hz, 8.6 Hz, 1H), 3.54 (tt, J=3.8 Hz, 11.7 Hz, 1H), 2.97 (bd, J=11.4 Hz, 2H), 2.73 (s, 3H), 2.27-2.22 (m, 2H), 1.98 (bt, J=11.7 Hz, 2H), 1.80 (bqd, J=3.5 Hz, 12.5 Hz, 2H), 1.66 (bd, J=11.7 Hz, 2H), 1.51-1.41 (m, 2H), 0.83 (t, J=7.4 Hz, 3H).

Example 23

2-Chloro-4-fluoro-N-(3-(N-(1-(2-(1-isopropyl-1H-pyrazol-4-yl)ethyl)piperidin-4-yl)methylamino)phenyl)benzamide dihydrochloride

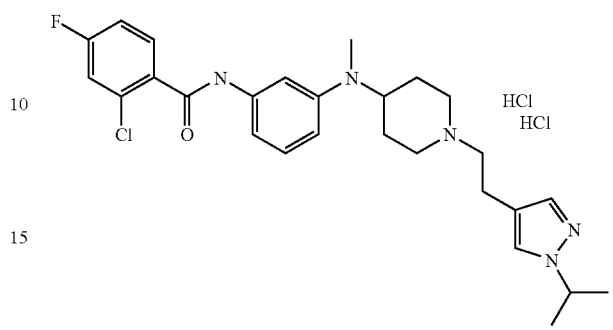

Combine 1-isopropyl-2-hydroxyethyl-1H-pyrazole (Preparation 10, 2 g, 12.9 mmol), and triethylamine (3.6 mL, 25.9 mmol) in 30 mL of THF. Add methanesulfonyl chloride (1.3 mL, 15.6 mmol) and stir for 36 hr. Dilute with water and ethyl acetate. Separate and extract the aqueous layer with CH$_2$Cl$_2$ (2 times). Combine organics, dry over MgSO$_4$, and concentrate in vacuo. Take a portion of this crude mixture (55 mg, 0.237 mmol) and combine with 2-Chloro-4-fluoro-N-(3-(N-piperidin-4-yl)methylamino)phenyl)benzamide dihydrochloride (Example 19, 78 mg, 0.179 mmol), potassium carbonate (99 mg, 0.716 mmol) and acetonitrile (3 mL). Stir and heat at 80° C. overnight. Cool to room temperature and filter through a silica plug. Concentrate the filtrate. Purify through flash chromatography eluting with a 20/1 mixture of CH$_2$Cl$_2$ and 2.0 M ammonia in methanol. Dissolve the residue in diethyl ether and treat with ethereal hydrogen chloride. Triturate the resulting gum with ether to give the title compound as an off-white solid (53 mg, 60%): mass spectrum (free base, ion spray): m/z=498.1 (M+1); $^1$H NMR (free base, CDCl$_3$): 7.79 (bs, N—H), 7.78 (dd, J=6.0 Hz, 8.7 Hz, 1H), 7.35 (s, 1H), 7.29 (bs, 1H), 7.24 (s, 1H), 7.23-7.18 (m, 2H), 7.09 (td, J=2.5 Hz, 8.2 Hz, 1H), 6.80 (bd, J=7.8 Hz, 1H), 6.61 (dd, J=2.3 Hz, 8.3 Hz, 1H), 4.44 (septet, J=6.4 Hz, 1H), 3.69-3.60 (bm, 1H), 3.11 (bd, J=11.0 Hz, 2H), 2.83 (s, 3H), 2 71-2.64 (bm, 2H), 2.60-2.55 (bm, 2H), 2.21-2.11 (bm, 2H), 1.94-1.83 (bm, 2H), 1.81-1.74 (bm, 2H), 1.48 (d, J=6.4 Hz, 6H).

Example 24

2-Chloro-4-fluoro-N-(3-(1-methylpiperidin-4-ylamino)-4-fluorophenyl)benzamide hydrochloride

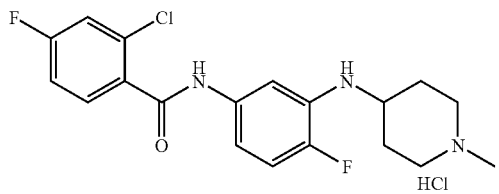

Under an inert atmosphere, stir a mixture of 2-chloro-4-fluoro-N-(3-amino-4-fluorophenyl)benzamide (Preparation 14, 481 mg, 1.7 mmol), 1-methyl-4-piperidone (384 mg, 0.42 mL, 3.4 mmol), 1,2-dichloroethane (15 mL), powdered molecular sieves 4 Å (1 g) for 15 min. Add glacial acetic acid (306 mg, 0.3 mL, 5.1 mmol). After 1 hr., add sodium triacetoxyborohydride (900 mg, 4.25 mmol). Allow the reaction to go overnight. Pour the reaction mixture into ethyl acetate (200 mL), and wash once with aqueous NaOH (2N, 30 mL). Separate the organic layer, dry over anhydrous sodium sulfate, remove the solvent under reduced pressure. Further purify the residue by chromatography on silica gel using a 4%-6% gradient of (2M $NH_3$ in methanol) in $CH_2Cl_2$ to obtain the free base of the title compound (443 mg, 69% yield). Convert the product to its HCl salt by dissolving it in $CH_2Cl_2$ and treating with excess 1.0M HCl in diethyl ether. Add more ether to precipitate the title compound as a white solid: mass spectrum (ion spray): m/z=380.2 (M+1); Analysis calculated $C_{19}H_{20}ClF_2N_3O \cdot HCl \cdot H_2O$: C, 52.54; H, 5.34; N, 9.68. Found: C, 52.93; H, 5.29; N, 9.65; LY 653915: $^1$H NMR δ (methanol-d) 7.72 (dd, 1H), 7.60 (m, 1H), 7.37 (dd, 1H), 7.14 (m, 3H), 3.74 (m, 1H), 3.62 (d, 2H), 3.30 (dd, 2H), 2.88 (s, 3H), 2.36 (d, 2H), 1.93 (m, 2H)

Example 25

2,4-Difluoro-N-(3-(1-methylpiperidin-4-ylamino)-4-fluorophenyl)benzamide hydrochloride

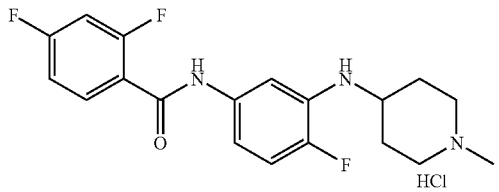

Using a procedure similar Example 24 using 2,4-difluoro-N-(3-amino-4-fluorophenyl)benzamide (Preparation 16, 452 mg, 1.7 mmol), 1-methyl-4-piperidone (384 mg, 0.42 mL, 3.4 mmol), 1,2-dichloroethane (15 mL), powdered molecular sieves 4 Å (1 g), glacial acetic acid (306 mg, 0.3 mL, 5.1 mmol), sodium triacetoxyborohydride (900 mg, 4.25 mmol) to obtain the free base of the title compound (434 mg, 70% yield) and the title compound: mass spectrum (ion spray): m/z=364.1 (M+1); analysis calculated for $C_{19}H_{20}F_3N_3O \cdot HCl \cdot H_2O$: C, 54.61; H, 5.55; N, 10.06. Found: C, 54.48; H, 5.36; N, 9.93; $^1$H NMR δ (methanol-$d_4$) 7.79 (m, 1H), 7.63 (d, 1H), 7.11 (m, 4H), 3.74 (m, 1H), 3.62 (d, 2H), 3.30 (dd, 2H), 2.88 (s, 3H), 2.36 (d, 2H), 1.93 (m, 2H)

Example 26

3-Methyl-N-(3-(1-methylpiperidin-4-ylamino)phenyl)butyramide hydrochloride

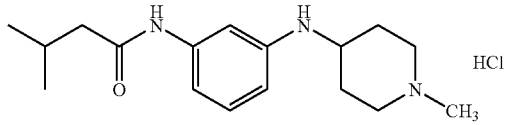

Combine 1-methyl-4-(3-aminophenylamino)piperidine triacetate (Preparation 18, 460 mg, 1.17 mmol) and $CH_2Cl_2$ (13 mL); stir and cool to 0° C. Add isovaleryl chloride (135 μL, 1.05 mmol), and stir at room temperature for 18 hr. Load onto a 5 g SCX cartridge (mega bond elut, Varian). Wash resin with methanol, then elute product with 2 M ammonia in methanol. Concentrate in vacuo, and chromatograph on silica gel, eluting with a gradient of 1-15% (2M ammonia in methanol) in $CH_2Cl_2$. Concentrate in vacuo. Dissolve the purified oil (115 mg, 38% isolated yield) in methanol, add solid $NH_4Cl$ (21.2 mg, 1 eq) and sonicate the solution at room temperature for 15 min. Concentrate in vacuo to provide the title compound: mass spectrum (ion spray): m/z=290.2 (M+1); Anal calculated for $C_{17}H_{28}ClN_3O \cdot 0.1H_2O$: Theory: C, 62.31; H, 8.67; N, 12.82. Found: C, 62.32; H, 8.78; N, 12.56.

Example 27

4-Fluoro-N-(3-(1-methyl-piperidin-4-ylamino)phenyl)benzamide hydrochloride

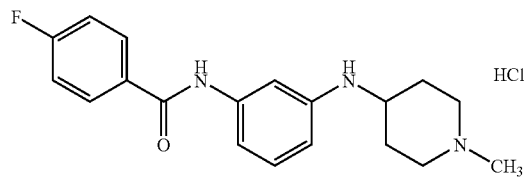

A method similar to Example 26, using 4-fluorobenzoyl chloride, gives the title compound as a white solid (127 mg): mass spectrum (ion spray): m/z=328.1 (M+1); Anal calc'd for $C_{19}H_{23}ClFN_3O \cdot 0.1H_2O$: Theory: C, 62.41; H, 6.39; N, 11.49. Found: C, 62.13; H, 6.55; N, 11.14.

Example 28

Cyclopropane-N-(3-(1-methyl-piperidin-4-ylamino)phenyl)carboxamide hydrochloride

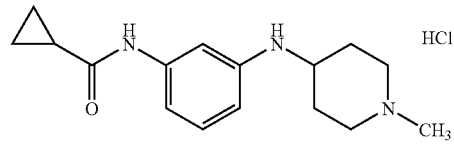

A method similar to Example 26, using cyclopropanecarbonyl chloride, gives the title compound as a white solid (80 mg): mass spectrum (ion spray): m/z=274.1 (M+1); Anal calc'd for $C_{16}H_{24}ClN_3O \cdot 0.1H_2O$: Theory: C, 58.62; H, 7.99; N, 12.82. Found: C, 58.47; H, 8.00; N, 12.73.

Example 29

2-Methyl-N-(3-(1-methyl-piperidin-4-ylamino)phenyl)benzamide hydrochloride

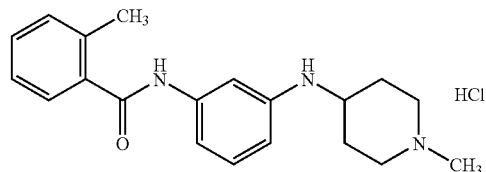

A method similar to Example 26, using 2-methylbenzoyl chloride, gives the title compound as a white solid (32 mg): mass spectrum (ion spray): m/z=324.2 (M+1); $^1$H NMR δ (DMSO, ppm) 10.02 (s, 1H), 7.37 (m, 1H), 7.25 (m, 4H), 7.02 (t, J=8.1, 16.1 Hz, 1H), 6.82 (d, J=7.7 Hz, 1H), 6.34 (d, J=8.4

Hz, 1H), 5.76 (m, 1H), 3.40 (m, 2H), 3.11 (bs, 2H), 2.71 (s, 3H), 2.36 (s, 3H), 2.29 (s, 1H), 2.05 (m, 2H), 1.70 (m, 2H)

Example 30

N-(3-(1-Methyl-piperidin-4-ylamino)phenyl)isonicotinamide

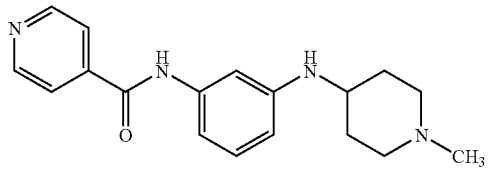

A method similar to Example 26, but not making the HCl salt, using isonicotinyl chloride, gives the title compound as a yellow oil (30 mg): mass spectrum (ion spray): m/z=310.0 (M+1).

Example 31

2,6-Dichloro-N-(3-(1-methyl-piperidin-4-ylamino)phenyl)benzamide hydrochloride

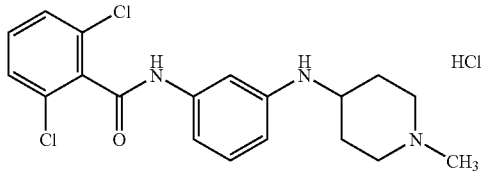

A method similar to Example 26, using 2,6-dichlorobenzoyl chloride, gives the title compound as a white solid (174 mg): mass spectrum (ion spray): m/z=378.0 (M+1); $^1$H NMR δ (DMSO, ppm) 10.45 (s, 1H), 7.52 (m, 2H), 7.22 (m, 2H), 7.05 (t, J=8.1, 16.1 Hz, 1H), 6.76 (d, J=8.1 Hz, 1H), 6.38 (d, J=8.1 Hz, 1H), 5.84 (d, J=7.0 Hz, 1H), 3.40 (m, 2H), 3.17 (bs, 2H), 2.72 (s, 3H), 2.30 (s, 1H), 2.06 (m, 2H), 1.69 (m, 2H).

Example 32

N-(3-(1-Methyl-piperidin-4-ylamino)phenyl)-2-trifluoromethyl-benzamide hydrochloride

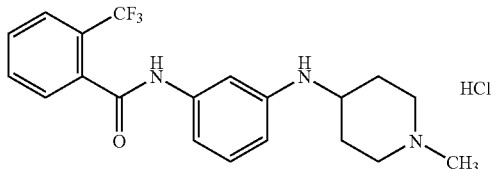

A method similar to Example 26, using 2-trifluoromethylbenzoyl chloride, gives the title compound as a white solid (147 mg): mass spectrum (ion spray): m/z=378.1 (M+1); $^1$H NMR δ (DMSO, ppm) 10.29 (s, 1H), 7.75 (m, 2H), 7.21 (m, 3H), 7.04 (t, J=8.1, 16.1 Hz, 1H), 6.77 (d, J=7.7 Hz, 1H), 6.37 (d, J=7.7 Hz, 1H), 5.81 (d, J=7.3 Hz, 1H), 3.40 (m, 2H), 3.10 (bs, 2H), 2.72 (s, 3H), 2.30 (s, 1H), 2.06 (m, 2H), 1.71 (m, 2H).

Example 33

4-Fluoro-N-(3-(1-methyl-piperidin-4-ylamino)phenyl)-2-trifluoromethyl-benzamide hydrochloride

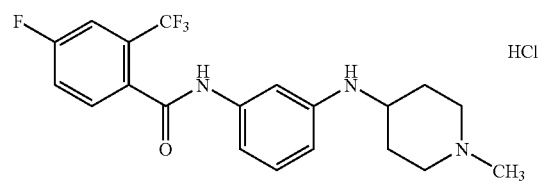

A method similar to Example 26, using 4-fluoro-2-trifluoromethylbenzoyl chloride, gives the title compound as a white solid (174 mg): mass spectrum (ion spray): m/z=396.1 (M+1); Anal calc'd for $C_{20}H_{22}ClF_4N_3O \cdot 0.5H_2O$: Theory: C, 54.49; H, 5.26; N, 9.53. Found: C, 54.88; H, 5.56; N, 9.89.

Example 34

2,6-Dichloro-(3-(methyl-(1-methyl-piperidin-4-yl)-amino)phenyl)benzamide hydrochloride

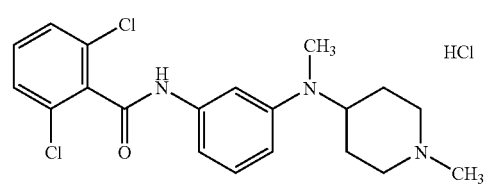

Dissolve 2,6-dichloro-N-(3-(1-methyl-piperidin-4-ylamino)phenyl)benzamide hydrochloride (Example 31, 168 mg, 0.40 mmol) in 5 mL of methanol. Add an excess of 50% aqueous formaldehyde solution (600 μL), and stir the reaction for 0.5 hr. Adjust the solution to pH=5 by the addition of acetic acid, add sodium cyanoborohydride (100 mg), and stir the reaction for an additional 18 hr. Load onto a 5 g SCX cartridge (mega bond elut, Varian). Wash the resin with methanol, then remove the product with 2M NH$_3$/methanol. Dissolve the resulting oil (153 mg, 98% isolated yield) in methanol, add NH$_4$Cl (20.9 mg, 1 eq) as a solid, and sonicate the solution at room temperature for 15 min. Concentrate in vacuo to provide the title compound: mass spectrum (ion spray): m/z=392.3 (M+1); mp 164.2° C.

Example 35

4-Fluoro-N-(3-(methyl-(1-methyl-piperidin-4-yl)-amino)phenyl)benzamide hydrochloride

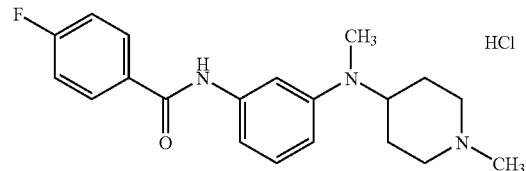

A method similar to Example 34, using 4-fluoro-N-(3-(1-methyl-piperidin-4-ylamino)phenyl)benzamide hydrochloride (Example 27), gives the title compound as a white solid (102 mg): mass spectrum (ion spray): m/z=342.4 (M+1); mp 76.1° C.

Example 36

2-Methyl-N-(3-(methyl-(1-methyl-piperidin-4-yl)-amino)phenyl)benzamide hydrochloride

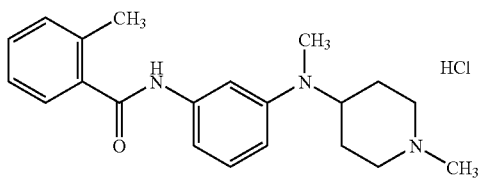

A method similar to Example 34, using 2-methyl-N-(3-(1-methyl-piperidin-4-ylamino)phenyl)benzamide hydrochloride (Example 39), gives the title compound as a white solid (25 mg): mass spectrum (ion spray): m/z=338.4 (M+1); mp 82.4° C.

Example 37

4-Fluoro-N-(3-(methyl-(1-methyl-piperidin-4-yl)-amino)phenyl)-2-trifluoromethyl-benzamide hydrochloride

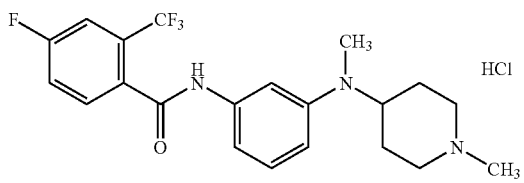

A method similar to Example 34, using 4-fluoro-N-(3-(1-methyl-piperidin-4-ylamino)phenyl)-2-trifluoromethyl-benzamide hydrochloride (Example 33), gives the title compound as a white solid (114 mg): mass spectrum (ion spray): m/z=410.4 (M+1); mp 113. 8° C.

Example 38

N-(3-(Methyl-(1-methyl-piperidin-4-yl)-amino)phenyl)-2-trifluoromethyl-benzamide hydrochloride

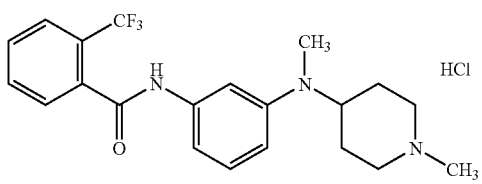

A method similar to Example 34, using N-(3-(1-methyl-piperidin-4-ylamino)phenyl)-2-trifluoromethyl-benzamide hydrochloride (Example 32), gives the title compound as a white solid (125 mg): mass spectrum (ion spray): m/z=392.4 (M+1); mp 84.5° C.

Preparation 58

(2S,4S)-4-(3-(2-Chloro-4-fluoro-benzoylamino)-phenylamino)-2-methyl-piperidine-1-carboxylic acid tert-butyl ester

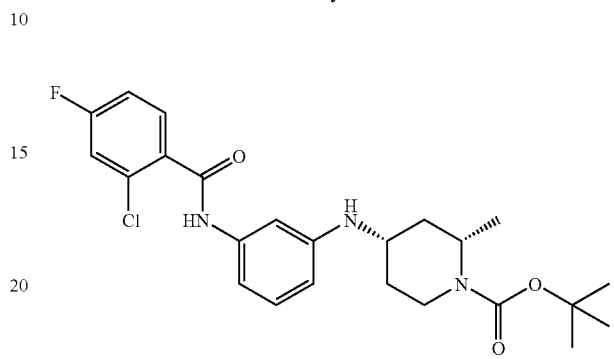

Dissolve N-(3-amino-phenyl)-2-chloro-4-fluoro-benzamide (Preparation 1, 200 mg, 0.756 mmol) and (2S)-2-methyl-4-oxo-piperidine-1-carboxylic acid tert-butyl ester (161 mg, 0.756 mmol) in tetrahydrofuran (5 mL). Add acetic acid (52 μL, 0.907 mmol) and sodium triacetoxyborohydride (192 mg, 0.907 mmol) and stir at room temperature for 18 hr. Heat the reaction to 45° C. for 4 hr. Cool the reaction to room temperature and load onto an SCX column with methanol. Wash the column with methanol, flush with 2M ammonia in methanol, and concentrate in vacuo. Purify by column chromatography (20%-75% ethyl acetate/hexane) to yield 161 mg (46%) of the title compound. Mass spectrum (ion spray): m/z 462.4 (M+1); $^1$H NMR: δ (CDCl$_3$, ppm) 7.76 (m, 2H), 7.20 (m, 1H), 7.15 (m, 1H), 7.10 (m, 1H), 6.70 (d, J=7.6 Hz, 1H), 6.40 (d, J=8.4 Hz, 1H), 4.20 (m, 1H), 3.82 (m, 2H), 3.67 (bs, 1H), 3.20 (m, 1H), 2.00 (m, 2H), 1.65 (m, 2H), 1.47 (s, 9H), 1.27, (m, 4H).

Example 39

2-Chloro-4-fluoro-N-((2S,4S)-3-(2-methyl-piperidin-4-ylamino)-phenyl)-benzamide hydrochloride

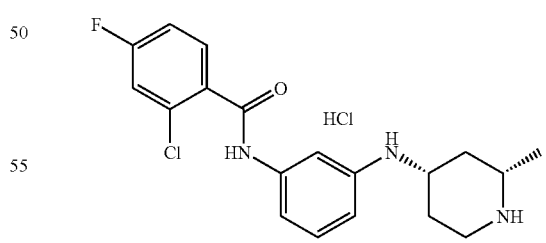

Dissolve (2S,4S)-4-(3-(2-chloro-4-fluoro-benzoylamino)-phenylamino)-2-methyl-piperidine-1-carboxylic acid tert-butyl ester (Preparation 58, 137 mg, 0.296 mmol) in toluene (10 mL). Add p-toluenesulfonyl chloride (152 mg, 0.798 mmol) and heat to 100° C. for 2 hr. Cool to room temperature and load onto an SCX column with methanol. Wash the column with methanol, flush with 2M ammonia in methanol, and concentrate in vacuo. Purify by column chromatography (0%-15% 2 M NH₃ in methanol/CH₂Cl₂) to yield an oil. Make the hydrochloride salt by sonication with one equivalent of ammonium chloride dissolved in methanol to yield 75 mg (64%) of the title compound. Mass spectrum (ion spray): m/z=362.1 (M+1); ¹H NMR δ (D₂O/DCl, ppm) 7.78 (s, 1H), 7.49 (m, 3H), 7.21 (t, J=9 Hz, 18 Hz, 2H), 7.07 (t, J=9.0 Hz, 18.0 Hz, 1H), 3.83 (m, 1H), 3.45 (m, 1H), 3.20 (m, 1H), 2.95 (m, 1H), 2.18 (m, 2H), 1.80 (m, 1H), 1.65 (m, 1H), 1.20 (d, J=6.6 Hz, 3H); mp 202° C. (dec.).

Example 40

2-Chloro-N-((2S,4S)-3-(1,2-dimethyl-piperidin-4-ylamino)-phenyl)-4-fluoro-benzamide hydrochloride

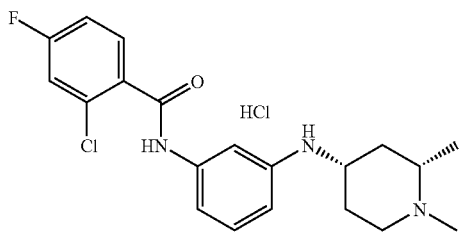

Dissolve 2-chloro-4-fluoro-N-((2S,4S)-3-(2-methyl-piperidin-4-ylamino)-phenyl)-benzamide hydrochloride (Example 39, 50 mg, 0.125 mmol) in methanol (5 mL). Add acetic acid (22 μL, 0.375 mmol) followed by sodium cyanoborohydride (11.8 mg, 0.188 mmol). Cool to 0° C. and add 37% formaldehyde (11.2 μL, 0.138 mmol). Warm to room temperature and stir for 18 hr. Add aqueous saturated sodium bicarbonate and dichloromethane. Separate organic layer and extract aqueous with dichloromethane (2×25 mL). Combine organic extracts, dry (MgSO₄), filter, and concentrate in vacuo. Purify by column chromatography (0%-10% 2M NH₃ in methanol/CH₂Cl₂) to yield an oil. Make the hydrochloride salt by sonication with one equivalent of ammonium chloride dissolved in methanol to yield 28 mg (54%) of the title compound: mass spectrum (ion spray): m/z 376.2 (M+1); ¹H NMR δ (D₂O/DCl, ppm) 7.71 (s, 1H), 7.90 (m, 3H), 7.16 (m, 2H), 7.02 (m, 1H), 3.82 (m, 1H), 3.48 (m, 1H), 3.12 (m, 1H), 2.98 (m, 1H), 2.68 (s, 3H), 2.15 (m, 2H), 1.83 (s, 1H), 1.72 (m, 1H), 1.20 (d, J=6.3 Hz, 3H); mp 91-4° C.

Preparation 59

(2R,4R)-4-(3-(2-Chloro-4-fluoro-benzoylamino)-phenylamino)-2-methyl-piperidine-1-carboxylic acid tert-butyl ester

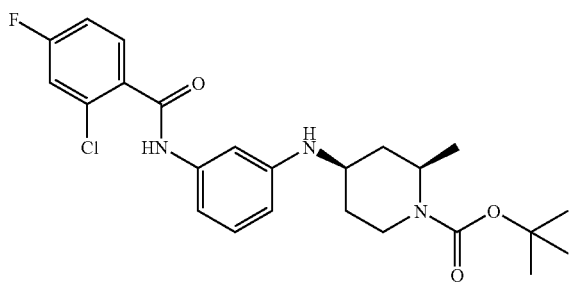

Dissolve N-(3-amino-phenyl)-2-chloro-4-fluoro-benzamide (Preparation 1, 200 mg, 0.756 mmol) and (2R)-2-methyl-4-oxo-piperidine-1-carboxylic acid tert-butyl ester (161 mg, 0.756 mmol) in tetrahydrofuran (5 mL). Add acetic acid (52 μl, 0.907 mmol) and sodium triacetoxyborohydride (192 mg, 0.907 mmol) and stir at room temperature for 18 hr. Heat the reaction to 45° C. for 4 hr. Cool the reaction to room temperature and load onto an SCX column with methanol. Wash the column with methanol, flush with 2M ammonia in methanol, and concentrate in vacuo. Purify by column chromatography (20%-75% ethyl acetate/hexane) to yield 80 mg (23%) of the title compound: mass spectrum (ion spray): m/z=462.4 (M+1); ¹H NMR: δ (CDCl₃, ppm) 7.76 (m, 2H), 7.20 (m, 1H), 7.15 (m, 1H), 7.10 (m, 1H), 6.70 (d, J=7.6 Hz, 1H), 6.40 (d, J=8.4 Hz, 1H), 4.20 (m, 1H), 3.82 (m, 2H), 3.67 (bs, 1H), 3.20 (m, 1H), 2.00 (m, 2H), 1.65 (m, 2H), 1.47 (s, 9H), 1.27, (m, 4H).

Example 41

2-Chloro-4-fluoro-N-((2R,4R)-3-(2-methyl-piperidin-4-ylamino)-phenyl)-benzamide hydrochloride

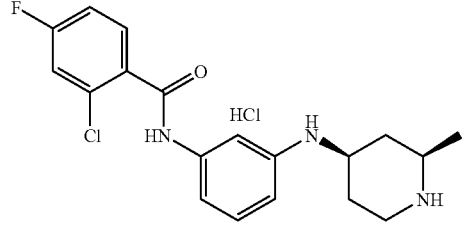

Dissolve (2R,4R)-4-(3-(2-chloro-4-fluoro-benzoylamino)-phenylamino)-2-methyl-piperidine-1-carboxylic acid tert-butyl ester (Preparation 59, 119 mg, 0.258 mmol) in toluene (5 mL). Add p-toluenesulfonyl chloride (152 mg, 0.798 mmol) and heat to 100° C. for 3 hr. Cool to room temperature and load onto an SCX column with methanol. Wash the column with methanol, flush with 2M ammonia in methanol, and concentrate in vacuo. Purify by column chromatography (0%-10% 2M NH₃ in methanol/CH₂Cl₂) to yield an oil. Make the hydrochloride salt by sonication with one equivalent of ammonium chloride dissolved in methanol to yield 40 mg (39%) of the title compound: mass spectrum (ion spray): m/z=362.1 (M+1); ¹H NMR δ (D₂O/DCl, ppm) 7.78 (s, 1H), 7.49 (m, 3H), 7.21 (t, J=9.0 Hz, 18.0 Hz, 2H), 7.07 (t, J=9.0 Hz, 18.0 Hz, 1H), 3.83 (m, 1H), 3.45 (m, 1H), 3.20 (m, 1H), 2.95 (m, 1H), 2.18 (m, 2H), 1.80 (m, 1H), 1.65 (m, 1H), 1.20 (d, J=6.6 Hz, 3H); mp 182-5° C.

Example 42

2-Chloro-N-((2R,4R)-3-(1,2-dimethyl-piperidin-4-ylamino)-phenyl)-4-fluoro-benzamide hydrochloride

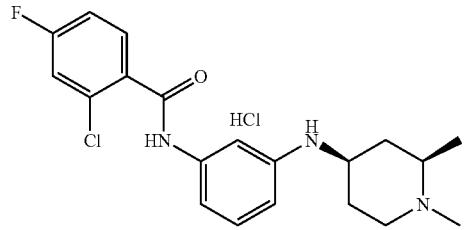

Dissolve 2-chloro-4-fluoro-N-((2R,4R)-3-(2-methyl-piperidin-4-ylamino)-phenyl)-benzamide hydrochloride (Example 41, 30 mg, 0.075 mmol) in methanol (5 mL). Add acetic acid (13 μL, 0.225 mmol) followed by sodium cyanoborohydride (7.1 mg, 0.113 mmol). Cool to 0° C. and add 37% formaldehyde (6.7 μL, 0.083 mmol). Warm to room temperature and stir for 18 hr. Add aqueous saturated sodium bicarbonate and dichloromethane. Separate organic layer and extract aqueous with dichloromethane (2×25 mL). Combine organic extracts, dry (MgSO$_4$), filter, and concentrate in vacuo. Purify by column chromatography (0%-10% 2M NH$_3$ in methanol/CH$_2$Cl$_2$) to yield an oil. Make the hydrochloride salt by sonication with one equivalent of ammonium chloride dissolved in methanol to yield 21 mg (68%) of the title compound. Mass spectrum (ion spray): m/z=376.4 (M+1); mp 159-62° C.

Example 43

2-Chloro-4-fluoro-N-(2-fluoro-3-(1-methyl-piperidi-nylamino)-phenyl)-benzamide

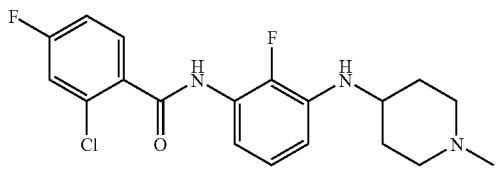

Mix 2-fluoro-N-(1-methyl-piperidin-4-yl)-benzene-1,3-diamine (Preparation 20) (0.08 g) and 2-chloro-4-fluorobenzoyl chloride (83 mg) in 1,4-dioxane (5 mL) and heat at reflux for 2 hr. Partition the reaction mixture between ethyl acetate and saturated aqueous NaCl, dry over anhydrous sodium sulfate, evaporate and purify on a silica gel column (10 g) (dichloromethane-2M NH$_3$ in methanol, gradient) to give 0.106 g of the title compound (78% yield): mass spectrum (ion spray): m/z=380 (M+1); $^1$H NMR (CDCl$_3$): 8.19 (br s, 1H), 7.83 (dd, 1H), 7.66 (dd, 1H), 7.19 (dd, 1H), 7.09 (ddd, 1H), 7.00 (dd, 1H), 6.52 (ddd, 1H), 3.76 (br d, 1H), 3.29 (m, 1H), 2.81 (br d, 2H), 2.29 (s, 3H), 2.13 (m, 2H), 2.05 (m, 2H), 1.52 (m, 2H).

Dissolve the benzamide in methanol, add 0.28 mL of 1 N HCl in ether and evaporate to give its mono-hydrochloric acid salt.

Example 44

2-Chloro-4-fluoro-N-(2-fluoro-3-(methyl-(1-methyl-piperidin-4-yl)-amino)-phenyl)-benzamide

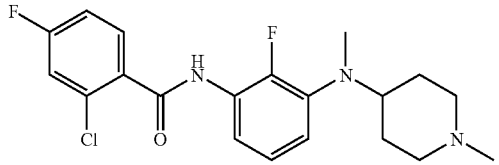

Heat 2-fluoro-N-methyl-N-(1-methyl-piperidin-4-yl)-benzene-1,3-diamine (Preparation 22, 44 mg) with 2-chloro-4-fluorobenzoyl chloride (40 mg) in 1,4-dioxane (5 mL) at reflux for 2 hr. Dilute the reaction mixture with methanol (5 mL) and load on a SCX column (10 g). After wash with methanol, elute the product with 2 M NH$_3$ in methanol, evaporate to give 73 mg of the title compound: mass spectrum (electric spray) m/z=394 (M+1); $^1$H NMR (CDCl$_3$): 8.29 (br d, 1H), 7.94 (t, 1H), 7.81 (dd, 1H), 7.18 (dd, 1H), 7.05 (m, 2H), 6.77 (ddd, 1H), 3.15 (m, 1H), 2.72 (s, 3H), 2.26 (s, 3H), 1.96 (m, 2H), 1.83 (m, 2H), 1.70 (m, 2H).

The benzamide is dissolved in methylene chloride and 0.185 mL of 1N HCl in ether is added and evaporated, dried in vacuum to give its monohydrochloric acid salt.

Example 45

2,4,6-Trifluoro-N-(2-fluoro-3-(methyl-(1-methyl-piperidin-4-yl)-amino)-phenyl)-benzamide

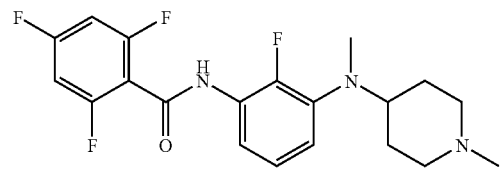

Heat a mixture of 2-fluoro-N-methyl-N-(1-methyl-piperidin-4-yl)-benzene-1,3-diamine (Preparation 22, 60 mg) and 2,4,6-trifluorobenzoyl chloride (59 mg) in 1,4-dioxane (5 mL) for 2 hr. Dilute the reaction mixture with methanol (5 mL) and load on a SCX column (10 g). After wash with methanol, elute the product with 2M NH$_3$ in methanol, evaporate and purify on a silica gel column (4 g, solvent: dichloromethane-2M NH$_3$ in methanol, gradient) to give 94 mg of the title compound: mass spectrum (electric spray) m/z=396 (M+1); $^1$H NMR (CDCl$_3$): 7.96 (m, 1H), 7.84 (br s, 1H), 7.05 (m, 1H), 6.79 (m, 3H), 3.48 (d, 1H), 3.16 (m, 3H), 2.91 (br d, 2H), 2.74 (s, 3H), 2.27 (s, 3H), 1.97 (m, 2H), 1.84 (m, 2H), 1.72 (m, 2H).

Dissolve the benzamide in methanol (2 mL), add 1N HCl in ether (0.24 mL), evaporate to give its mono-hydrochloric acid salt.

Example 46

2,4-Difluoro-N-(2-fluoro-3-(methyl-(1-methyl-piperidin-4-yl)-amino)-phenyl)-benzamide

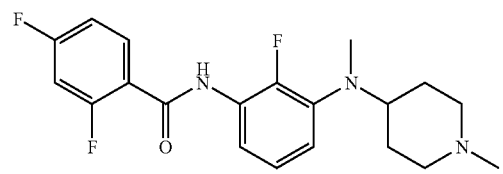

Using a method similar to example 45, using 2,4-difluorobenzoyl chloride gives the title compound: mass spectrum (electric spray) m/z=378 (M+1); $^1$H NMR (CDCl$_3$): 8.67 (br d, 1H), 8.21 (m, 1H), 8.00 (m, 1H), 7.04 (m, 1H), 6.94 (m, 1H), 6.77 (m, 1H), 3.17 (m, 1H), 2.90 (br d, 2H), 2.75 (s, 3H), 2.26 (s, 3H), 1.97 (m, 2H), 1.84 (m, 2H), 1.72 (m, 2H). Using a method similar to the above example, provides the mono hydrochloride salt.

Example 47

2-Chloro-N-(3-(ethyl-(1-methyl-piperidin-4-yl)-amino)-2-fluoro-phenyl)-4-fluoro-benzamide

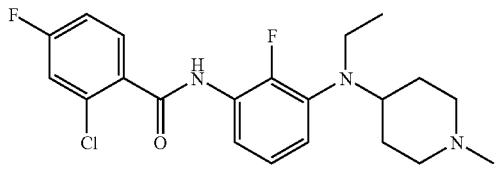

Heat a mixture of N-ethyl-2-fluoro-N-(1-methyl-piperidin-4-yl)-benzene-1,3-diamine (Preparation 27) and 2-chloro-4-fluorobenzoyl chloride (23 mg) in 1,4-dioxane (5 mL) at reflux for 1 hour. Dilute with methanol (5 mL), load on a SCX column (10 g), wash with methanol, elute the product with 2M NH$_3$ in methanol, evaporate to give the title compound: mass spectrum (electric spray) m/z=408 (M+1). Purify further by HPLC to give the di-trifluoroacetic acid salt.

Example 48

2-Chloro-4-fluoro-N-(3-fluoro-5-(methyl-(1-methyl-piperidin-4-yl)-amino)-phenyl)-benzamide

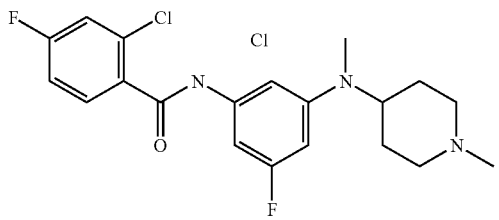

Combine 5-fluoro-N-methyl-N-(1-methyl-piperidin-4-yl)-benzene-1,3-diamine (Preparation 29, 0.036 g, 0.15 mmol), 2-chloro-4-fluoro-benzoyl chloride (0.044 g, 0.23 mmol) and 1,4-dioxane (2 mL), stir and heat at reflux. After 3 hr, cool to ambient temperature. Load on a SCX column (10 g), wash with methanol, elute with 2M ammonia-methanol. Concentrate eluent to obtain 0.059 g (100%) the title compound as a free base. Dissolve this material in dichloromethane (5 mL) and treat with 1M hydrochloric acid in ether (0.15 mL, 0.15 mmol). Concentrate to give the title compound as a brown powder: high resolution mass spectrum: Obs. m/z 394.1495; Calc. m/z 394.1497; $^1$H NMR (CDCl$_3$) of free base: 7.8 (bs, 1H), 7.7 (m, 1H), 7.2 (m, 1H), 7.1 (m, 1H), 6.8 (s, 1H), 6.7 (m, 1H), 6.2 (m, 1H), 3.5 (m, 1H), 2.9 (m, 2H), 2.8 (s, 3H), 2.3 (s, 3H), 2.1 (m, 2H), 1.9 (m, 2H), 1.7 (m, 2H).

Examples 49-52

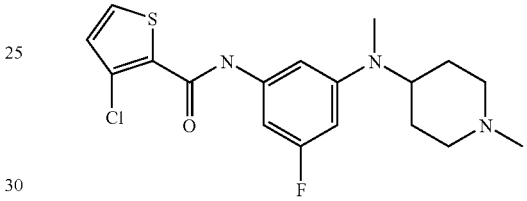

Using methods similar to Example 48, the following compounds are prepared, isolated and converted to mono hydrochloric acid salts

| No | Ar | Structure | Data |
|---|---|---|---|
| 49 | 2-(3-bromo-thiophene) | 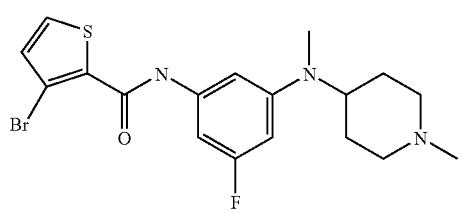 | mass spectrum: obs. m/z 426.14; Calc'd m/z 426.06; mp 175-180° C. $^1$H NMR (CDCl$_3$): 10.5 (bs, 1H), 10.3 (s, 1H), 7.9 (d, 1H), 7.3 (d, 1H), 7.0 (m, 2H), 6.6 (d, 1H), 4.0 (m, 1H), 3.5 (m, 2H), 3.2 (m, 2H), 2.7 (s, 3H), 2.5 (s, 3H), 2.2 (m, 2H), 1.8 (m, 2H). |
| 50 | 2-chloro-phenyl | 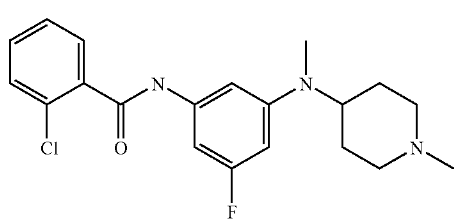 | mass spectrum: obs. m/z 376.1613, calc'd m/z 376.1592; mp 170-175° C.; Analysis calc'd for C$_{20}$H$_{24}$Cl$_{12}$FN$_3$O•0.5H$_2$O: C, 57.01; H, 5.98; N, 9.97. Found: C, 56.96; H, 5.92; N, 9.96 |

-continued

| No | Ar | Structure | Data |
|---|---|---|---|
| 51 | 4-fluoro-phenyl | 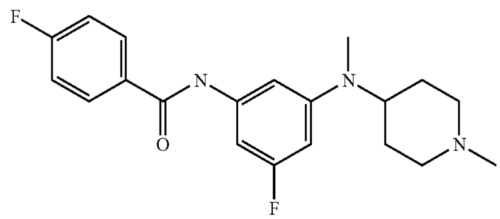 | mass spectrum: obs. m/z 360.1890; calc'd m/z 360.1887; mp 175° C.; Analysis calc'd for $C_{20}H_{23}F_2N_3O \cdot 1.35HCl$: C, 58.78; H, 6.01; N, 10.28. Found: C, 58.73; H, 5.95; N, 10.24. |
| 52 | 2,4-difluoro-phenyl | 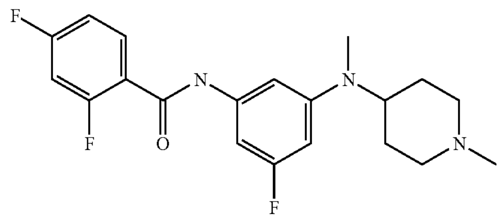 | mass spectrum: obs. m/z 378.25; calc'd m/z 378.17; mp 175° C.; Analysis calc'd for $C_{20}H_{22}F_3N_3O \cdot 2.38\ HCl$: C, 51.75; H. 5.29; N, 9.05. Found: C, 51.81; H, 5.14; N, 8.95. |

Example 53

4-Fluoro-N-(3-fluoro-5-(1-methyl-piperidin-4-ylamino)-phenyl)-benzamide dihydrochloride salt

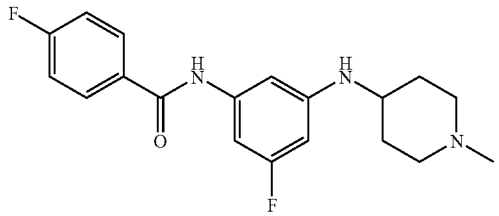

Add slowly 4-fluorobenzoyl chloride (403 mg, 2.54 mmol) to a solution of 5-fluoro-benzene-1,3-diamine (Preparation 32, 320 mg, 2.54 mmol) in triethylamine (514 mg, 0.71 mL, 5.08 mmol) and THF (10 mL) at 0° C. Stir the mixture overnight and gradually raise to room temperature. Quench the reaction with 0.1N NaOH solution, and extract the mixture with ethylacetate three times. Combine the organic layers and wash with saturated NaCl solution, dry over $Na_2SO_4$, filter and concentrate to give a solid.

Purify by chromatography (silica gel, eluting with 25-40% ethylacetate in hexanes) gives 379 mg (60%) of N-(3-amino-5-fluoro-phenyl)-4-fluoro-benzamide.

Combine the above benzamide (379 mg, 1.53 mmol), 1-methyl-4-piperidone (345 mg, 3.06 mmol), THF (1.5 mL), 1,2-dichloroethane (15 mL), molecular sieve 4 A (0.7 g) and acetic acid (276 mg, 0.26 mL, 4.59 mmol). Add sodium triacetoxyborohydride portionwise and stir the mixture at room temperature overnight. Quench the reaction with 0.1N NaOH solution, extract the mixture with $CH_2Cl_2$ three times. Combine the organic layers, dry over $Na_2SO_4$, filter and concentrate to give a crude residue. Purify by chromatography (silica gel, eluting with 5.5% 2M $NH_3$-methanol in $CH_2Cl_2$) provides 434 mg (82%) of the free base of the title compound: Free base: mass spectrum (ion spray): m/z=346.1; $^1H$ NMR ($CDCl_3$, ppm): 7.86 (m, 3H), 7.14 (t, 2H), 6.88 (s, br, 1H), 6.60 (dt, 1H), 6.10 (dt, 1H), 3.79 (d, 1H), 3.24 (m, 1H), 2.78 (m, 2H), 2.31 (s, 3H), 2.17-2.03 (m, 4H), 1.42 (m, 2H). Dissolve the free base in methanol and add 2 equivalents of 1 N HCl in diethylether. Remove the solvent and wash with diethylether. Remove the solvent to obtain the title compound: Di-hydrochloride salt: Anal calculated for $C_{19}H_{21}F_2N_3O \cdot 2HCl$: C, 54.55; H, 5.54; N, 10.04. Found: C, 54.58; H, 5.45; N, 9.84.

Example 54

2,6-Difluoro-N-(3-fluoro-5-(1-methyl-piperidin-4-ylamino)-phenyl)-benzamide dihydrochloride salt

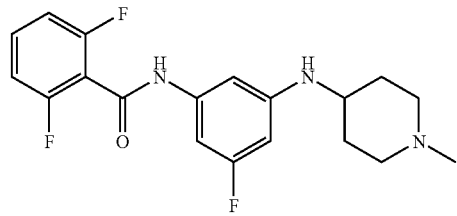

Using methods similar to example 53, using 2,6-difluorobenzoyl chloride (448 mg, 2.54 mmol) gives 515 mg (56% two-step yield) of the free base of the title compound. Using a salt formation method similar to that described in Example 59 gives the title compound: Free base: mass spectrum (ion spray): m/z=364.1 (M+1); $^1H$ NMR ($CDCl_3$, ppm): 7.63 (s, br, 1H), 7.55 (m, 1H), 7.40 (s, 1H), 7.13 (t, 2H), 7.02 (s, br, 1H), 6.67 (dt, 1H), 6.24 (dt, 1H), 3.90 (m, 1H), 3.41 (m, 1H), 2.92 (m, 2H), 2.43 (s, 3H), 2.22 (m, 4H), 1.60 (m, 2H). Di-hydrochloride salt: Anal calc'd for $C_{19}H_{20}F_3N_3O \cdot 2HCl$: C, 52.31; H, 5.08; N, 9.63. Found: C, 52.65; H, 4.96; N, 9.44.

Example 55

2,4,6-Trifluoro-N-(3-fluoro-5-(1-methyl-piperidin-4-ylamino)-phenyl)-benzamide hydrochloride salt

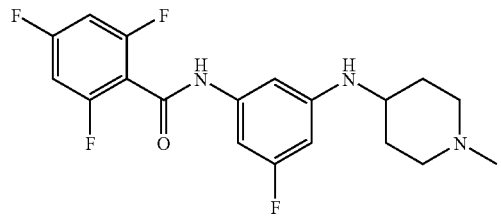

Using methods similar to example 53, using 2,4,6-trifluorobenzoyl chloride (494 mg, 2.54 mmol) gives 525 mg (54% two-step yield) of the free base of the title compound. Using a salt formation method similar to that described in Example 59, using 1 equivalent of HCl gives obtain the title compound:

Free base: mass spectrum (ion spray): m/z=382.1 (M+1); $^1$H NMR (CDCl$_3$, ppm): 7.87 (s, br, 1H), 6.85 (s, br, 1H), 6.70 (m, 2H), 6.54 (m, 1H), 6.11 (dt, 1H), 3.80 (d, 1H), 3.25 (m, 1H), 2.75 (m, 2H), 2.30 (s, 3H), 2.16-2.02 (m, 4H), 1.49 (m, 2H). Mono-hydrochloride salt: Anal calc'd for C$_{19}$H$_{19}$F$_4$N$_3$O.HCl—H$_2$O: C, 52.36; H, 5.09; N, 9.64. Found, C, 52.71; H, 4.78; N, 9.62.

Example 56

2-Chloro-6-fluoro-N-(3-fluoro-5-(1-methyl-piperidin-4-ylamino)-phenyl)-benzamide dihydrochloride salt

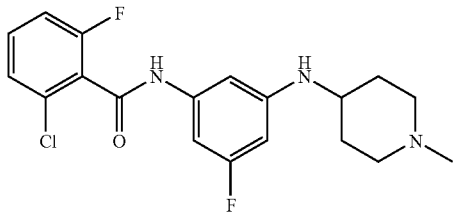

Using methods similar to example 53, using 2-chloro-6-fluorobenzoyl chloride (490 mg, 2.54 mmol) gives 667 mg (69% two-step yield) of the free base of the title compound. Using a salt formation method similar to that described in Example 59 gives the title compound: Free base: mass spectrum (ion spray): m/z=380.0 (M+1); $^1$H NMR (CDCl$_3$, ppm): 7.38 (m, 2H), 7.28 (m, 1H), m 7.12 (m, 1H), 6.91 (s, br, 1H), 6.56 (dt, 1H), 6.14 (dt, 1H), 3.83 (d, 1H), 3.29 (m, 1H), 2.77 (m, 2H), 2.33 (s, 3H), 2.20-2.06 (m, 4H), 1.55 (m, 2H). Di-hydrochloride salt: Anal calc'd for C$_{19}$H$_{20}$ClF$_2$N$_3$O.2HCl.0.4H$_2$O: C, 49.61; H, 5.00; N, 9.14. Found: C, 49.27; H, 4.55; N, 9.08.

Example 57

2-Chloro-4-fluoro-N-(3-fluoro-5-(1-methyl-piperidin-4-ylamino)-phenyl)-benzamide dihydrochloride salt

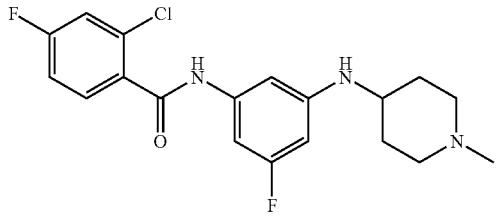

Using methods similar to example 53, using 2-chloro-4-fluorobenzoyl chloride (490 mg, 2.54 mmol) gives 654 mg (68% two-step yield) of the free base of the title compound. Using a salt formation method similar to that described in Example 59 gives the title compound: Free base: mass spectrum (ion spray): m/z=380.0 (M+1); $^1$H NMR (CDCl$_3$, ppm): 7.82 (m, 2H), 7.24 (dd, 1H), 7.17 (m, 1H), 6.90 (s, br, 1H), 6.60 (m, 1H), 6.15 (dt, 1H), 3.83 (d, 1H), 3.31 (m, 1H), 2.85 (m, 2H), 2.35 (s, 3H), 2.23-2.08 (m, 4H), 1.53 (m, 2H). Di-hydrochloride salt: Anal. calc'd. for C$_{19}$H$_{20}$ClF$_2$N$_3$O.2HCl: C, 50.40; H, 4.89; N, 9.28. Found: C, 50.43; H, 4.60; N, 9.29.

Examples 58-65

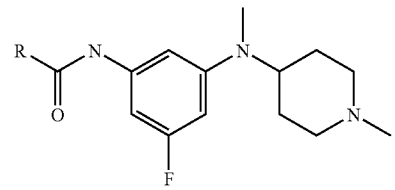

Examples 58-65 are synthesized by heating 5-fluoro-N-methyl-N-(1-methyl-piperidin-4-yl)-benzene-1,3-diamine (Preparation 31, 200 μL of 0.5M solution in dioxane) and the appropriate R-acid chloride (0.10 mmol) to 90° C. for 2 hr. The reaction mixture is diluted with 10% acetic acid/methanol (0.5 mL). The resulting solution is directly applied to a 2 g SCX column. After thoroughly washing with methanol, the column is eluted with 1M ammonia-methanol and the eluant is concentrated and further purified by high-throughput mass guided chromatography. The compounds are characterized by chromatography using a Metachem™ C18 column (monochrom 3 micron, 2.5×25 cm) using a 10-90% solvent B gradient in 4.5 min., where solvent A is 0.% trifluoroacetic acid in water and solvent B is 0.1% trifluoroacetic acid in acetonitrile. The procedure is repeated in parallel for Examples 64-71

| Ex. | Structure | Name | Data |
|---|---|---|---|
| 58 | 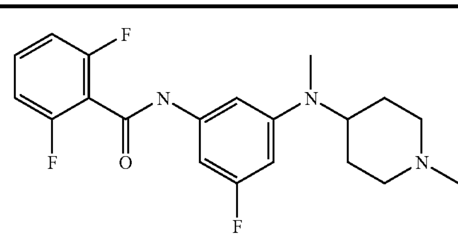 | 2,6-Difluoro-N-(3-fluoro-5-(N'-methyl-N'-(1-methyl-piperidin-4-yl)amino)phenyl)benzamide | LCMS Rf 1.54 min at 254 nm, m/e 378 (M + 1). |

| Ex. | Name | Data |
|---|---|---|
| 59 | 3-Chloro-N-(3-fluoro-5-(N'-methyl-N'-(1-methyl-piperidin-4-yl)amino)phenyl)thiopheneamide | LCMS Rf 1.72 min at 254 nm, m/e 382 (M + 1). |
| 60 | 2,4,6-Trifluoro-N-(3-fluoro-5-(N'-methyl-N'-(1-methyl-piperidin-4-yl)amino)phenyl)benzamide | LCMS Rf 1.61 min at 254 nm, m/e 396 (M + 1). |
| 61 | 3,4-Difluoro-N-(3-fluoro-5-(N'-methyl-N'-(1-methyl-piperidin-4-yl)amino)phenyl)benzamide | LCMS Rf 1.65 min at 254 nm, m/e 378 (M + 1). |
| 62 | 2-Bromo-N-(3-fluoro-5-(N'-methyl-N'-(1-methyl-piperidin-4-yl)amino)phenyl)benzamide | LCMS Rf 1.58 min at 254 nm, m/e 422 (M + 1). |
| 63 | N-(3-fluoro-5-(N'-methyl-N'-(1-methyl-piperidin-4-yl)amino)phenyl)isonicotinamide | LCMS Rf 1.24 min at 254 nm, m/e 343 (M + 1). |
| 64 | 2,4-Dichloro-N-(3-fluoro-5-(N'-methyl-N'-(1-methyl-piperidin-4-yl)amino)phenyl)benzamide | LCMS Rf 1.73 min at 254 nm, m/e 410 (M + 1). |

| Ex. | Structure | Name | Data |
|---|---|---|---|
| 65 | 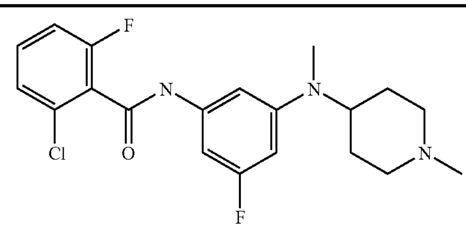 | 2-Chloro-6-fluoro-N-(3-fluoro-5-(N'-methyl-N'-(1-methyl-piperidin-4-yl)amino)phenyl)benzamide | LCMS Rf 1.58 min at 254 nm, m/e 394 (M + 1). |

Example 66

4-Cyano-N-(6-(1-methylpiperidin-4-ylamino)pyridin-2-yl)benzamide hydrochloride

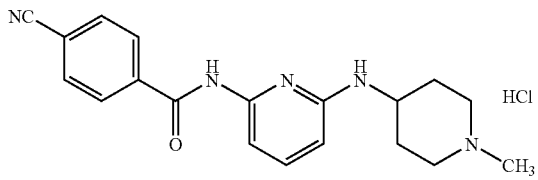

Combine 4-cyanobenzoyl chloride (300 μL, 1.80 mmol), 2,6-diaminopyridine (600 mg, 5.5 mmol, and dioxane (10 mL); stir at room temperature for 2 hr. Pour into water and adjust to pH>12 by the addition of 5N NaOH. Extract with CH₂Cl₂ twice, combine organics, dry over MgSO₄, and concentrate. Chromatograph (silica gel, eluting with 0-10% methanol/CH₂Cl₂). Dissolve the purified intermediate N-(6-amino-pyridin-2-yl)-4-cyano-benzamide (202 mg, 0.84 mmol, 47%) in THF (10 mL). Add to this 1-methyl-4-piperidone (77 mg, 0.68 mmol), acetic acid (150 μL, 2.5 mmol), and sodium triacetoxyborohydride (440 mg, 2.10 mmol). Stir the reaction at room temperature for 18 hr, and quench by the addition of saturated aqueous NaHCO₃. Extract the aqueous layer with ethylacetate twice, wash the combined organics with saturated aqueous NaCl, dry over MgSO₄, and concentrate. Chromatograph the material (silica gel, eluting with 0-20% 2M NH₃ in methanol/CH₂Cl₂). Dissolve the clean material (10.4 mg, 5%) in methanol and add 1 equivalent (1.7 mg) of NH₄Cl. Sonicate the reaction at room temperature for 15 min, then concentrate to provide the title compound: mass spectrum (ion spray): m/z=336.0 (M+1).

Example 67

4-Fluoro-N-(3-(methyl-(1-methyl-piperidin-4-yl)-amino)phenyl)-2-trifluoromethyl-benzamide hydrochloride

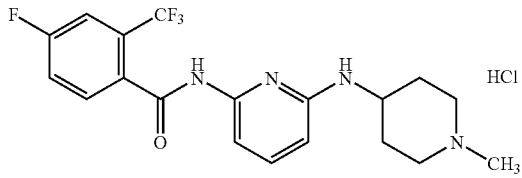

A method similar to Example 66, using 4-fluoro-2-trifluoromethylbenzoyl chloride, gives the title compound as a white solid (42 mg): mass spectrum (ion spray): m/z=397.0 (M+1); mp 84.9° C.

Example 68

N-(3-(methyl-(1-methyl-piperidin-4-yl)-amino)phenyl)-2,3,4-trifluoro-benzamide hydrochloride

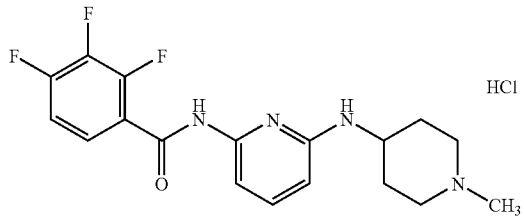

A method similar to Example 66, using 2,3,4-trifluorobenzoyl chloride, gives the title compound as a white solid (32 mg): mass spectrum (ion spray): m/z=365.3 (M+1); mp 231.4° C. (dec.).

Example 69

2-Chloro-4-fluoro-N-(6-(methyl-(1-methyl-piperidin-4-yl)-amino)-pyridin-2-yl)-benzamide hydrochloride

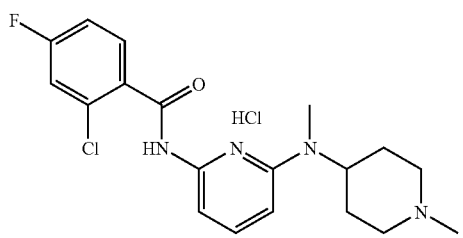

Prepare according to procedure in Example 66 starting with N-methyl-N-(1-methyl-piperidin-4-yl)-pyridine-2,6-diamine (Preparation 34) (200 mg, 0.907 mmol) and 2-chloro-4-fluorobenzoyl chloride (263 mg, 1.36 mmol), and using pyridine as the solvent, to yield 185 mg (49%) of the title compound: mass spectrum (ion spray): m/z=377.2 (M+1);

Analysis calc'd for $C_{19}H_{23}N_4OFCl_2 \cdot 0.6H_2O$: C, 53.80; H, 5.75; N, 13.21. Found: C, 53.55; H, 5.66; N, 13.28; mp 229-31° C.

Example 70

4-Fluoro-N-(6-(methyl-(1-methyl-piperidin-4-yl)-amino)-pyridin-2-yl)-benzamide hydrochloride

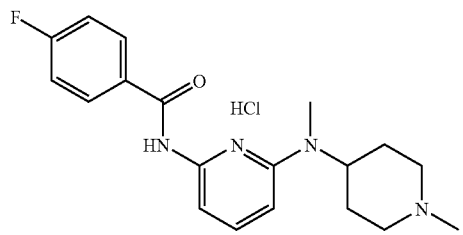

Prepare according to Example 69 starting with N-Methyl-N-(1-methyl-piperidin-4-yl)-pyridine-2,6-diamine (Preparation 34) (200 mg, 0.91 mmol) and 4-fluorobenzoyl chloride (160 ut, 1.36 mmol) to yield 309 mg (90%) of the title compound: mass spectrum (ion spray): m/z=343.3 (M+1); Analysis calc'd for $C_{19}H_{24}N_4OFCl \cdot 0.6H_2O$: C, 58.56; H, 6.52; N, 14.38. Found: C, 58.31; H, 6.37; N, 14.39; mp 250-2° C.

Example 71

N-(6-(Methyl-(1-methylpiperidin-4-yl)amino)pyridin-2-yl)isonicotinamide hydrochloride

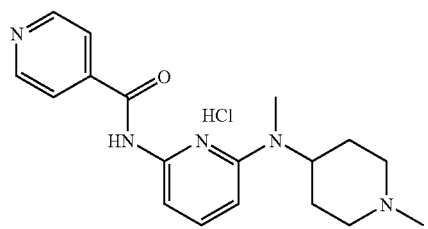

Prepare according to procedure in Example 69 starting with N-methyl-N-(1-methyl-piperidin-4-yl)-pyridine-2,6-diamine (Preparation 34) (175 mg, 0.794 mmol), isonicotinoyl chloride hydrochloride (212 mg, 1.19 mmol), and pyridine (15 mL) to yield 247 mg (86%) of the title compound: mass spectrum (ion spray): m/z=326.1 (M+1); Analysis Calcd for $C_{18}H_{24}N_5OCl \cdot 0.5H_2O$: C, 58.29; H, 6.79; N, 18.88. Found: C, 58.49; H, 6.79; N, 19.22. mp 274-7° C.

Example 72

Furan-2-carboxylic acid (6-(methyl-(1-methyl-piperidin-4-yl)-amino)-pyridin-2-yl)-amide hydrochloride

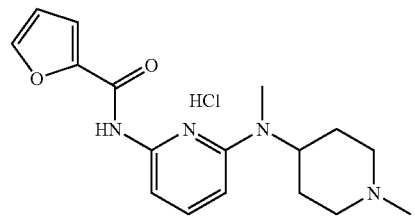

Prepare according to procedure in Example 69 starting with N-methyl-N-(1-methyl-piperidin-4-yl)-pyridine-2,6-diamine (Preparation 34, 175 mg, 0.794 mmol), 2-furoyl chloride (117 µL, 1.19 mmol), and pyridine (15 mL) to yield 243 mg (87%) of the title compound: mass spectrum (ion spray): m/z=315.1 (M+1); Analysis calc'd for $C_{17}H_{23}N_4O_2Cl \cdot 0.2H_2O$: C, 57.60; H, 6.65; N, 15.81. Found: C, 57.31; H, 6.72; N, 15.81. mp 116-9° C.

Example 73

Thiophene-2-carboxylic acid (6-(methyl-(1-methyl-piperidin-4-yl)-amino)-pyridin-2-yl)-thiophenamide hydrochloride

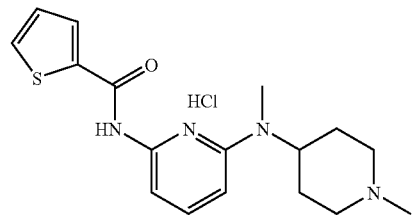

Prepare according to procedure in Example 69 starting with N-methyl-N-(1-methyl-piperidin-4-yl)-pyridine-2,6-diamine (Preparation 34) (175 mg, 0.794 mmol), thiophene-2-carbonyl chloride (127 µL, 1.19 mmol), and pyridine (15 mL) to yield 238 mg (82%) of the title compound: mass spectrum (ion spray): m/z=331.1 (M+1); Analysis Calcd for $C_{17}H_{23}N_4OSCl$: C, 55.65; H, 6.32; N, 15.27. Found: C, 55.46; H, 6.49; N, 15.41. mp 126-8° C.

Example 74

N-(6-(methyl-(1-methyl-piperidin-4-yl)-amino)-pyridin-2-yl)-propionamide hydrochloride

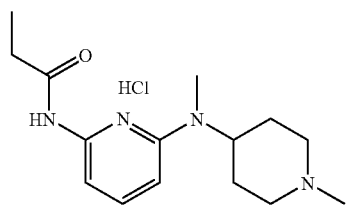

Prepare according to procedure in Example 69 starting with N-methyl-N-(1-methyl-piperidin-4-yl)-pyridine-2,6-diamine (Preparation 34, 175 mg, 0.794 mmol), propionic anhydride (152 uL, 1.19 mmol), and pyridine (15 mL) to yield 134 mg (54%) of the title compound: mass spectrum (ion spray): m/z=277.1 (M+1); Analysis Calcd for $C_{15}H_{25}N_4OCl\cdot0.2H_2O$: C, 57.11; H, 7.80; N, 17.76. Found: C, 56.73; H, 8.16; N, 17.94. mp 216-8° C.

Example 75

Cyclobutanecarboxylic acid (6-(methyl-(1-methyl-piperidin-4-yl)-amino)-pyridin-2-yl)-amide hydrochloride

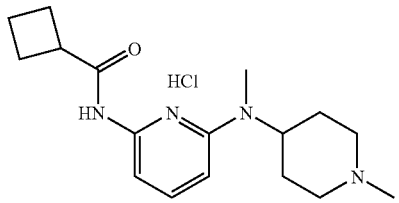

Prepare according to procedure in Example 69 starting with N-Methyl-N-(1-methyl-piperidin-4-yl)-pyridine-2,6-diamine (Preparation 34) (175 mg, 0.794 mmol), cyclobutanecarbonyl chloride (136 μL, 1.19 mmol), and pyridine (15 mL) to yield 237 mg (88%) of the title compound: mass spectrum (ion spray): m/z=303.1 (M+1); Analysis Calcd for $C_{17}H_{27}N_4OCl\cdot0.1H_2O$: C, 59.93; H, 8.05; N, 16.45. Found: C, 59.81; H, 7.93; N, 16.45. mp 258-60° C.

Example 76

Cyclohexanecarboxylic acid(6-(methyl-(1-methyl-piperidin-4-yl)-amino)-pyridin-2-yl)-amide hydrochloride

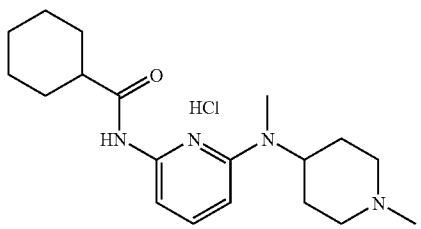

Prepare according to procedure in Example 69 starting with N-methyl-N-(1-methyl-piperidin-4-yl)-pyridine-2,6-diamine (Preparation 34, 175 mg, 0.794 mmol), cyclohexanecarbonyl chloride (159 μL, 1.19 mmol), and pyridine (15 mL) to yield 257 mg (88%) of the title compound. Mass spectrum (ion spray): m/z 331.2 (M+1); Analysis Calcd for $C_{19}H_{31}N_4OCl$: C, 62.19; H, 8.51; N, 15.27. Found: C, 61.22; H, 8.44; N, 15.39. mp 250-2° C.

Example 77

Cyclopropanecarboxylic acid (6-(methyl-(1-methyl-piperidin-4-yl)-amino)-pyridin-2-yl)-amide hydrochloride

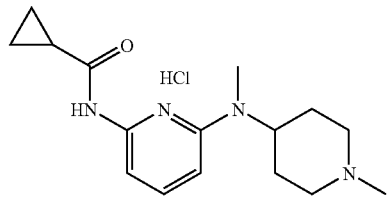

Prepare according to procedure in Example 69 starting with N-methyl-N-(1-methyl-piperidin-4-yl)-pyridine-2,6-diamine (Preparation 34, 175 mg, 0.794 mmol), cyclopropanecarbonyl chloride (108 μL, 1.19 mmol), and pyridine (15 mL) to yield 190 mg (74%) of the title compound: mass spectrum (ion spray): m/z 289.1 (M+1); Analysis Calc'd for $C_{16}H_{25}N_4OCl\cdot0.1H_2O$: C, 58.83; H, 7.78; N, 17.15. Found: C, 58.69; H, 7.71; N, 17.31. mp 258-60° C.

Example 78

2,6-Difluoro-N-(6-(methyl-(1-methyl-piperidin-4-yl)-amino)-pyridin-2-yl)-benzamide hydrochloride

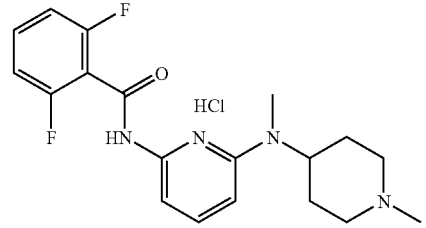

Prepare according to procedure in Example 66 starting with N-methyl-N-(1-methyl-piperidin-4-yl)-pyridine-2,6-diamine (Preparation 34, 200 mg, 0.907 mmol), 2,6-difluorobenzoyl chloride (125 μL, 0.998 mmol), and 1,4-dioxane (10 mL) to yield 289 mg (80%) of the title compound: mass spectrum (ion spray): m/z=361.3 (M+1); Analysis Calcd for $C_{19}H_{23}N_4OF_2Cl\cdot0.5H_2O$: C, 56.22; H, 5.96; N, 13.80. Found: C, 56.49; H, 5.80; N, 14.15. mp 308° C. (dec.).

Example 79

2,4,6-Trifluoro-N-(6-(methyl-(1-methyl-piperidin-4-yl)-amino)-pyridin-2-yl)-benzamide hydrochloride

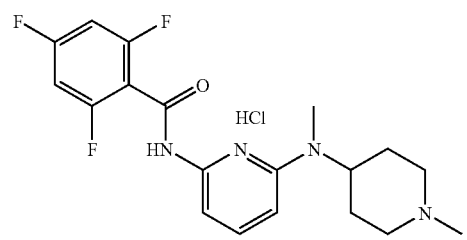

Prepare according to procedure in Example 66 starting with N-methyl-N-(1-methyl-piperidin-4-yl)-pyridine-2,6-diamine (Preparation 34) (200 mg, 0.907 mmol), 2,4,6-trifluorobenzoyl chloride (130, μL, 0.998 mmol), and 1,4-dioxane (10 mL) to yield 302 mg (80%) of the title compound: mass spectrum (ion spray): m/z=379.2 (M+1); Analysis calc'd for $C_{19}H_{22}N_4OF_3Cl.0.5H_2O$: C, 53.84; H, 5.47; N, 13.22. Found: C, 54.02; H, 5.32; N, 13.56. mp 302° C. (dec.).

Example 80

2-Chloro-N-(6-(methyl-(1-methyl-piperidin-4-yl)-amino)-pyridin-2-yl)-benzamide hydrochloride

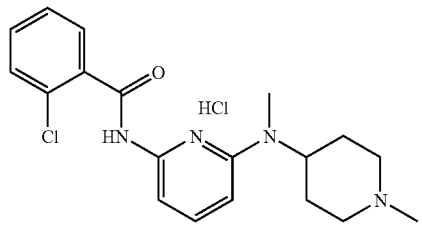

Prepare according to procedure in Example 66 starting with N-methyl-N-(1-methyl-piperidin-4-yl)-pyridine-2,6-diamine (Preparation 34) (200 mg, 0.907 mmol), 2-chlorobenzoyl chloride (126 μL, 0.998 mmol), and 1,4-dioxane (10 mL) to yield 340 mg (95%) of the title compound: mass spectrum (ion spray): m/z=359.3 (M+1); Analysis calc'd for $C_{19}H_{24}N_4OCl_2.0.5H_2O$: C, 56.44; H, 6.23; N, 13.86. Found: C, 56.21; H, 5.91; N, 14.23. mp 90-2° C.

Example 81

2-Chloro-6-fluoro-N-(6-(methyl-(1-methyl-piperidin-4-yl)-amino)-pyridin-2-yl)-benzamide hydrochloride

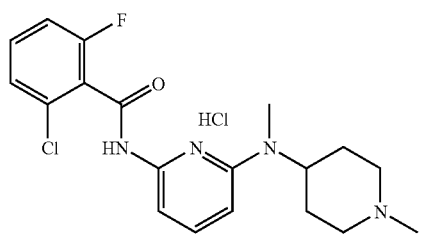

Prepare according to procedure in Example 66 starting with N-methyl-N-(1-methyl-piperidin-4-yl)-pyridine-2,6-diamine (Preparation 34) (200 mg, 0.907 mmol), 2-chloro-6-fluorobenzoyl chloride (179 mg, 0.998 mmol), and 1,4-dioxane (10 mL) to yield 310 mg (83%) of the title compound: mass spectrum (ion spray): m/z=377.2 (M+1); Analysis calc'd for $C_{19}H_{23}N_4OCl_2.0.5H_2O$: C, 54.03; H, 5.73; N, 13.27. Found: C, 53.71; H, 5.71; N, 13.45. mp 283-6° C.

Example 82

4-Fluoro-N-(6-(methyl-(1-methyl-piperidin-4-yl)-amino)-pyridin-2-yl)-2-trifluoromethyl-benzamide hydrochloride

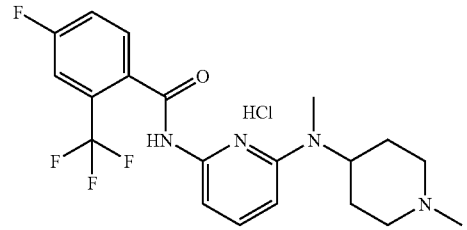

Prepare according to procedure in Example 66 starting with N-methyl-N-(1-methyl-piperidin-4-yl)-pyridine-2,6-diamine (Preparation 34) (200 mg, 0.907 mmol), 4-fluoro-2-(trifluoromethyl)benzoyl chloride (165 μL, 1.09 mmol), and 1,4-dioxane (10 mL) to yield 332 mg (82%) of the title compound: mass spectrum (ion spray): m/z=410.8 (M+1); Analysis calc'd for $C_{20}H_{23}N_4OClF_4$ $1.5H_2O$: C, 50.69; H, 5.53; N, 11.82. Found: C, 50.66; H, 5.17; N, 12.01. mp 100-2° C.

Example 83

N-(6-(Methyl-(1-methyl-piperidin-4-yl)-amino)-pyridin-2-yl)-2-trifluoromethoxy-benzamide hydrochloride

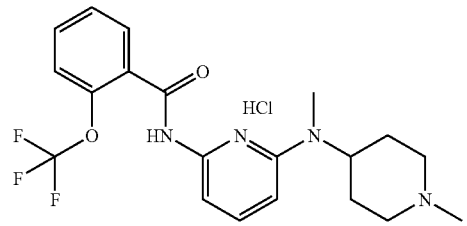

Prepare according to procedure in Example 66 starting with N-methyl-N-(1-methyl-piperidin-4-yl)-pyridine-2,6-diamine (Preparation 34) (200 mg, 0.907 mmol), 2-(trifluoromethoxy)benzoyl chloride (175 uL, 1.09 mmol), and 1,4-dioxane (10 mL) to yield 357 mg (88%) of the title compound: mass spectrum (ion spray): m/z=408.8 (M+1); Analysis calc'd for $C_{20}H_{23}N_4O_2F_3Cl.1.0H_2O$: C, 51.89; H, 5.66; N, 12.10. Found: 51.64; 5.50; 12.48. mp 102-4° C.

Example 84

4-Bromo-N-(6-(methyl-(1-methyl-piperidin-4-yl)-amino)-pyridin-2-yl)-benzamide hydrochloride

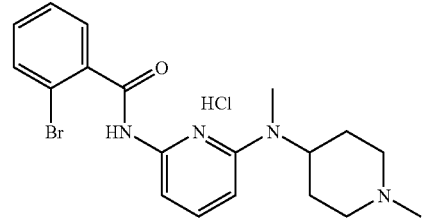

Prepare according to procedure in Example 66 starting with N-methyl N-(1-methyl-piperidin-4-yl)-pyridine-2,6-diamine (Preparation 34) (200 mg, 0.907 mmol), 2-bromobenzoyl chloride (142 L, 1.09 mmol), and 1,4-dioxane (10 mL) to yield 335 mg (84%) of the title compound: mass spectrum (ion spray): m/z=404.3 (M+1); Analysis Calculated for $C_{19}H_{24}N_4OBrCl \cdot 1.1H_2O$: C, 49.65; H, 5.75; N, 12.19. Found: C, 49.39; H, 5.51; N, 12.46; mp 121-3° C.

Example 85

4-Fluoro-N-(6-methyl-piperidin-4-yl-amino)-pyridin-2-yl)-benzamide hydrochloride

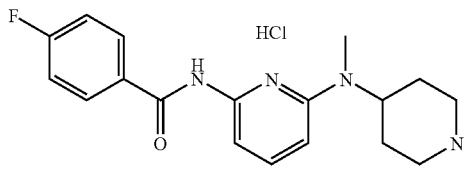

Place 4-(N-(6-(4-fluorobenzoylamino)pyridin-2-yl)-N-methylamino)piperidine-1-carboxylic acid tert-butyl ester (Preparation 41, 0.94 g, 2.2 mmol) in 20 mL of $CH_2Cl_2$ and add trifluoroacetic acid (3.16 mL, 21.9 mmol). Stir for 2 hr then pour directly on a 10 g SCX column and wash with methanol. Remove the product with 2M $NH_3$ in methanol and concentrate in vacuo. Chromatograph (silica gel, eluting with 0-20% 2M $NH_3$ in methanol/$CH_2Cl_2$) to give 0.54 g (75%) of product. Dissolve the clean material in methanol and add 1 equivalent (87.9 mg) of $NH_4Cl$. Sonicate the reaction at room temperature for 15 min, then concentrate to provide the title compound: mass spectrum (ion spray): m/z=329.3 (M+1); mp 152.4° C.

Example 86

2-Chloro-4-fluoro-N-(6-methyl-piperidin-4-yl-amino)-pyridin-2-yl)-benzamide hydrochloride

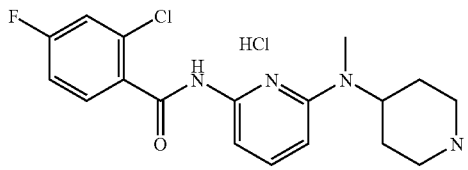

A method similar to Example 85, using 4-((6-(2-chloro-4-fluoro-benzoylamino)-pyridin-2-yl)-methyl-amino)-piperidine-1-carboxylic acid tert-butyl ester, (Preparation 42), gives the title compound as a white solid (720 mg): mass spectrum (ion spray): m/z=363.25 (M+1); mp 152.1° C.

Example 87

N-(6-((1-Ethyl-piperidin-4-yl)-methyl-amino)-pyridin-2-yl)-4-fluoro-benzamide hydrochloride

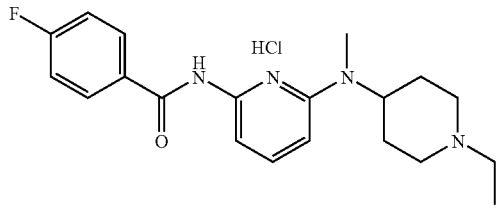

Place 4-fluoro-N-(6-methyl-piperidin-4-yl-amino)-pyridin-2-yl)-benzamide (free-based of Example 85, 0.19 g, 0.57 mmol) in 6 mL of 1,2-dichloroethane and add acetaldehyde (0.11 mL, 2.3 mmol). Stir for 1 hr then add sodium triacetoxyborohydride (0.31 g, 1.4 mmol) and stir for 18 hr. Quench with 1N NaOH and dilute with water and $CH_2Cl_2$. Separate and extract the aqueous layer with $CH_2Cl_2$ (2 times), combine organics, dry over $MgSO_4$, and concentrate. Chromatograph (silica gel, eluting with 0-10% 2M $NH_3$ in methanol/$CH_2Cl_2$) to give 0.119 g (60%) of product. Dissolve the clean material in methanol and add 1 equivalent (17.9 mg) of $NH_4Cl$. Sonicate the reaction at room temperature for 15 min, then concentrate to provide the title compound: mass spectrum (ion spray): m/z=357.3 (M+1); mp 75.6° C.

Example 88

2-Chloro-N-(6-((1-ethyl-piperidin-4-yl)-methyl-amino)-pyridin-2-yl)-4-fluoro-benzamide hydrochloride

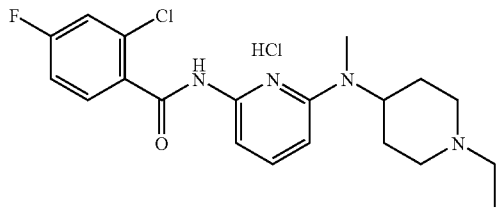

A method similar to Example 87, using 2-chloro-4-fluoro-N-(6-methyl-piperidin-4-yl-amino)-pyridin-2-yl)-benzamide (free-based of Example 86), gives the title compound as a yellow-white solid (102 mg): mass spectrum (ion spray): m/z=391.3 (M+1); mp 132.9° C.

Example 89

4-Fluoro-N-(6-(methyl-(1-propyl-piperidin-4-yl)-amino)-pyridin-2-yl)-benzamide hydrochloride

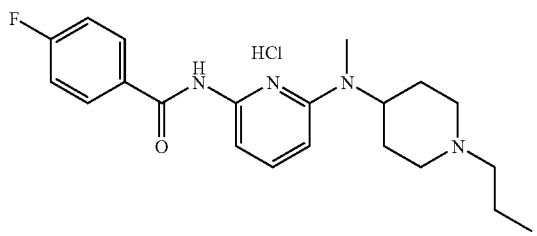

A method similar to Example 87, using 4-fluoro-N-(6-methyl-piperidin-4-yl-amino)-pyridin-2-yl)-benzamide (free-based of Example 85), and propionaldehyde in place of acetaldehyde, gives the title compound as a white solid (77 mg): mass spectrum (ion spray): m/z=371.4 (M+1); mp 84.7° C.

Example 90

2-Chloro-4-fluoro-N-(6-(methyl-(1-propyl-piperidin-4-yl)-amino)-pyridin-2-yl)-benzamide hydrochloride

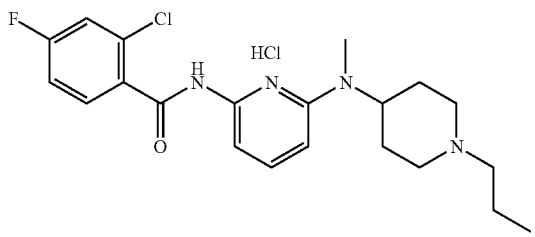

A method similar to Example 87, using 2-chloro-4-fluoro-N-(6-methyl-piperidin-4-yl-amino)-pyridin-2-yl)-benzamide (free-based of Example 86), and propionaldehyde in place of acetaldehyde, gives the title compound as a white solid (41 mg): mass spectrum (ion spray): m/z=405.32 (M+1); mp 258° C. (dec).

Example 91

N-(6-((1-Cyclopropylmethyl-piperidin-4-yl)-methyl-amino)-pyridin-2-yl)-4-fluoro-benzamide hydrochloride

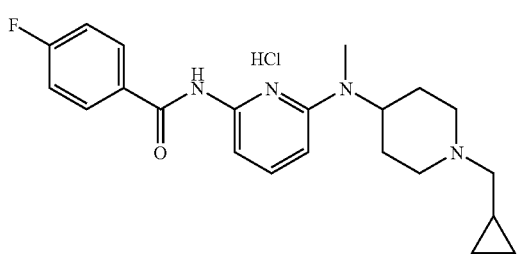

A method similar to Example 87, using 4-fluoro-N-(6-methyl-piperidin-4-yl-amino)-pyridin-2-yl)-benzamide (free-based of Example 85), and cyclopropane carboxaldehyde in place of acetaldehyde, gives the title compound as a white solid (130 mg): mass spectrum (ion spray) m/z=383.2 (M+1); mp 81.6° C.

Example 92

2-Chloro-N-(6-((1-cyclopropylmethyl-piperidin-4-yl)-methyl-amino)-pyridin-2-yl)-4-fluoro-benzamide hydrochloride

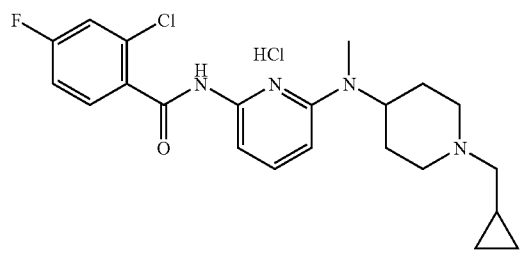

A method similar to Example 87, using 2-chloro-4-fluoro-N-(6-methyl-piperidin-4-yl-amino)-pyridin-2-yl)-benzamide, the free-based product from Example 86, and cyclopropane carboxaldehyde, in place of acetaldehyde, gives the title compound as a white solid (143 mg): mass spectrum (ion spray): m/z=417.3 (M+1); mp 257.5° C.

Example 93

4-Fluoro-N-(6-((1-(2-(1-isopropyl-1H-pyrazol-4-yl)-ethyl)-piperidin-4-yl)-methyl-amino)-pyridin-2-yl)-benzamide hydrochloride

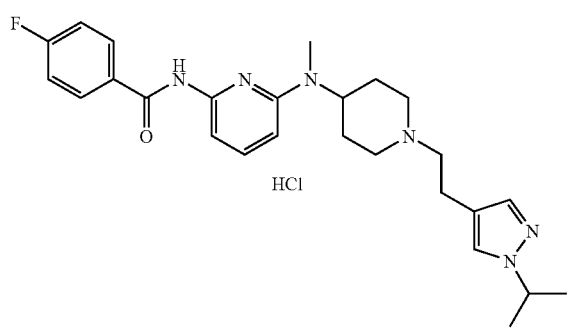

Combine 2-(1-isopropyl-1H-pyrazol-4-yl)-ethanol (Preparation 12, 2 g, 12.9 mmol) and triethylamine (3.6 mL, 25.9 mmol) in 30 mL of THF. Add methanesulfonyl chloride (1.3 mL, 15.6 mmol) and stir for 36 hr. Dilute with water and ethyl acetate. Separate and extract the aqueous layer with CH$_2$Cl$_2$ (2 times). Combine organics, dry over MgSO$_4$, and concentrate in vacuo. Take a portion of this crude mixture (0.17 g, 0.73 mmol) and combine with 4-fluoro-N-(6-methyl-piperidin-4-yl-amino)-pyridin-2-yl)-benzamide (free-based of Example 85, 0.20 g, 0.60 mmol) in 4 ml of DMF. Add potassium carbonate (0.25 g, 1.8 mmol) and heat at 80° C. for 18 hr. Cool and dilute with water and CH$_2$Cl$_2$. Separate and extract the aqueous layer with CH$_2$Cl$_2$ (2 times). Combine organics, dry over MgSO4, and concentrate in vacuo. Chromatograph (silica gel, eluting with 0-10% 2M NH$_3$-methanol/CH$_2$Cl$_2$) to give 0.158 g of product (57%). Dissolve the purified oil in methanol, add NH$_4$Cl (18.2 mg, 1 eq) as a solid, and sonicate the solution at room temperature for 15 min. Concentration provides the title compound: mass spectrum (ion spray): m/z=465.4 (M+1); mp 85.8° C.

Example 94

2-Chloro-4-fluoro-N-(6-((1-(2-(1-isopropyl-1H-pyrazol-4-yl)-ethyl)-piperidin-4-yl)-methyl-amino)-pyridin-2-yl)-benzamide hydrochloride

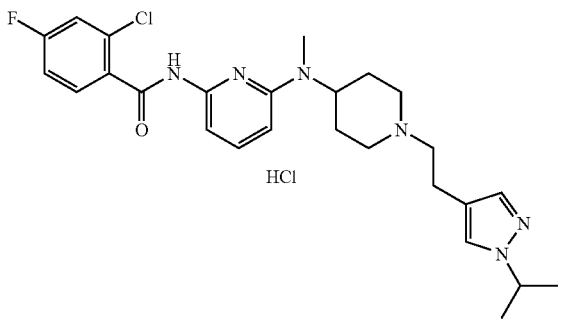

Using a method similar to Example 93, using 2-chloro-4-fluoro-N-(6-methylpiperidin-4-ylamino)pyridin-2-yl)benzamide (Example 86, 150 mg, 0.4 mmol), gives the title compound as a white solid (114 mg): mass spectrum (ion spray): m/z=499.36 (M+1), mp 96.7° C.

Example 95

2,4,6-Trifluoro-N-(6-(1-methyl-piperidin-4-ylamino)-pyridin-2-yl)-benzamide dihydrochloride

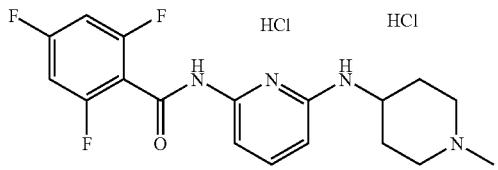

Combine N-(6-amino-pyridin-2-yl)-2,4,6-trifluoro-benzamide (Preparation 43, 668 mg, 2.5 mmol), 1-methyl-4-piperidone (566 mg, 5.0 mmol), acetic acid (450 mg, 0.43 mL, 7.5 mmol), molecular sieves 4 A (1 g) and 1,2-dichloroethane, stir for 30 min at room temperature, then add sodium triacetoxyborohydride (1.325 g, 6.25 mmol) portion wise. Add another batch of 1-methyl-piperidone (566 mg, 5.0 mmol) and sodium triacetoxyborohydride (1.325 g, 6.25 mmol) if starting benzamide is still present after overnight reaction. Quench the reaction with 0.1N NaOH solution. Extract the mixture with ethylacetate three times. Combine organic layers, dry over Na$_2$SO4, filter and concentrate to afford a residue. Chromatography (silica gel, 4% 2M NH$_3$-methanol in CH$_2$Cl$_2$) provides 571 mg (63%) of the free base of the title compound. Dilute the free base in CH$_2$Cl$_2$ (1 mL), add 1M HCl/Et$_2$O (5.6 mL, 5.6 mmol), remove the supernatant, wash the white solid with ether four times and dry in vacuum oven to afford 600 mg (88%) of the free base of the title compound. Using a salt formation method similar to that described in Example 53 gives the title compound: Free base: mass spectrum (ion spray): m/z 365.0 (M+1); $^1$H NMR (CDCl$_3$, ppm): 8.50 (1H, s), 7.49 (m, 2H), 6.70 (m, 2H), 6.14 (d, 1H), 4.38 (d, 1H), 3.48 (m, 1H), 2.78 (m, 2H), 2.28 (s, 3H), 2.05 (m, 4H), 1.51 (m, 2H). Di-hydrochloride salt: Anal calc'd for C$_{18}$H$_{19}$F$_3$N$_4$O-2HCL: C, 49.44; H, 4.84; N, 12.81. Found: C, 49.31; H, 4.96; N, 12.49.

Example 96

4-Fluoro-N-(6-(1-methyl-piperidin-4-ylamino)-pyridin-2-yl)-benzamide dihydrochloride salt

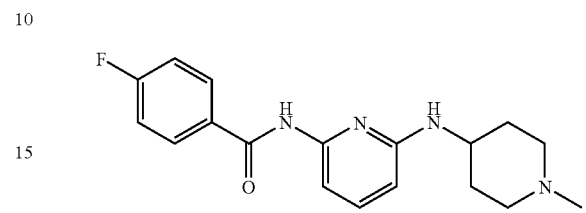

Dissolve 2,6-diaminopyridine (1.637 g, 15 mmol) in dioxane (15 mL) and cool to 0° C. for 10 min. Add 4-fluorobenzoyl chloride (793 mg, 0.59 mL, 5.0 mmol) slowly. After 40 min, remove ice bath and stir the reaction at room temperature. Use the work-up and purification procedures described in Preparation 43 to provide N-(6-Amino-pyridin-2-yl)-4-fluoro-benzamide as a slightly yellow solid (1.170 g, 100%): mass spectrum (ion spray): m/z=232.0 (M+1).

Using a method similar to Preparation 43, using the above benzamide (580 mg, 2.51 mmol, 493 mg) gives 493 mg (60%) of the title compound as a white solid. Using a salt formation method similar to that described in Example 53 gives the title compound: Free base: mass spectrum (ion spray): m/z=329.2 (M+1); $^1$H NMR (CDCl$_3$, ppm): 8.16 (s, 1H), 7.93 (m, 2H), 7.53 (m, 2H), 7.22 (m, 2H), 6.20 (d, 1H), 4.30 (d, 1H), 3.62 (m, 1H), 2.80 (m, 2H), 2.33 (s, 3H), 2.16 (m, 4H), 1.53 (m, 2H). Di-hydrochloride salt: Anal calc'd for C$_{18}$H$_{21}$FN$_4$O.2HCl—H$_2$O: C, 51.56; H, 6.01; N, 13.36. Found: C, 51.78; H, 5.65; N, 13.36.

Example 97

N-(6-(1-Methyl-piperidin-4-ylamino)-pyridin-2-yl)-acetamide dihydrochloride salt

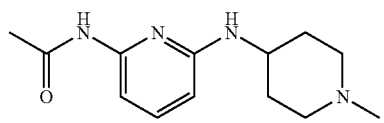

Using a method similar to Example 95 and THF as the reaction solvent (40 mL), using N-(6-amino-pyridin-2-yl)-acetamide (Preparation 44, 1.512 g, 10 mmol) gives 597 mg (24%) of the free base of the title compound. Using a salt formation method similar to that described in Example 53 gives the title compound: Free base: mass spectrum (ion spray): m/z=249.1 (M+1); $^1$H NMR (CDCl$_3$, ppm): 7.60 (s, br, 1H), 7.44 (m, 2H), 6.14 (m, 1H), 4.25 (d, 1H), 3.58 (m, 1H), 2.84 (m, 2H), 2.34 (s, 3H), 2.19 (s, 3H), 2.13 (m, 4H), 1.56 (m 2H). Di-hydrochloride salt: Anal calc'd for C$_{13}$H2ON$_4$O-2HCl-0.25H$_2$O: C, 47.93; H, 6.96; N, 17.20. Found: C, 47.94; H, 7.18; N, 16.77.

Example 98

2-Chloro-N-(6-(1-methyl-piperidin-4-ylamino)-pyridin-2-yl)-benzamidedihydrochloride salt

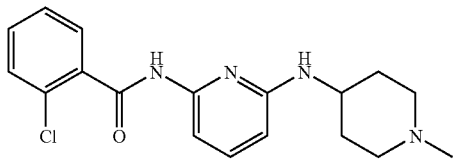

Using a method similar to Example 95 with 1,2-dichloroethane/THF as solvent (1:1, 20 mL), using N-(6-amino-pyridin-2-yl)-2-chloro-benzamide (Preparation 45, 500 mg, 2.02 mmol) gives 285 mg (34%) of the free base of the title compound as a white solid. Using a salt formation method similar to that described in Example 53 gives the title compound: Free base: mass spectrum (ion spray): m/z=345.1 (M+1); $^1$H NMR (CDCl$_3$, ppm): 8.21 (s, 1H), 7.70 (m, 1H), 7.62 (m, 1H), 7.40 (m, 4H), 6.19 (d, 1H), 4.32 (d, 1H), 3.57 (m, 1H), 2.79 (m, 2H), 2.31 (s, 3H), 2.10 (m, 4H), 1.51 (m, 2H). Di-hydrochloride salt: Anal calc'd for C$_{18}$H$_{21}$ClN$_4$O.2HCl: C, 51.75; H, 5.55; N, 13.41. Found: C, 51.47; H, 5.38; N, 13.18.

Example 99

2-Bromo-N-(6-(1-methyl-piperidin-4-ylamino)-pyridin-2-yl)-benzamidedihydrochloride salt

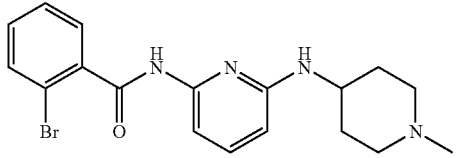

Using a method similar to Example 98, using N-(6-amino-pyridin-2-yl)-2-bromo-benzamide (Preparation 46, 495 mg, 1.69 mmol) gives 195 mg (25%) of the free base of the title compound as a white solid. Using a salt formation method similar to that described in Example 53 gives the title compound: Free base: mass spectrum (ion spray): m/z=389.1 (M+1); $^1$H NMR (CDCl$_3$, ppm): 8.09 (s, 1H), 7.64 (m, 3H), 7.40 (m, 3H), 6.19 (d, 1H), 4.31 (d, 1H), 3.58 (m, 1H), 2.80 (m, 2H), 2.30 (s, 3H), 2.07 (m, 4H), 1.54 (m, 2H). Di-hydrochloride salt: Anal calc'd for C$_{18}$H$_{21}$BrN$_4$O.2HCl.0.5H$_2$O: C, 45.88; H, 5.13; N, 11.89. Found: C, 45.95; H, 5.10; N, 11.73.

Example 100

Cyclohexanecarboxylic acid (6-(1-methyl-piperidin-4-ylamino)-pyridin-2-yl)-amide dihydrochloride salt

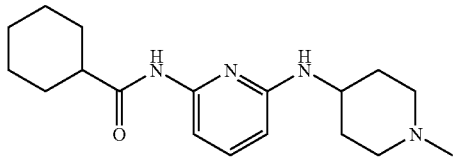

Using a method similar to Example 98, using cyclohexanecarboxylic acid (6-amino-pyridin-2-yl)-amide (Preparation 47, 510 mg, 2.33 mmol) gives 352 mg (39%) of the free base of the title compound. Using a salt formation method similar to that described in Example 53 gives the title compound: Free base: mass spectrum (ion spray): m/z=317.2 (M+1); $^1$H NMR (CDCl$_3$, ppm): 7.52 (s, br, 1H), 7.46 (m, 2H), 6.13 (dd, 1H), 4.24 (d, 1H), 3.58 (m, 1H), 2.82 (m, 2H), 2.33 (s, 3H), 2.24-1.94 (m, 7H), 1.83 (m, 2H), 1.74 (m, 1H), 1.58 (m, 4H), 1.27 (m, 3H). Di-hydrochloride salt: Anal cald for C$_{18}$H$_{28}$N$_4$O-2HCl-0.5H$_2$O: C, 54.27; H, 7.84; N, 14.06. Found: C, 54.36; H, 7.83; N, 13.91.

Example 101

2-Chloro-6-fluoro-N (6-(1-methylpiperidin-4-ylamino)pyridin-2-yl)benzamide, free base and dihydrochloride salt

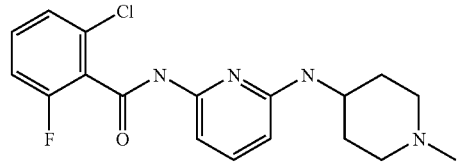

Under an inert atmosphere, stir a mixture of N-(6-aminopyridin-2-yl)-2-chloro-6-fluorobenzamide (Preparation 48, 810 mg, 3.0 mmol), 1-methyl-4-piperidone (339 mg, 0.37 mL, 3.0 mmol), anhydrous THF (50 mL), glacial acetic acid (0.52 mL, 9.2 mmol) at room temperature for 45 min. Add sodium triacetoxyborohydride (1 g, 4.6 mmol). Allow the reaction to go for 4 days. Transfer the reaction mixture into ethyl acetate (200 mL), then wash once with aqueous NaOH (2N, 30 mL). Separate the organic layer, dry over anhydrous sodium sulfate. Remove the solvent under reduced pressure. Clean the residue by chromatography (silica gel; 4%-6% (2M NH$_3$ in methanol)/CH$_2$Cl$_2$). Collect the free base product and convert to its dihydrochloride salt by treating it in CH$_2$Cl$_2$ with excess solution of 1.0M HCl in diethyl ether and adding more ether to cause its precipitation as a white solid (268 mg, 20% yield): mass spectrum (ion spray): m/z=363.2 (M+1); Anal. calculated. for C$_{18}$H2OClFN$_4$O.2HCl.H$_2$O: C, 47.64; H, 5.33; N, 12.35. Found: C, 47.69; H, 5.59; N, 11.85; $^1$H NMR δ (methanol-d$_4$) 8.01 (dd, 1H), 7.60 (q, 1H), 7.44 (d, 1H), 7.31 (t, 1H), 6.91 (d, 1H), 6.65 (d, 1H), 3.98 (m, 1H), 3.64 (d, 2H), 3.30 (dd, 2H), 2.91 (s, 3H), 2.37 (d, 2H), 1.93 (m, 2H)

Example 102

3-Chloro-2,6-difluoro-N-(6-(1-methylpiperidin-4-ylamino)pyridin-2-yl)benzamide and dihydrochloride salt

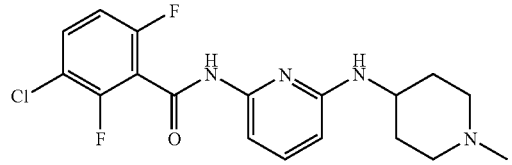

Using a method similar to Example 101, using N-(6-Aminopyridin-2-yl)-3-chloro-2,6-difluorobenzamide (Preparation 49, 764 mg, 2.7 mmol), 1-methyl-4-piperidone (305 mg, 0.3 mL, 2.7 mmol), anhydrous THF (50 mL), glacial acetic acid (0.46 mL, 8.1 mmol), sodium triacetoxyborohydride (848 mg, 4.0 mmol) gives the title compound (dihydrochloride salt: 335 mg, 27% yield): mass spectrum (ion spray): m/z=381.0 (M+1); Anal. calc'd. for $C_{18}H_{19}ClF_2N_4O.2HCl.H_2O$: C, 45.83; H, 4.91; N, 11.88. Found: C, 46.33; H, 5.02; N, 11.36; (LY 635146) $^1$H NMR δ (methanol-$d_4$) 7.99 (dd, 1H), 7.77 (m, 1H), 7.23 (t, 1H), 6.91 (d, 1H), 6.69 (d, 1H), 3.98 (m, 1H), 3.64 (d, 2H), 3.30 (dd, 2H), 2.91 (s, 3H), 2.37 (d, 2H), 1.93 (m, 2H).

Example 103

2,6-Difluoro-3-methyl-N-(6-(1-methylpiperidin-4-ylamino)pyridin-2-yl)benzamide and dihydrochloride salt

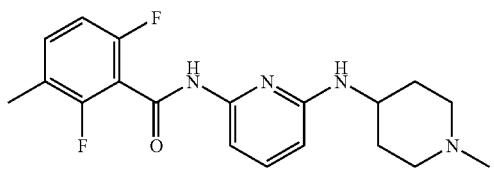

Using a method similar to Example 101, using N-(6-Aminopyridin-2-yl)-2,6-difluoro-3-methylbenzamide (Preparation 50, 662 mg, 2.5 mmol), 1-methyl-4-piperidone (282 mg, 0.26 mL, 2.5 mmol), anhydrous THF (50 mL), glacial acetic acid (0.42 mL, 7.5 mmol), sodium triacetoxyborohydride (795 mg, 3.75 mmol) gives the title compound (dihydrochloride salt: (208 mg, 19% yield): mass spectrum (ion spray): m/z=361.1 (M+1); Anal. calc'd. for $C_{19}H_{22}F_2N_4O$ 2HCL: C, 52.66; H, 5.58; N, 12.93. Found: C, 52.70; H, 5.46; N, 12.75; $^1$H NMR δ (methanol-$d_4$) 8.02 (dd, 1H), 7.51 (q, 1H), 7.09 (t, 1H), 6.90 (d, 1H), 6.63 (d, 1H), 3.98 (m, 1H), 3.64 (d, 2H), 3.30 (dd, 2H), 2.91 (s, 3H), 2.37 (d, 2H), 2.31 (s, 3H), 1.93 (m, 2H)

Example 104

2-Chloro-4-fluoro-N-(6-(1-methylpiperidin-4-ylamino)pyridin-2-yl)benzamide and dihydrochloride salt

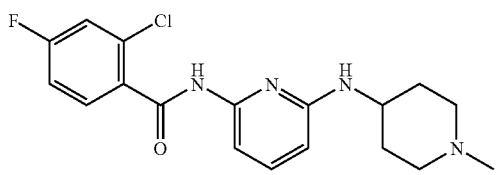

Under an inert atmosphere, stir a mixture of N-(6-aminopyridin-2-yl)-2-chloro-4-fluorobenzamide (Preparation 38, 433 mg, 1.63 mmol), 1-methyl-4-piperidone (369.5 mg, 0.4 mL, 3.27 mmol), 1,2-dichloroethane (20 mL), powdered molecular sieves 4 A (1 g) for 15 min. Add glacial acetic acid (294 mg, 0.28 mL, 4.89 mmol). After 1 hr. add sodium triacetoxyborohydride (869 mg, 4.1 mmol). Allow the reaction to go overnight. transfer the reaction mixture into ethyl acetate (200 mL), then wash once with aqueous NaOH (2N, 30 mL). Separate the organic layer, dry over anhydrous sodium sulfate, pull off the solvent under reduced pressure. Clean the residue by chromatography (silica gel; 5%-6% (2M $NH_3$ in methanol)/$CH_2Cl_2$). Collect the free base product (226 mg, 38% yield). Convert the product to its dihydrochloride salt by treating it in $CH_2Cl_2$ with excess solution of 1.0M HCl in diethyl ether and adding more ether to cause its precipitation as a white solid: mass spectrum (ion spray): m/z=363.0 (M+1); Anal. calculated for $C_{18}H_{20}ClFN_4O.2HCl.0.5H_2O$: C, 48.61; H, 5.21; N, 12.60. Found: C, 48.43; H, 5.11; N, 12.28; (LY 635148) $^1$H NMR δ (methanol-$d_4$) 8.00 (dd, 1H), 7.77 (m, 1H), 7.45 (d, 1H), 7.29 (m, 1H), 6.90 (d, 1H), 6.65 (d, 1H), 3.98 (m, 1H), 3.64 (d, 2H), 3.30 (dd, 2H), 2.91 (s, 3H), 2.37 (d, 2H), 1.93 (m, 2H)

Example 105

2,4-Difluoro-N-(6-(1-methylpiperidin-4-ylamino)pyridin-2-yl)benzamide and dihydrochloride salt

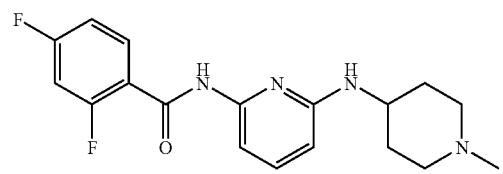

Using a method similar to Example 101, using N-(6-aminopyridin-2-yl)-2,4-difluorobenzamide (Preparation 51, 617 mg, 2.48 mmol), 1-methyl-4-piperidone (280 mg, 0.3 mL, 2.48 mmol), anhydrous THF (50 mL), glacial acetic acid (0.42 mL, 7.4 mmol), sodium triacetoxyborohydride (784 mg, 3.7 mmol) gives the title compound (dihydrochloride salt: 56.4 mg, 5% yield): mass spectrum (ion spray): m/z=347.3 (M+1); Anal. calc'd. for $C_{18}H2OF_2N_4O.2HCl.0.5H_2O$: C, 50.48; H, 5.41; N, 13.08. Found: C, 50.63; H, 5.43; N, 12.84; (LY 635150) $^1$H NMR δ (methanol-$d_4$) 7.95 (m, 2H), 7.20 (m, 2H), 6.86 (d, 1H), 6.73 (d, 1H), 3.98 (m, 1H), 3.64 (d, 2H), 3.30 (dd, 2H), 2.91 (s, 3H), 2.37 (d, 2H), 1.93 (m, 2H)

Example 106

2,6-Dichloro-N-(6-(1-methylpiperidin-4-ylamino)pyridin-2-yl)benzamide and its dihydrochloride salt

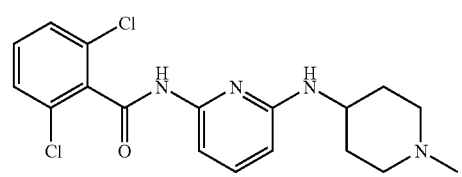

Using a method similar to Example 104 using N-(6-aminopyridin-2-yl)-2,6-dichlorobenzamide (Preparation 52, 569 mg, 2.0 mmol), 1-methyl-4-piperidone 450 mg, 0.5 mL, 4.0 mmol), 1,2-dichloroethane (15 mL), powdered molecular sieves 4 A (1 g), glacial acetic acid (360 mg, 0.34 mL, 6.0 mmol), sodium triacetoxyborohydride (1.06 g, 5.0 mmol) gives the title compound (491 mg, 66% yield): dihydrochloride salt: mass spectrum (ion spray): m/z=379.2 (M+1); Anal. calc'd. for $C_{18}H2OCl_2N_4O\cdot2HCl$: C, 47.81; H, 4.90; N, 12.39. Found: C, 47.59; H, 5.21; N, 12.00; (LY 641053) $^1$H NMR δ (CDCl$_3$) 7.79 (s, 1H), 7.59 (d, 1H), 7.47 (t, 1H), 7.34 (m, 3H), 6.18 (d, 1H), 4.26 (d, 1H), 3.55 (m, 1H), 2.73 (d, 2H), 2.28 (s, 3H), 2.11 (m, 4H), 1.50 (m, 2H)

Example 107

2,6-Difluoro-N-(6-(1-methylpiperidin-4-ylamino) pyridin-2-yl)benzamide Free base and dihydrochloride salt

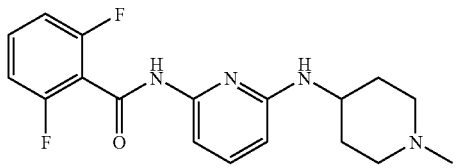

Using a method similar to Example 104 using N-(6-aminopyridin-2-yl)-2,6-difluorobenzamide (Preparation 53, 536 mg, 2.2 mmol), 1-methyl-4-piperidone (486 mg, 0.53 mL, 4.3 mmol), 1,2-dichloroethane (15 mL), powdered molecular sieves 4 Å (1 g), glacial acetic, acid (396 mg, 0.38 mL, 6.6 mmol), sodium triacetoxyborohydride (1.16 g, 5.5 mmol) gives the title compound (596 mg, 78% yield): dihydrochloride salt: mass spectrum (ion spray): m/z=347.2 (M+1); Anal. calc'd. for $C_{18}H2OF_2N_4O\cdot2HCl\cdot0.5H_2O$: C, 50.48; H, 5.41; N, 13.08. Found: C, 50.76; H, 5.77; N, 12.70; $^1$H NMR δ (CDCl$_3$) 7.94 (s, 1H), 7.55 (d, 1H), 7.41 (m, 2H), 6.97 (t, 2H), 6.18 (d, 1H), 4.26 (d, 1H), 3.55 (m, 1H), 2.73 (d, 2H), 2.28 (s, 3H), 2.11 (m, 4H), 1.50 (m, 2H)

Example 108

2,4-Dichloro-N-(6-(1-methyl-piperidin-4-ylamino)-pyridin-2-yl)-benzamide Free base and dihydrochloride salt

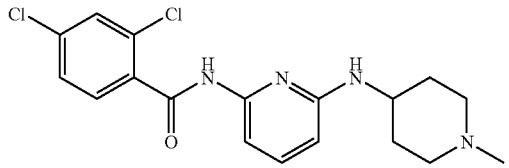

Using a method similar to Example 104 using N-(6-aminopyridin-2-yl)-2,4-dichlorobenzamide (Preparation 54, 621 mg, 2.24 mmol), 1-methyl-4-piperidone (510 mg, 0.55 mL, 4.48 mmol), 1,2-dichloroethane (15 mL), powdered molecular sieves 4 Å (1 g), glacial acetic acid (403.5 mg, 0.38 mL, 6.72 mmol), sodium triacetoxyborohydride (1.2 g, 5.6 mmol) gives the title compound (397 mg, 46% yield): dihydrochloride salt: mass spectrum (ion spray): m/z=379.0 (M+1); Anal. calc'd. for $C_{18}H2OCl_2N_4O\cdot2HCl\cdot0.4H_2O$: C, 47.06; H, 5.00; N, 12.20. Found: C, 47.49; H, 5.31; N, 11.72; $^1$H NMR δ (methanol-d$_4$) 8.01 (dd, 1H), 7.69 (m, 2H), 7.53 (d, 1H), 6.90 (d, 1H), 6.67 (m, 1H), 3.98 (m, 1H), 3.64 (d, 2H), 3.30 (dd, 2H), 2.91 (s, 3H), 2.37 (d, 2H), 1.93 (m, 2H).

Example 109

2,4,6-Trichloro-N(6-(1-methylpiperidin-4-ylamino) pyridin-2-yl)benzamide Free base and HCL salt

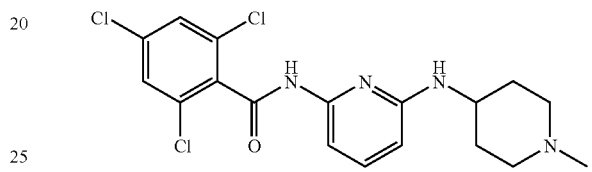

Using a method similar to Example 104 using N-(6-aminopyridin-2-yl)-2,4,6-trichloro-benzamide (Preparation 55, 375 mg, 1.18 mmol), 1-methyl-4-piperidone (270 mg, 0.29 mL, 2.37 mmol), 1,2-dichloroethane (15 mL), powdered molecular sieves 4 Å (1 g), glacial acetic acid (0.21 g, 0.20 mL, 3.54 mmol), sodium triacetoxyborohydride (625 mg, 2.95 mmol) gives the title compound (187 mg, 45% yield): dihydrochloride salt: mass spectrum (ion spray): m/z=412.0 (M+1), $^1$H NMR δ (CDCl$_3$) 7.78 (s, 1H), 7.56 (d, 1H), 7.45 (t, 1H), 7.36 (s, 2H), 6.18 (d, 1H), 4.26 (d, 1H), 3.55 (m, 1H), 2.73 (d, 2H), 2.28 (s, 3H), 2.11 (m, 4H), 1.50 (m, 2H).

Examples 110-115

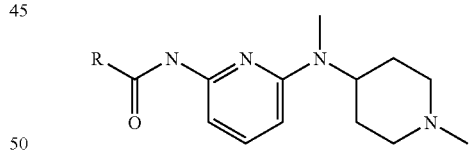

For Examples 110-115, heat N-methyl-N-(1-methylpiperidin-4-yl)-pyridine-2,6-diamine (Preparation 34, 200 μL of 0.5M solution in dioxane) and the appropriate R-acid chloride (0.10 mmol) to 90° C. for 2 hr. The reaction mixture is diluted with 10% acetic acid/methanol (0.5 mL). The resulting solution is directly applied to a 2 g SCX column. After thoroughly washing with methanol, the column is eluted with 1M ammonia-methanol and the eluant is concentrated and further purified by high-throughput mass guided chromatography. The compounds are characterized by chromatography using a Metachem™ C18 column (monochrom 3 micron, 2.5×25 cm) using a 10-90% solvent B gradient in 4.5 min., where solvent A is 0.1% trifluoroacetic acid in water and solvent B is 0.1% trifluoroacetic acid in acetonitrile. The procedure is repeated in parallel for Examples 110-115.

| Ex. | Structure | Name | Data |
|---|---|---|---|
| 110 | (structure) | 3-Chloro-N-(6-(N'-methyl-N'-(1-methylpiperidin-4-yl)amino)pyridin-2-yl)thiopheneamide | LCMS Rf 1.47 Min. at 254 nm, m/e 365 (M + 1). |
| 111 | (structure) | 2,4-Difluoro-N-(6-(N'-methyl-N'-(1-methylpiperidin-4-yl)amino)pyridin-2-yl)benzamide | LCMS Rf 1.36 min. at 254 nm, m/e 361 (M + 1). |
| 112 | (structure) | 3,4-Difluoro-N-(6-(N'-methyl-N'-(1-methylpiperidin-4-yl)amino)pyridin-2-yl)benzamide | LCMS Rf 1.46 min. at 254 nm, m/e 361 (M + 1). |
| 113 | (structure) | 2,3,4-Trifluoro-N-(3-fluoro-5-(N'-methyl-N'-(1-methylpiperidin-4-yl)amino)phenyl)benzamide | LCMS Rf 1.46 min. at 254 nm, m/e 379 (M + 1). |
| 114 | (structure) | N-(6-(N'-methyl-N'-(1-methylpiperidin-4-yl)amino)pyridin-2-yl)nicotinamide | LCMS Rf 1.05 min. at 254 nm, m/e 326 (M + 1). |
| 115 | (structure) | 2,4-Dichloro-N-(3-fluoro-5-(N'-methyl-N'-(1-methyl-piperidin-4-yl)amino)phenyl)benzamide | LCMS Rf 1.54 min. at 254 nm, m/e 393 (M + 1). |

The compounds of this invention are useful for increasing activation of the 5-HT$_{1F}$ receptor. An increase in the activation of the 5-HT$_{1F}$ is useful for treating a variety of disorders which have been linked to decreased neurotransmission of serotonin in mammals, e.g., migraine headaches. See U.S. Pat. No. 5,708,008 demonstrating the nexus between activation of the 5-HT$_{1F}$ receptor and migraine. 5-HT$_{1F}$ receptor binding affinity is determined to demonstrate the use of the compounds of the present invention in the treatment of migraine. The ability of the compounds of this invention to bind to the 5-HT$_{1F}$ receptor subtype is measured essentially as described in N. Adham, et al., *Proceedings of the National Academy of Sciences* (USA), 90: 408-412, 1993.

Membrane Preparation:

Prepare membranes from transfected Ltk-cells (transfected with the human 5-HT$_{1F}$ receptor sequence) that have grown to 100% confluency. Wash the cells twice with phosphate-buffered saline, scrape them from the culture dishes into 5 mL of ice-cold phosphate-buffered saline, and centrifuge at 200×g for 5 min. at 4° C. Resuspend the pellet in 2.5 mL of ice-cold Tris buffer (20 mM Tris HCl, pH 7.4 at 23° C., 5 mM EDTA) and homogenize with a Wheaton tissue grinder. Centrifuge the lysate at 200×g for 5 min. at 4° C. to pellet large fragments which are discarded. Collect the supernatant and centrifuge at 40,000×g for 20 min. at 4° C. Wash the resulting pellet once in ice-cold Tris wash buffer and resuspend in a final buffer containing 50 mM Tris HCl and 0.5 mM EDTA, pH 7.4 at 23° C. Maintain the membrane preparations on ice and utilize them for the radioligand binding assays within two hr. of preparation. Determine protein concentrations by the method of Bradford. *Anal. Biochem.*, 72: 248-254, 1976.

Radioligand Binding:

[$^3$H] 5-HT binding is performed using slight modifications of the 5-HT$_{1D}$ assay conditions reported by Herrick-Davis and Titeler (*J. Neurochem.*, 50: 1624-1631, 1988) with the omission of masking ligands. Conduct radioligand binding studies at 37° C. in a total volume of 250 μL of buffer (50 mM Tris, 10 mM MgCl$_2$, 0.2 mM EDTA, 10 μM pargyline, 0.1% ascorbate, pH 7.4 at 37° C.) in 96 well microtiter plates.

Perform saturation studies using [$^3$H] 5-HT at 12 different concentrations ranging from 0.5 nM to 100 nM. Perform displacement studies using 4.5-5.5 nM [$^3$H] 5-HT. Use 6-12 concentrations of compound to obtain binding profiles of drugs in competition experiments. Incubations are for 30 minutes for both saturation and displacement studies based upon initial investigations which determined equilibrium binding conditions. Define nonspecific binding in the presence of 10 μM 5-HT. Initiate binding by the addition of 50 μL membrane homogenate (10-20 μg). Terminate the reaction by rapid filtration through presoaked (0.5% polyethyleneimine) filters using 48R Brandel Cell Harvester (Gaithersburg, Md.). Wash the filters for 5 seconds with ice cold buffer (50 mM Tris HCl, pH=7.4 at 4° C.), dry the filters, and place them individually into vials containing 2.5 mL Readi-Safe (Beckman, Fullerton, Calif.) and radioactivity was measured using a Beckman LS 5000TA liquid scintillation counter. The efficiency of counting of [$^3$H] 5-HT averages between 45-50%. Analyze the binding data by computer-assisted nonlinear regression analysis (Accufit and Accucomp, Lunden Software, Chagrin Falls, Ohio). Convert the $IC_{50}$ values to $K_i$ values using the Cheng-Prusoff equation. *Biochem. Pharmacol.*, 22: 3099-3108 (1973). Perform experiments in triplicate. Representative compounds of the present invention were assayed essentially as described above and were found to have high affinity for the 5-HT$_{1F}$ receptor, as for example $K_i$'s of less than or equal to about 600 nM. Preferred compounds of the present invention have $K_i$'s of less than or equal to about 300 nM. Yet more preferred compounds are those having a $K_i$ of less than or equal to about 200 nM. Particularly preferred compounds are those having a $K_i$ of less than or equal to about 50 nM. Exemplified compounds have $K_i$'s of less than or equal to about 200 nM.

Measurement of cAMP Formation

As was reported by R. L. Weinshank, et al., WO93/14201, the 5-HT$_{1F}$ receptor is functionally coupled to a G-protein as measured by the ability of serotonin and serotonergic drugs to inhibit forskolin stimulated cAMP production in NIH3T3 cells transfected with the 5-HT$_{1F}$ receptor. Adenylate cyclase activity is determined using standard techniques. A maximal effect is achieved by serotonin. An $E_{max}$, is determined by dividing the inhibition of a test compound by the maximal effect and determining a percent inhibition. N. Adham, et al., supra; R. L. Weinshank, et al., *Proceedings of the National Academy of Sciences* (*USA*), 89: 3630-3634, 1992; and the references cited therein.

Incubate human 5-HT$_{1F}$, receptor transfected NIH3T3 cells (estimated $B_{max}$ from one point competition studies=488 fmol/mg of protein) in DMEM, 5 mM theophylline, 10 mM HEPES (4-(2-hydroxyethyl)-1-piperazineethanesulfonic acid) and 10 uM pargyline for 20 minutes at 37° C., 5% $CO_2$. Use a range of 6 final concentrations of test compound in parallel incubations to obtain drug dose-effect curves. Obtain a dose-response curve for 5-HT measured in parallel, using a fixed dose of methiothepin (0.32 μM), for use in demonstrating competitive antagonism. Add the test compound or 5-HT to the cells, and follow immediately with the addition of forskolin (10 uM) to initiate stimulated cAMP production. Incubate the cells for 10 minutes at 37° C., 5% $CO_2$. Aspirate the medium and quench the reaction with 100 mM HCl. Cool the plates at 4° C. for 15 min., centrifuge to pellet cellular debris (5 min., 500×g), aliquot the supernatant into vials and store at −20° C. until assessment of cAMP formation by radioimmunoassay (cAMP radioimmunoassay kit; Advanced Magnetics, Cambridge, Mass.). Quantify radioactivity using a Packard COBRA Auto Gamma counter, equipped with data reduction software. Representative compounds of the present invention were assayed essentially as described above and found to be agonists of the 5-HT$_{1F}$ receptor.

Protein Extravasation Assay

The inhibition of neuronal protein extravasation is a functional assay for the neuronal mechanism of migraine. A compound's ability to inhibit neuronal protein extravasation can be tested as described in the following assay.

Anesthetize Harlan Sprague-Dawley rats (225-325 g) or guinea pigs from Charles River Laboratories (225-325 g) with sodium pentobarbital (intraperitoneal injection, 65 mg/kg or 45 mg/kg, respectively). For each animal, place the animal in a stereotaxic frame (David Kopf Instruments) with the incisor bar set at −3.5 mm for rats or −4.0 mm for guinea pigs. Make a midline sagittal scalp incision, and drill two pairs of bilateral holes through the skull (6 mm posterially, 2.0 and 4.0 mm laterally on both sides of the mid-line in rats; 4 mm posteriorly and 3.2 and 5.2 mm laterally on both sides of the mid-line in guinea pigs, all coordinates referenced to bregma.). Lower pairs of stainless steel stimulating electrodes, insulated except at the ends (Rhodes Medical Systems, Inc.), through the holes in both hemispheres, one electrode to a hole, to a depth of 9 mm (rats) or 10.5 mm (guinea pigs) from dura.

Expose the femoral vein and inject a dose of the test compound or saline negative control intravenously (1 mL/kg). Approximately 7 min. later, inject a 50 mg/kg dose of Evans Blue intravenously. The Evans Blue is a fluorescent dye which complexes with proteins in the blood and functions as a marker for protein extravasation. Exactly 10 min. postinjection of the test compound, stimulate the left trigeminal ganglion for 3 min. at a current intensity of 1.0 mA (5 Hz, 4 msec duration) with a Model 273 potentiostat/galvanostat (EG&G Princeton Applied Research).

Fifteen minutes following stimulation, kill the animal by exsanguination with 20 mL of saline. Remove the top of the skull to facilitate the collection of dural membrane samples. Remove the membrane samples from both hemispheres, rinse with water, spread flat on microscope slides, dry the tissue on a microscope slide warmer, and apply a coverslip with a 70% glycerol/water solution.

Quantify the amount of Evans Blue dye in each sample using a fluorescence microscope (Zeiss) equipped with a grating monochronomator, a spectrophotometer, a computer-driven motorized stage, and an interface to a personal computer. For each dural membrane sample, measure fluorescence at 25 points (500, μm steps covering a 2.5×2.5 mm square area) using an excitation wavelength of approximately 535 nm and measuring the emission intensity at a wavelength of 600 nm. Determined the mean and standard deviation of these measurements.

The extravasation induced by the electrical stimulation of the trigeminal ganglion is an ipsilateral effect (i.e. occurs only on the side of the dura in which the trigeminal ganglion was stimulated). This allows the stimulated dura to be used as the test tissue and the unstimulated half of the dura to be used as a control. The ratio of the amount of extravasation in the dura from the stimulated side compared to the unstimulated side is calculated. Saline controls yield a ratio of approximately 2.0 in rats and 1.8 in guinea pigs. In contrast, a compound which effectively prevents the extravasation in the dura from the stimulated side will have a ratio of approximately 1.0. Using a range of compound doses and multiple animals at each dosage level, generate a dose-response curve for the test compound and approximate the dose that inhibits the extravasation by 50% ($ID_{50}$). Representative compounds of the present invention were assayed essentially as described above. The compounds were found to significantly inhibit neuronal protein extravasation and are thus efficatious in the neurogenic plasma protein extravasation model for migraine.

Rabbit Saphenous Vein Contraction

Sacrifice male New Zealand White rabbits (3-6 lbs) (Hazleton, Kalamazoo, Mich.) by a lethal dose of sodium pentobarbital (325 mg) injected into the ear vein. Dissect saphenous vein tissue free of connective tissue, cannulate in situ with polyethylene tubing (PE50, outside diameter=0.97 mm) and place in petri dishes containing modified Kreb's solution (118.2 mMol NaCl, 4.6 mMol KCl, 1.6 mMol $CaCl_2.H_2O$, 1.2 mMol $KH_2PO_4$, 1.2 mMol $MgSO_4$, 10.0 mMol dextrose and 24.8 mMol $NaHCO_3$). Bend the tips of two 30-gauge stainless steel hypodermic needles into an L-shape and slip them into the lumen of the polyethylene tubing. Gently push vein tissue from the cannula onto the needles. Separate the needles and attach the lower needle with thread to a stationary glass rod and the upper needle with thread to a force transducer (Statham UC-3).

Mount the tissues in organ baths containing 10 mL of modified Krebs' solution. Maintain tissue bath solutions at 37° C. and aerate with 95% $O_2$ and 5% $CO_2$. Apply an initial optimum resting force of 4 grams to the vein tissue. Record isometric contractions as changes in grams of force on a Beckman Dynograph with Statham UC-3 transducers and microscale accessory attachments. Allow tissues to equilibrate 1 to 2 hr. before exposure to test compound. Add 67 mM KCl to the bath and record the maximal contraction. Flush the bath, allow the tissue to re-equilibrate under a 4 gram force, add test compound and record the force of contraction. Add additional compound to achieve the next concentration in a range of compound concentrations to generate cumulative agonist concentration-response curves for each test compound. Tissues can be used to generate up to two agonist concentration-response curves. Calculate the mean $EC_{50}$ and the maximal compound response, which maximum is expressed as a percentage of the maximal contraction for the tissue in response to the 67 mM KCl administered initially to each tissue.

Two important parameters can be measured with this vasoconstriction assay, saphenous vein contraction ($EC_{50}$) and maximal contraction as a percentage of the maximal KCl response (%$_{max}$ KCl). The saphenous vein contraction ($EC_{50}$) is a measure of the dose required to contract tissue to 50% of the maximal response that the specific compound is capable of mediating. The maximal response that the saphenous vein is capable of exhibiting is measured after administration of a high concentration (67 mM) of KCl. The %$_{max}$ KCl contraction is the ratio of the maximal response that the specific compound is capable of mediating divided by the maximal response that the tissue can produce upon stimulation with KCl. For purposes of this application, a compound may be considered to not have significant vasoconstrictive activity if it produces a maximal contraction of less than or equal to 5% of the contraction produced by the 67 mM KCl positive control at a compound concentration of up to 100 μM, when assayed essentially as described above.

Representative compounds of the present invention were tested for vasoconstrictive activity in the rabbit saphenous vein assay essentially as described above and were found to not be significantly vasoconstrictive. All compounds of the present invention that were tested had a % max KCl less than or equal to 10%. This contrasts greatly with prior art compounds for the treatment of migraine targeting the neural vasoconstrictive model for migraine treatment, which compounds were selected on the basis of strong vasoconstrictive activity, as for example, sumatriptan, which has an $EC_50$ of 0.66 mM and a %$_{max}$ KCl of 64.20 when tested essentially as described above.

Selectivity for the 5-$HT_{1F}$ Receptor

Compounds of the prevent invention are relatively selective for the 5-$HT_{1F}$ receptor, particularly in comparison to other 5-HT receptor subtypes, specifically other receptors in the 5-$HT_1$ subclass, as for example, but without limitation, the 5-$HT_{1A}$, 5-$HT_{1B}$, 5-$HT_{1D}$, and 5-$HT_{1E}$ receptor subtypes. Affinity for these other receptor subtypes can readily be determined by slight modification of the above described radioligand receptor binding assays using cells transfected with the desired receptor subtype in place of cells transfected with the 5-$HT_{1F}$ receptor subtype. The binding affinities of representative compounds of the present invention were determined by such assays and were found to be selective for the 5-$HT_{1F}$ receptor; that is the affinity of the compounds for the 5-$HT_{1F}$ receptor was on the whole, higher than for other receptor subtypes, particular for the 5-$HT_{1B}$ and 5-$HT_{1D}$ receptor subtypes.

Specificity Index

The specificity of compounds of the present invention for 5-$HT_{1F}$ mediated inhibition of neuronal protein extravasation versus vasoconstrictive activity can be expressed with a Specificity Index, which is the ratio of vasoconstriction to efficacy in inhibiting neuronal protein extravasation:

$$\text{Specificity Index} = \frac{\text{Corrected Vasoconstriction } EC_{50}(M)}{\text{Extravasation } ID_{50}(\text{mMol/kg})}$$

The Corrected Vasoconstriction takes into consideration the maximal contraction relative to KCl for each individual compound, and is defined as the vasoconstriction $EC_{50}$ value divided by the %$_{max}$ KCl.

For example, sumatriptan has a corrected vasoconstriction $EC_{50}$ of $1.03 \times 10^{-8}$ M (0.66 mM $EC_{50} \div 64.20\%_{max}$ KCl) and an extravasation inhibition $ID_{50}$ of $2.6 \times 10-8$ mMol/Kg, giving a Specificity Index of 0.40.

Thus the procedure for determining the Specificity Index of any given compound is as follows:

1. Measure the affinity of the compound for the 5-$HT_{1F}$ receptor using the radioligand binding method described above;

2. Once affinity for the 5-$HT_{1F}$ receptor is established, determine whether the compound is an agonist, partial agonist or antagonist of the 5-$HT_{1F}$ receptor by its response in the above described cAMP assay;

3. If the compound is shown to be an agonist or partial agonist with an $E_{max}$ of at least about 50%, measure efficacy of the compound in inhibition of protein extravasation and saphenous vein contraction using the above described assays; and 4. Calculate the Specificity Index as shown above.

While compounds with a Specificity Index greater than 1 are useful for the methods and uses of the present invention, larger values for the Specificity Index are preferred. A larger Specificity Index indicates greater specificity for efficacy in inhibition of neuronal protein extravasation over vasoconstriction. Thus, preferred compounds have a Specificity Index of greater than or equal to 10 (at least 10), preferably greater than or equal to 100 (at least 100). More preferred compounds have a Specificity Index of greater than or equal to 1000 (at least 1000), and yet more preferred compounds have Specificity Indexes greater than or equal to 5000 (at least 5000).

Pharmaceutical Compositions

The type of pharmaceutical composition used for the administration of the compounds employed in the methods of the present invention may be dictated by the particular compounds selected, the type of pharmacokinetic profile desired from the route of administration, and the state of the patient.

Pharmaceutical compositions amenable to oral, sublingual, nasal or injectable administration are prepared in a manner well known in the pharmaceutical art and comprise at least one active compound. See, e.g., REMINGTON'S PHARMACEUTICAL SCIENCES, (16$^{th}$ ed. 1980)

In general, a pharmaceutical composition of the present invention includes an active ingredient (a compound of formula I) and is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the pharmaceutical compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, gels, suppositories, sterile injectable solutions, and sterile packaged powders.

In preparing a pharmaceutical composition, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the pharmaceutical composition, e.g., about 40 mesh. In one embodiment of the present invention, the particle size range is between about 0.1 µm to about 100 µm.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The pharmaceutical compositions can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compounds of the invention can be formulated so as to provide quick, sustained or delayed release of the active ingredient after administration to the patient by employing procedures known in the art.

While it is possible to administer a compound employed in the methods of this invention directly without any formulation, the compounds are usually administered in the form of pharmaceutical compositions comprising a pharmaceutically acceptable excipient and at least one active ingredient. These formulations can be administered by a variety of routes including oral, buccal, rectal, intranasal, transdermal, subcutaneous, intravenous, intramuscular, and intranasal. Many of the compounds employed in the methods of this invention are effective as both injectable and oral compositions.

In order to administer transdermally, a transdermal delivery device ("patch") is needed. Such transdermal patches may be used to provide continuous or discontinuous infusion of a compound of the present invention in controlled amounts. The construction and use of transdermal patches for the delivery of pharmaceutical agents is well known in the art. See, e.g., U.S. Pat. No. 5,023,252. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, which is herein incorporated by reference. The delivery of hydrophilic drugs may be enhanced by intra-arterial infusion of hypertonic solutions, which can transiently open the blood-brain barrier.

In one preferred embodiment of the present invention, there is provided a pharmaceutical composition comprising at lest one compound as described above in a pharmaceutical composition adapted for buccal and/or sublingual, or nasal administration. This embodiment provides administration of the active compound in a manner that avoids gastric complications, such as first pass metabolism by the gastric system and/or through the liver. This administration route may also reduce adsorption times, providing more rapid onset of therapeutic benefit. The compounds of the present invention may provide particularly favorable solubility profiles to facilitate sublingual/buccal pharmaceutical compositions. Such pharmaceutical compositions typically require relatively high concentrations of active ingredients to deliver sufficient amounts of active ingredients to the limited surface area of the sublingual/buccal mucosa for the relatively short durations the pharmaceutical composition is in contact with the surface area, to allow the absorption of the active ingredient. Thus, the very high activity of the compounds of the present invention facilitate their suitability for sublingual/buccal pharmaceutical compositions.

A compound of formula I is preferably formulated in a unit dosage form, each dosage containing from about 0.001 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient as described above.

The compounds of the present invention are generally effective over a wide dosage range. For examples, dosages per day normally fall within the range of about 0.0001 to about 30 mg/kg of body weight. In the treatment of adult humans, the range of about 0.1 to about 15 mg/kg/day, in single or divided dose, is especially preferred.

However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

What is claimed:

1. The compound 2-chloro-4-fluoro-N-(3-(1-methylpiperidin-4-ylamino)phenyl)benzamide or a pharmaceutically acceptable acid addition salt thereof.

2. The compound 2-chloro-4-fluoro-N-(3-(1-methylpiperidin-4-ylamino)phenyl)benzamide dihydrochloride salt.

3. The compound 2-chloro-4-fluoro-N-(3-(1-methylpiperidin-4-ylamino)phenyl)benzamide fumarate salt.

4. A pharmaceutical composition comprising an effective amount of the compound or salt according to claim 1 and a pharmaceutical carrier, diluent, or excipient.

5. A pharmaceutical composition comprising an effective amount of the salt according to claim 2 and a pharmaceutical carrier, diluent, or excipient.

6. A pharmaceutical composition comprising an effective amount of the salt according to claim 3 and a pharmaceutical carrier, diluent, or excipient.

* * * * *